United States Patent
Carrino et al.

(10) Patent No.: US 7,033,801 B2
(45) Date of Patent: Apr. 25, 2006

(54) COMPOSITIONS AND METHODS FOR RAPIDLY GENERATING RECOMBINANT NUCLEIC ACID MOLECULES

(75) Inventors: John Carrino, San Diego, CA (US); James Fan, San Diego, CA (US); Robert P. Bennett, Encinitas, CA (US); Jonathan D. Chesnut, Encinitas, CA (US); Martin A. Gleeson, San Diego, CA (US); Knut R. Madden, Carlsbad, CA (US)

(73) Assignee: Invitrogen Corporation, Carlsbad, CA (US)

( * ) Notice: Subject to any disclaimer, the term of this patent is extended or adjusted under 35 U.S.C. 154(b) by 125 days.

(21) Appl. No.: 10/014,128

(22) Filed: Dec. 7, 2001

(65) Prior Publication Data

US 2006/0029935 A1 Feb. 9, 2006

Related U.S. Application Data

(60) Provisional application No. 60/254,510, filed on Dec. 8, 2000, provisional application No. 60/326,092, filed on Sep. 28, 2001.

(51) Int. Cl.
C12P 19/34 (2006.01)
(52) U.S. Cl. .................................................. 435/91.41
(58) Field of Classification Search .................. 435/6, 435/7.1, 91.1, 91.2, 257.2; 536/22.1, 23.1, 536/24.3, 33
See application file for complete search history.

(56) References Cited

U.S. PATENT DOCUMENTS

| | | | |
|---|---|---|---|
| 4,661,450 A | 4/1987 | Kempe et al. | |
| 4,800,159 A | 1/1989 | Mullis et al. | |
| 5,162,209 A | 11/1992 | Scheele | 435/91 |
| 5,605,802 A * | 2/1997 | Trono et al. | 435/7.4 |
| 5,624,826 A | 4/1997 | Kato et al. | |
| 5,746,997 A | 5/1998 | Reed | 424/1.73 |
| 5,766,891 A * | 6/1998 | Shuman | 435/91.41 |
| 5,851,808 A | 12/1998 | Elledge et al. | 435/172.3 |
| 5,958,681 A | 9/1999 | Wetmur et al. | |
| 5,981,182 A | 11/1999 | Jacobs, Jr. et al. | 435/6 |
| 6,013,440 A | 1/2000 | Lipshutz et al. | |
| 6,140,086 A | 10/2000 | Fox et al. | |
| 6,174,669 B1 | 1/2001 | Hayashizaki et al. | 435/6 |
| 6,238,884 B1 | 5/2001 | Short et al. | |
| 6,277,632 B1 | 8/2001 | Harney | |
| 6,280,977 B1 | 8/2001 | Liang et al. | |
| 6,291,213 B1 | 9/2001 | Rothstein | |
| 6,340,595 B1 | 1/2002 | Vogels et al. | |
| 6,537,776 B1 | 3/2003 | Short | |
| 6,548,277 B1 | 4/2003 | Shuman | |
| 6,653,106 B1 | 11/2003 | Shuman et al. | 435/91.1 |
| 2001/0044137 A1 | 11/2001 | Heyman et al. | |
| 2002/0025561 A1 | 2/2002 | Hodgson | |
| 2002/0028444 A1 | 3/2002 | Harney et al. | |
| 2002/0068290 A1* | 6/2002 | Yarovinsky | 435/6 |
| 2002/0182731 A1 | 12/2002 | Ji et al. | |

FOREIGN PATENT DOCUMENTS

| | | |
|---|---|---|
| EP | 0 373 914 A2 | 6/1990 |
| EP | 0 625 572 A1 | 11/1994 |
| EP | 1 018 549 A1 | 7/2000 |
| WO | WO 96/34981 | 11/1976 |
| WO | 85/04898 | 11/1985 |
| WO | WO 94/29443 | 12/1994 |
| WO | WO 96/19497 | 6/1996 |
| WO | WO 97/24455 | 7/1997 |
| WO | WO 97/48716 | 12/1997 |
| WO | WO 98/20122 | 5/1998 |
| WO | WO 98/55502 | 12/1998 |
| WO | WO 98/56943 | 12/1998 |
| WO | WO 00/12687 | 3/2000 |
| WO | WO 00/56878 | 9/2000 |
| WO | WO 01/62892 A2 | 8/2001 |
| WO | WO 01/62943 A1 | 8/2001 |
| WO | WO 02/16594 A2 | 2/2002 |

OTHER PUBLICATIONS

Stweart Shuman. Novel approach to molecular cloning and polynucleotide synthesis using Vaccinia DNA topoisomerase. 1994. The Journal of Biological Chemistry 269: 32678-32684.*

(Continued)

*Primary Examiner*—Jeffrey Fredman
(74) *Attorney, Agent, or Firm*—DLA Piper Rudnick Gray Cary US LLP

(57) ABSTRACT

A method of generating a double stranded (ds) recombinant nucleic acid molecule covalently linked in both strands by contacting two or more ds nucleotide sequences with a topoisomerase under conditions such that both termini of at least one end of a first ds nucleotide sequence are covalently linked by the topoisomerase to both termini of at least one end of a second ds nucleotide sequence is provided. Also provided is a method for generating a ds recombinant nucleic acid molecule covalently linked in one strand, by contacting two or more ds nucleotide sequences with a type IA topoisomerase under conditions such that one strand, but not both strands, of one or both ends of a first ds nucleotide sequence are covalently linked by the topoisomerase. Compositions for performing such methods, and compositions generated from such methods also are provided, as are kits containing components useful for conveniently practicing the methods.

51 Claims, 10 Drawing Sheets

OTHER PUBLICATIONS

Heyman et al., "Genome-Scale Cloning and Expression of Individual Open Reading Frames Using Topoisomerase I-Mediated Ligation," *Genome Research*, pp. 383-392 (1999).

Carninci et al. "High-Efficiency Full-Length cDNA Cloning by Biotinylated CAP Trapper," *Genomics*, 37(3):327-36 (1996) Academic Press, Inc.

Carninci et al. "High Efficiency Selection of Full-Length cDNA by Improved Biotinylated Cap Trapper," *DNA Research*, 4:61-66 (1997). Universal Academy Press.

Cheng and Shuman, "DNA Strand Transfer Catalyzed by Vaccinia Topoisomerase: Ligation of DNAs Containing a 3' Mononucleotide Overhang," *Nucleic Acids Res.*, 28(9): 1893-1898. (2000). Oxford University Press.

Cheng and Shuman, "Recombinogenic Flap Ligation Pathway for Intrinsic Repair of Topoisomerase IB-Induced Double-Strand Breaks," *Mol. Cell. Biol.* 20(21):8059-8068 (2000) American Society for Microbiology.

Cheng and Shuman, "Site-Specific DNA Transesterification by Vaccinia Topoisomerase: Role of Specific Phosphates and Nucleosides," *Biochemistry* 38(50):16599-16612 (1999) American Chemical Society.

Cheng and Shuman, "A Catalytic Domain of Eukaryotic DNA Topoisomerase I," *J. Biol. Chem.* 273(19):11589-11595 (1998) The American Society for Biochemistry and Molecular Biology, Inc.

Cheng et al., "Conservation of Structure and Mechanism Between Eukaryotic Topoisomerase I and Site-Specific Recombinases," *Cell.* 92(6):841-850 (1998) Cell Press.

Cheng et al., "Mutational Analysis of 39 Residues of Vaccinia DNA Topoisomerase Identifies Lys-220, Arg-223, and Asn-228 as Important for Covalent Catalysis," *J. Biol. Chem.* 272(13):8263-8269 (1997) The American society for Biochemistry and Molecular Biology, Inc.

DiGate and Marians, "Molecular Cloning and DNA Sequence Analysis of *Escherichia coli* topB, the Gene Encoding Topoisomerase III," *J. Biol. Chem.* 264(30): 17924-17930 (1989). The American society for Biochemistry and Molecular Biology, Inc.

Edery et al., "An Efficient Strategy to Isolate Full-Length cDNAs Based on an mRNA Cap Retention Procedure (CAPture)," *Mol. Cell. Biol.*, 15(6):3363-3371 (1995). American Society for Microbiology.

Ericsson et al., "Characterization of ts16, a Temperature-Sensitive Mutant of Vaccinia Virus," *J. Virol.*, 69(11):7072-7086 (1995) American Society for Microbiology.

Gross and Shuman, "Vaccinia Virions Lacking the RNA Helicase Nucleoside Triphosphate Phosphohydrolase II are Defective in Early Transcription," *J. Virol.* 70(12):8549-8557 (1996) American Society for Microbiology.

Haghighat and Sonenberg. "eIF4G Dramatically Enhances the Binding of eIF4E to the mRNA 5'-Cap Structure," *J. Biol. Chem.*, 272(35):21677-21680 (1997). The American society for Biochemistry and Molecular Biology, Inc.

Haghighat et al., "The eIF4G-eIF4E Complex is the Target for Direct Cleavage by the Rhinovirus 2A Proteinase," *J. Virol.* 70:8444-8450 (1996). American Society for Microbiology.

Henningfeld and Hecht, "A Model for Topoisomerase I-Mediated Insertions and Deletions with Duplex DNA Substrates Containing Branches, Nicks, and Gaps," *Biochemistry* 34(18):6120-6129. (1995) American Chemical Society.

Invitrogen Corporation. *Invitrogen Catalog*, Carlsbad, California, pp. 18, 29, 43, 44, 49-52 (1998).

Jannknecht et al., "Rapid and Efficient Purification of Native Histidine-Tagged Protein Expressed by Recombinant Vaccinia Virus," *Proc. Natl. Acad. Sci., U S A* 88:8972-8976 (1991) National Academic of Sciences.

Kane and Shuman, "Vaccinia Virus Morphogenesis is Blocked by a Temperature-Sensitive Mutation in the I7 Gene that Encodes a Virion Component," *J. Virol.* 67(5):2689-2698 (1993) American Society for Microbiology.

Kato et al., "Construction of a Human Full-Length cDNA Bank," *Gene.* 150: 243-250 (1994) Elsevier Science.

Klemm et al., "Peptide Inhibitors of DNA Cleavage by Tyrosine Recombinases and Topoisomerases," *J. Mol. Biol.* 299(5):1203-1216. (2000) Academic Press, Inc.

Klemperer et al., "Identification and Characterization of the orf Virus Type I Topoisomerase," *Virology* 206:203-215 (1995) Academic Press, Inc.

Krogh and Shuman, "Vaccinia Topoisomerase Mutants Illuminate Conformational Changes During Closure of the Protein Clamp and Assembly of a Functional Active Site," *J. Biol. Chem.* Jul. 5, 2001 [Manuscript] The American Society for Biochemistry and Molecular Biology, Inc.

Krogh and Shuman, "Catalytic Mechanism of DNA Topoisomerase IB," *Mol. Cell.*, 5(6):1035-1041 (2000) Cell Press.

Krogh and Shuman, "DNA Strand Transfer Catalyzed by Vaccinia Topoisomerase: Peroxidolysis and Hydroxylaminolysis of the Covalent Protein-DNA Intermediate," *Biochemistry* 39(21):6422-6432. (2000) American Chemical Society.

Krogh et al., "Effect of 2'-5' Phosphodiesters on DNA Transesterification by Vaccinia Topoisomerase," *J. Biol. Chem.* 276(24):20907-20912. (2001) The American Society for Biochemistry and Molecular Biology, Inc.

Krogh et al., "Melanoplus Sanguinipes Entomopoxvirus DNA Topoisomerase: Site-Specific DNA Transesterification and Effects of 5'-Bridging Phosphorothiolates," *Virology* 264(2):441-451. (1999) Academic Press, Inc.

Liu et al., "Mapping the 5' and 3' Ends of Tetrahymena thermophila mRNAs Using RNA Ligase Mediated Amplification of cDNA Ends (RLM-RACE)," *Nucleic Acids Research* 21(21): 4954-4960. (1993) The Oxford University Press.

Lockard et al., "Labeling of Eukaryotic Messenger RNA 5' Terminus with Phosphorus-32: Use of Tobacco Acid Pyrophosphatase for Removal of Cap Structures," *Gene Amplification and Analysis* 2:229-251. (1981) Elsevier Science.

Maruyama and Sugano, "Oligo-Capping: A Simple Method to Replace the Cap Structure of Eukaryotic mRNAs with Oligoribonucleotides," *Gene.* 138:171-174 (1994).

Morham and Shuman, "Covalent and Noncovalent DNA Binding by Mutants of Vaccinia DNA Topoisomerase I," *J. Biol. Chem.* 267:15984-15992 (1992) The American Society for Biochemistry and Molecular Biology, Inc.

Morham and Shuman, "Phenotypic Selection and Characterization of Mutant Alleles of a Eukaryotic DNA Topoisomerase I," *Genes. Dev.* 4(4):515-524 (1990) Cold Spring Harbor Laboratory Press.

Palaniyar et al. "SFV Topoisomerase: Sequence Specificity in a Genetically Mapped Interval," *Virology* 221:351-354 (1996). American Press, Inc.

Petersen and Shuman, "DNA Strand Transfer Reactions Catalyzed by Vaccinia Topoisomerase: Hydrolysis and Glycerololysis of the Covalent Protein-DNA Intermediate," *Nucleic Acids Res.* 25(11):2091-2097 (1997) Oxford University Press.

Petersen and Shuman, "Histidine 265 is Important for Covalent Catalysis by Vaccinia Topoisomerase and is Conserved in all Eukaryotic Type I Enzymes," *J. Biol. Chem.* 272(7):3891-3896 (1997) The American Society for Biochemistry and Molecular Biology, Inc.

Petersen et al., "Characterization of a DNA Topoisomerase Encoded by Amsacta Moore Entomopoxvirus," *Virology* 230(2):197-206 (1997) Academic Press, Inc.

Petersen et al., "Mutations within a Conserved Region of Vaccinia Topoisomerase Affect the DNA Cleavage-Religation Equilibrium," *J. Mol. Biol.* 1263(2):181-195 (1996) Academic Press Limited.

Salazar et al., "The DNA Strand in DNA·RNA Hybrid Duplexes is Neither B-Form nor A-Form in Solution," *Biochemistry* 32(16):4207-4215 (1993) American Chemical Society.

Schmitt et al., "Affinity Purification of Histidine-Tagged Proteins," *Molecular Biology Reports* 18:223-230 (1993).

Sekiguchi and Shuman, "Domain Structure of Vaccinia DNA Ligase," *Nucleic Acids Res.* 25(4):727-734 (1997) Kluwer Academic Publishers.

Sekiguchi and Shuman, "Mutational Analysis of Vaccinia Virus Topoisomerase Identifies Residues Involved in DNA Binding," *Nucleic Acids Res..* 25(18):3649-3656. (1997) Oxford University Press.

Sekiguchi and Shuman, "Nick Sensing by Vaccinia Virus DNA Ligase Requires a 5' Phosphate at the Nick and Occupancy of the Adenylate Binding Site On the Enzyme," *J. Virol.* 71(12):9679-84 (1997) American Society for Microbiology.

Sekiguchi and Shuman, "Site-Specific Ribonuclease Activity of Eukaryotic DNA Topoisomerase I," *Mol. Cell.* 1(1):89-97.(1997) Cell Press.

Sekiguchi and Shuman, "Covalent DNA Binding by Vaccinia Topoisomerase Results in Unpairing of the Thymine Base 5' of the Scissile Bond," *J. Biol. Chem.* 271(32):19436-19442 (1996). The American Society for Biochemistry and Molecular Biology, Inc.

Sekiguchi and Shuman, "Identification of Contacts Between Topoisomerase I and Its Target DNA by Site-Specific Photocrosslinking," *EMBO J.* 15(13):3448-3457 (1996) Oxford University Press.

Sekiguchi and Shuman, "Proteolytic Footprinting of Vaccinia Topoisomerase Bound to DNA," *J. Biol. Chem..* 270(19):11636-11645 (1995) The American Society for Biochemistry and Molecular Biology, Inc.

Sekiguchi and Shuman, "Requirements for Noncovalent Binding of Vaccinia Topoisomerase I to Duplex DNA," *Nucleic Acids Res.* 22(24):5360-5 (1994) Oxford University Press.

Sekiguchi and Shuman, "Stimulation of Vaccinia Topoisomerase I by Nucleoside Triphosphates," *J. Biol. Chem.* 269(47):29760-29764 (1994) The American Society for Biochemistry and Molecular Biology, Inc.

Sekiguchi and Shuman, "Vaccinia Topoisomerase Binds Circumferentially to DNA," *J. Biol. Chem.* 269(50):31731-31734 (1994) The American Society for Biochemistry and Molecular Biology, Inc.

Sekiguchi, et al., "Resolution of a Holliday Junction by Vaccinia Topoisomerase Requires a Spacer DNA Segment 3' of the CCCTT↓ Cleavage Sites," *Nucleic Acids Res.* 28(14):2658-2663. (2000) Oxford University Press.

Sekiguchi et al., "Kinetic Analysis of DNA and RNA Strand Transfer Reactions Catalyzed by Vaccinia Topoisomerase," *J. Biol. Chem..* 272(25):15721-15728 (1997) The American Society for Biochemistry and Molecular Biology, Inc.

Sekiguchi, et al., "Mechanism of Inhibition of Vaccinia DNA Topoisomerase by Novobiocin and Coumermycin," *J. Biol. Chem.* 271(4):2313-2322 (1996) The American Society for Biochemistry and Molecular Biology, Inc.

Sekiguchi et al., "Resolution of Holliday Junctions by Eukaryotic DNA Topoisomerase I," *Proc. Natl. Acad. Sci. U S A.* 93(2):785-789. (1996) National Academic of Sciences.

Shuman, "Analysis of Topoisomerase-DNA Interactions by Electrophoretic Mobility Shift Assay," *Methods Mol. Biol.* 95:65-74(2001) Hunana Press, Inc.

Shuman, "Polynucleotide Ligase Activity of Eukaryotic Topoisomerase I," *Mol. Cell.* 1(5):741-748. (1998) Cell Press.

Shuman, "Vaccinia Virus DNA Topoisomerase: a Model Eukaryotic Type IB Enzyme," *Biochim. Biophys. Acta.* 1400(1-3):321-337. (1998) Elsevier Science.

Shuman, "Vaccinia Virus DNA Ligase: Specificity, Fidelity, and Inhibition," *Biochemistry* 34:16138-16147 (1995) American Chemical Society.

Shuman, "Novel Approach to Molecular Cloning and Polynucleotide Synthesis Using Vaccinia DNA Topoisomerase" *J. Biol. Chem..* 269(51):32678-32684 (1994).

Shuman, "DNA Strand Transfer Reactions Catalyzed by Vaccinia Topoisomerase I", *J. Biol. Chem.* 267:8620-8627. (1992) The American Society for Biochemistry and Molecular Biology, Inc.

Shuman, "Two Classes of DNA End-Joining Reactions Catalyzed by Vaccinia Topoisomerase I", *J. Biol. Chem..* 267:16755-16758. (1992) The American Society for Biochemistry and Molecular Biology, Inc.

Shuman, "Recombination Mediated by Vaccinia Virus DNA Topoisomerase I In *Escherichia coli* is Sequence specific," *Proc. Natl. Acad. Sci. U S A.* 88(22):10104-10108 (1991) National Academic of Sciences.

Shuman, "Site-Specific DNA Cleavage by Vaccinia Virus DNA Topoisomerase I. Role of Nucleotide Sequence and DNA Secondary Structure," *J. Biol. Chem..* 266(3):1796-1803 (1991) The American Society for Biochemistry and Molecular Biology, Inc.

Shuman, "Site-Specific Interaction of Vaccinia Virus Topoisomerase I with Duplex DNA. Minimal DNA Substrate for Strand Cleavage in vitro," *J. Biol. Chem.* 266(17):11372-11379 (1991) The American Society for Biochemistry and Molecular Biology, Inc.

Shuman, "Vaccinia DNA Topoisomerase I Promotes Illegitimate Recombination in *Escherichia coli,*" *Proc. Natl. Acad. Sci. U S A.* 86(10):3489-3493 (1989) National Academic of Sciences.

Shuman and Moss, "Identification of a Vaccinia Virus Gene Encoding a Type I DNA Topoisomerase," *Proc. Natl. Acad. Sci., U S A* 84:7478-7482. (1987) National Academic of Sciences.

Shuman and Prescott, "Specific DNA Cleavage and Binding of Vaccinia Virus DNA Topoisomerase I" *J. Biol. Chem..* 265:17826-17836. (1990) The American Society for Biochemistry and Molecular Biology, Inc.

Shuman and Turner, "Site-Specific Interaction of Vaccinia Virus Topoisomerase I with Base and Sugar Moieties in Duplex DNA," *J. Biol. Chem.* 268(25):18943-18950 (1993)

The American Society for Biochemistry and Molecular Biology, Inc.
Shuman et al., "Intramolecular Synapsis of Duplex DNA by Vaccinia Topoisomerase," *EMBO J.* 16(21):6584-6589 (1997) Oxford University Press.
Shuman et al., "Insertional Mutagenesis of the Vaccinia Virus Gene Encoding a Type I DNA Topoisomerase: Evidence that the Gene is Essential for Virus Growth," *Virology.* 170(1):302-306 (1989) Academic Press, Inc.
Shuman et al., "Mapping the Active-Site Tyrosine of Vaccinia Virus DNA Topoisomerase I," *Proc. Natl. Acad. Sci. U S A.* 86(24):9793-9797 (1989) National Academic of Sciences.
Shuman et al., "Characterization of Vaccinia Virus DNA Topoisomerase I Expressed in *Escherichia coli*", *J. Biol. Chem..* 263:16401-16407. (1988) The American Society for Biochemistry and Molecular Biology, Inc.
Stivers et al., "Stereochemical Outcome and Kinetic Effects of Rp- and Sp-Phosphorothioate Substitutions at the Cleavage Site of Vaccinia Type I DNA Topoisomerase," *Biochemistry* 39(18):5561-5572. (2000) American Chemical Society.
Stivers et al., "Vaccinia DNA Topoisomerase I: Kinetic Evidence for General Acid-Base Catalysis and a Conformational Step," *Biochemistry* 33(51):15449-15458 (1994) American Chemical Society.
Stivers et al., "Vaccinia DNA Topoisomerase I: Single-Turnover and Steady-State Kinetic Analysis of the DNA Strand Cleavage and Ligation Reactions," *Biochemistry* 33(1):327-339 (1994) American Chemical Society.
Wang and Shuman, "Deletions at the Carboxyl terminus of Vaccinia DNA Topoisomerase Affect DNA Binding and Enhance Distributivity in DNA Relaxation," *Biochemistry* 36(13):3909-3916 (1997) American Chemical Society.
Wang et al., "Mutational Analysis of 26 Residues of Vaccinia DNA Topoisomerase Identifies Ser-204 as Important for DNA Binding and Cleavage," *Biochemistry* 36(26):7944-7950 (1997) American Chemical Society.
Wexler et al., "A Procedure to Amplify cDNA from dsRNA Templates Using the Polymerase Chain Reaction," *Methods in Molecular and Cellular Biology* 2:273-279 (1991).
Wittschieben and Shuman, "Mechanism of DNA Transesterification by Vaccinia Topoisomerase: Catalytic Contributions of Essential Residues Arg-130, Gly-132, Tyr-136 and Lys-167," *Nucleic Acids Res.* 25(15):3001-3008. (1997) Oxford University Press.

Wittschieben and Shuman, "Mutational Analysis of Vaccinia DNA Topoisomerase Defines Amino Acid Residues Essential for Covalent Catalysis," *J. Biol. Chem.* 269(47): 29978-29983 (1994) The American Society for Biochemistry and Molecular Biology, Inc.
Wittschieben et al., "Replacement of the Active Site Tyrosine of Vaccinia DNA Topoisomerase by Glutamate, Cysteine or Histidine Converts the Enzyme into a Site-Specific Endonuclease," *Nucleic Acids Res.* 26(2):490-496. (1998) Oxford University Press.
Woodfield et al., "Vaccinia Topoisomerase and Cre Recombinase Catalyze Direct Ligation of Activated DNA Substrates Containing a 3'-Para-Nitrophenyl Phosphate Ester," *Nucleic Acids Res.* 28(17):3323-3331 (2000) Oxford University Press.
Yang et al., "A Eukaryotic Enzyme that can Disjoin Dead-End Covalent Complexes Between DNA and Type I Topoisomerases," *Proc. Natl. Acad. Sci. U S A.* 93(21): 11534-11539 (1996) National Academic of Sciences.
Arnott et al., "DNA-RNA Hybrid Secondary Structures," *J. Mol. Biol.*, vol. 188, pp. 631-640 (1986).
Chong et al., "Single-column purification of free recombinant proteins using a self-cleavable affinity tage derived from a protein splicing element", *Gene*, vol. 192, pp. 271-281 (1997).
Matthews et al., "Analytical Strategies for the Use of DNA Probes", *Anal. Biochem.*, vol. 169, pp. 1-25 (1988).
Sambrook et al., *Molecular Cloning—A Laboratory Manual*, 2nd Ed., Cold Springs Harbor Laboratory Press, pp. 2.53-2.54, 16.8-16.9, 16.20 and 16.22 (1989).
Shatkin, "Capping of Eucaryotic mRNAs", *Cell*, vol. 9, pp. 645-653 (1976).
Theus et al., "A Simple Assay for Determining the Capping Efficiencies of RNA Polymerases Used for In Vitro Transcription", *BioTechniques*, vol. 9, pp. 610-615 (1990).
Yarovinsky, "Application of DNA Topoisomerase-Activated Adapters to Riboprobe Synthesis", *BioTechniques*, vol. 28, pp. 1160-1165 (2000).
Zechiedrich et al., "Topoisomerase IV, not gyrase, decatenates products of site-specific recombination in *Escherichia coli*", *Genes & Development*, vol, 11, pp. 2580-2592 (1997).
Sykes and Johnston, "Linear Expression Elements: A Rapid, *In Vivo*, Method to Screen For Gene Functions", Nature Biotechnology, vol. 17, pp. 355-359, Apr. 1999.

* cited by examiner

SEQUENCE LISTING

<160> NUMBER OF SEQ ID NOS: 47

<210> SEQ ID NO 1
<211> LENGTH: 27
<212> TYPE: DNA
<213> ORGANISM: ARTIFICIAL SEQUENCE
<220> FEATURE:
<223> OTHER INFORMATION: PRIMER MTH1

<400> SEQUENCE: 1
tatgtatcat acacatacga tttaggt                27

<210> SEQ ID NO 2
<211> LENGTH: 20

```
<212> TYPE: DNA
<213> ORGANISM: ARTIFICIAL SEQUENCE
<220> FEATURE:
<223> OTHER INFORMATION: PRIMER MTH2

<400> SEQUENCE: 2
accgcctctc cccgcgcgtt                                                  20

<210> SEQ ID NO 3
<211> LENGTH: 34
<212> TYPE: DNA
<213> ORGANISM: ARTIFICIAL SEQUENCE
<220> FEATURE:
<223> OTHER INFORMATION: PRIMER GAL4r2

<400> SEQUENCE: 3
gttccgaagg gggcgataca gtcaactgtc tttg                                  34

<210> SEQ ID NO 4
<211> LENGTH: 36
<212> TYPE: DNA
<213> ORGANISM: ARTIFICIAL SEQUENCE
<220> FEATURE:
<223> OTHER INFORMATION: PRIMER MTH5

<400> SEQUENCE: 4
ttggccaagg gtatctagaa gcttctgcag acgcgt                                36

<210> SEQ ID NO 5
<211> LENGTH: 34
<212> TYPE: DNA
<213> ORGANISM: ARTIFICIAL SEQUENCE
<220> FEATURE:
<223> OTHER INFORMATION: PRIMER VP16r2

<400> SEQUENCE: 5
gttccgaagg gccaccgtac tcgtcaattc caag                                  34

<210> SEQ ID NO 6
<211> LENGTH: 36
<212> TYPE: DNA
<213> ORGANISM: ARTIFICIAL SEQUENCE
<220> FEATURE:
<223> OTHER INFORMATION: PRIMER SV40pAF

<400> SEQUENCE: 6
ggccaaaagg gaacttgttt attgcagctt ataatg                                36

<210> SEQ ID NO 7
<211> LENGTH: 22
<212> TYPE: DNA
<213> ORGANISM: ARTIFICIAL SEQUENCE
<220> FEATURE:
<223> OTHER INFORMATION: PRIMER SV40pAr

<400> SEQUENCE: 7
ctctgacttg agcgtcgatt tt                                               22

<210> SEQ ID NO 8
<211> LENGTH: 32
<212> TYPE: DNA
<213> ORGANISM: ARTIFICIAL SEQUENCE
<220> FEATURE:
<223> OTHER INFORMATION: PRIMER p53f2

<400> SEQUENCE: 8
```
cggaacaagg ggaattccct gtcaccgaga cc                              32

<210> SEQ ID NO 9
<211> LENGTH: 34
<212> TYPE: DNA
<213> ORGANISM: ARTIFICIAL SEQUENCE
<220> FEATURE:
<223> OTHER INFORMATION: PRIMER SVTf2

<400> SEQUENCE: 9
cggaacaagg ggaattcccg gggatctgga attc                            34

<210> SEQ ID NO 10
<211> LENGTH: 29
<212> TYPE: DNA
<213> ORGANISM: ARTIFICIAL SEQUENCE
<220> FEATURE:
<223> OTHER INFORMATION: PRIMER CMVr2

<400> SEQUENCE: 10
tcgaaagggt cgaggtcgac ctgcagctg                                  29

<210> SEQ ID NO 11
<211> LENGTH: 26
<212> TYPE: DNA
<213> ORGANISM: ARTIFICIAL SEQUENCE
<220> FEATURE:
<223> OTHER INFORMATION: PRIMER CMVf

<400> SEQUENCE: 11
aattcacatt gattattgag tagtta                                     26

<210> SEQ ID NO 12
<211> LENGTH: 30
<212> TYPE: DNA
<213> ORGANISM: ARTIFICIAL SEQUENCE
<220> FEATURE:
<223> OTHER INFORMATION: PRIMER GFP-Xhof

<400> SEQUENCE: 12
tcgaaagggt aatggccagc aaaggagaag                                 30

<210> SEQ ID NO 13
<211> LENGTH: 27
<212> TYPE: DNA
<213> ORGANISM: ARTIFICIAL SEQUENCE
<220> FEATURE:
<223> OTHER INFORMATION: PRIMER GFP-Notr

<400> SEQUENCE: 13
ggccaagggt ttgtagagct catccat                                    27

<210> SEQ ID NO 14
<211> LENGTH: 29
<212> TYPE: DNA
<213> ORGANISM: ARTIFICIAL SEQUENCE
<220> FEATURE:
<223> OTHER INFORMATION: PRIMER BGHf2

<400> SEQUENCE: 14
ggccaagggt ctgaatgggg ccgcatagt                                  29

<210> SEQ ID NO 15
<211> LENGTH: 20
<212> TYPE: DNA
<213> ORGANISM: ARTIFICIAL SEQUENCE

```
<220> FEATURE:
<223> OTHER INFORMATION: PRIMER BGHr

<400> SEQUENCE: 15
aagccataga gcccgggcca                                              20

<210> SEQ ID NO 16
<211> LENGTH: 31
<212> TYPE: DNA
<213> ORGANISM: ARTIFICIAL SEQUENCE
<220> FEATURE:
<223> OTHER INFORMATION: PRIMER CMVr2

<400> SEQUENCE: 16
gttccgaagg gtcgaggtcg acctgcagct g                                 31

<210> SEQ ID NO 17
<211> LENGTH: 30
<212> TYPE: DNA
<213> ORGANISM: ARTIFICIAL SEQUENCE
<220> FEATURE:
<223> OTHER INFORMATION: PRIMER GFPf3

<400> SEQUENCE: 17
cggaacaagg gatggccagc aaaggagaag                                   30

<210> SEQ ID NO 18
<211> LENGTH: 31
<212> TYPE: DNA
<213> ORGANISM: ARTIFICIAL SEQUENCE
<220> FEATURE:
<223> OTHER INFORMATION: PRIMER GFPr3

<400> SEQUENCE: 18
taggccaagg gtttgtagag ctcatccatg c                                 31

<210> SEQ ID NO 19
<211> LENGTH: 29
<212> TYPE: DNA
<213> ORGANISM: ARTIFICIAL SEQUENCE
<220> FEATURE:
<223> OTHER INFORMATION: PRIMER BGHf3

<400> SEQUENCE: 19
ggcctaaagg gtgaatgggg ccgcatagt                                    29

<210> SEQ ID NO 20
<211> LENGTH: 50
<212> TYPE: DNA
<213> ORGANISM: ARTIFICIAL SEQUENCE
<220> FEATURE:
<223> OTHER INFORMATION: PRIMER T7top

<400> SEQUENCE: 20
gaaggagtaa tacgactcac tatagggagc caccatgggc ccttcggaac             50

<210> SEQ ID NO 21
<211> LENGTH: 50
<212> TYPE: DNA
<213> ORGANISM: ARTIFICIAL SEQUENCE
<220> FEATURE:
<223> OTHER INFORMATION: PRIMER T7bottom

<400> SEQUENCE: 21
gttccgaagg gcccatggtg gctccctata gtgagtcgta ttactccttc             50
```

<210> SEQ ID NO 22
<211> LENGTH: 21
<212> TYPE: DNA
<213> ORGANISM: ARTIFICIAL SEQUENCE
<220> FEATURE:
<223> OTHER INFORMATION: PRIMER T7amp

<400> SEQUENCE: 22
gaaggagtaa tacgactcac t                                              21

<210> SEQ ID NO 23
<211> LENGTH: 38
<212> TYPE: DNA
<213> ORGANISM: ARTIFICIAL SEQUENCE
<220> FEATURE:
<223> OTHER INFORMATION: PRIMER T3top

<400> SEQUENCE: 23
ggcctaaagg gtccctttag tgagggttaa ttgcgcgc                             38

<210> SEQ ID NO 24
<211> LENGTH: 38
<212> TYPE: DNA
<213> ORGANISM: ARTIFICIAL SEQUENCE
<220> FEATURE:
<223> OTHER INFORMATION: PRIMER T3bottom

<400> SEQUENCE: 24
gcgcgcaatt aaccctcact aaagggaccc tttaggcc                             38

<210> SEQ ID NO 25
<211> LENGTH: 34
<212> TYPE: DNA
<213> ORGANISM: ARTIFICIAL SEQUENCE
<220> FEATURE:
<223> OTHER INFORMATION: PRIMER lacZf2

<400> SEQUENCE: 25
cggaacaagg gatgatagat cccgtcgttt taca                                 34

<210> SEQ ID NO 26
<211> LENGTH: 32
<212> TYPE: DNA
<213> ORGANISM: ARTIFICIAL SEQUENCE
<220> FEATURE:
<223> OTHER INFORMATION: PRIMER lacZ1k2

<400> SEQUENCE: 26
taggccaagg ggaccatttt caatccgcac ct                                   32

<210> SEQ ID NO 27
<211> LENGTH: 32
<212> TYPE: DNA
<213> ORGANISM: ARTIFICIAL SEQUENCE
<220> FEATURE:
<223> OTHER INFORMATION: PRIMER lacZ2k2

<400> SEQUENCE: 27
taggccaagg ggaggcactt caccgcttgc ca                                   32

<210> SEQ ID NO 28
<211> LENGTH: 33
<212> TYPE: DNA
<213> ORGANISM: ARTIFICIAL SEQUENCE
<220> FEATURE:
<223> OTHER INFORMATION: PRIMER lacZ3k2

```
<400> SEQUENCE: 28
taggccaagg gtttgacacc agaccaactg gta                              33

<210> SEQ ID NO 29
<211> LENGTH: 9
<212> TYPE: DNA
<213> ORGANISM: ARTIFICIAL SEQUENCE
<220> FEATURE:
<223> OTHER INFORMATION: CMV ELEMENT

<400> SEQUENCE: 29 tcgaaaggg                                                          9

<210> SEQ ID NO 30
<211> LENGTH: 9
<212> TYPE: DNA
<213> ORGANISM: ARTIFICIAL SEQUENCE
<220> FEATURE:
<223> OTHER INFORMATION: GFP ELEMENT

<400> SEQUENCE: 30 tcgaaaggg                                                          9

<210> SEQ ID NO 31
<211> LENGTH: 9
<212> TYPE: DNA
<213> ORGANISM: ARTIFICIAL SEQUENCE
<220> FEATURE:
<223> OTHER INFORMATION: GFP ELEMENT

<400> SEQUENCE: 31 ggccaaggg                                                          9

<210> SEQ ID NO 32
<211> LENGTH: 9
<212> TYPE: DNA
<213> ORGANISM: ARTIFICIAL SEQUENCE
<220> FEATURE:
<223> OTHER INFORMATION: BGH ELEMENT

<400> SEQUENCE: 32 ggccaaggg                                                          9

<210> SEQ ID NO 33
<211> LENGTH: 11
<212> TYPE: DNA
<213> ORGANISM: ARTIFICIAL SEQUENCE
<220> FEATURE:
<223> OTHER INFORMATION: CMV ELEMENT

<400> SEQUENCE: 33
gttccgaagg g                                                      11

<210> SEQ ID NO 34
<211> LENGTH: 11
<212> TYPE: DNA
<213> ORGANISM: ARTIFICIAL SEQUENCE
<220> FEATURE:
<223> OTHER INFORMATION: GFP ELEMENT

<400> SEQUENCE: 34
cggaacaagg g                                                      11

<210> SEQ ID NO 35
```

```
<211> LENGTH: 9
<212> TYPE: DNA
<213> ORGANISM: ARTIFICIAL SEQUENCE
<220> FEATURE:
<223> OTHER INFORMATION: GFP ELEMENT

<400> SEQUENCE: 35 ggccaaggg                                                            9

<210> SEQ ID NO 36
<211> LENGTH: 9
<212> TYPE: DNA
<213> ORGANISM: ARTIFICIAL SEQUENCE
<220> FEATURE:
<223> OTHER INFORMATION: BGH ELEMENT

<400> SEQUENCE: 36 ggccaaggg                                                            9

<210> SEQ ID NO 37
<211> LENGTH: 11
<212> TYPE: DNA
<213> ORGANISM: ARTIFICIAL SEQUENCE
<220> FEATURE:
<223> OTHER INFORMATION: CMV ELEMENT

<400> SEQUENCE: 37
gttccgaagg g                                                        11

<210> SEQ ID NO 38
<211> LENGTH: 11
<212> TYPE: DNA
<213> ORGANISM: ARTIFICIAL SEQUENCE
<220> FEATURE:
<223> OTHER INFORMATION: GFP ELEMENT

<400> SEQUENCE: 38
cggaacaagg g                                                        11

<210> SEQ ID NO 39
<211> LENGTH: 11
<212> TYPE: DNA
<213> ORGANISM: ARTIFICIAL SEQUENCE
<220> FEATURE:
<223> OTHER INFORMATION: GFP ELEMENT

<400> SEQUENCE: 39
taggccaagg g                                                        11

<210> SEQ ID NO 40
<211> LENGTH: 11
<212> TYPE: DNA
<213> ORGANISM: ARTIFICIAL SEQUENCE
<220> FEATURE:
<223> OTHER INFORMATION: BGH ELEMENT

<400> SEQUENCE: 40
ggcctaaagg g                                                        11

<210> SEQ ID NO 41
<211> LENGTH: 11
<212> TYPE: DNA
<213> ORGANISM: ARTIFICIAL SEQUENCE
<220> FEATURE:
<223> OTHER INFORMATION: Segment of amplified nucleic acid molecule

<400> SEQUENCE: 41
```

```
atccggttcc c                                                        11

<210> SEQ ID NO 42
<211> LENGTH: 11
<212> TYPE: DNA
<213> ORGANISM: ARTIFICIAL SEQUENCE
<220> FEATURE:
<223> OTHER INFORMATION: Segment of amplified nucleic acid molecule

<400> SEQUENCE: 42
gccttgttcc c                                                        11

<210> SEQ ID NO 43
<211> LENGTH: 11
<212> TYPE: DNA
<213> ORGANISM: ARTIFICIAL SEQUENCE
<220> FEATURE:
<223> OTHER INFORMATION: Segment of TOPO adapted element

<400> SEQUENCE: 43
ggccataagg g                                                        11

<210> SEQ ID NO 44
<211> LENGTH: 16
<212> TYPE: DNA
<213> ORGANISM: ARTIFICIAL SEQUENCE
<220> FEATURE:
<223> OTHER INFORMATION: Segment of nucleic acid molecule

<400> SEQUENCE: 44
cccttggcca taaggg                                                   16

<210> SEQ ID NO 45
<211> LENGTH: 16
<212> TYPE: DNA
<213> ORGANISM: ARTIFICIAL SEQUENCE
<220> FEATURE:
<223> OTHER INFORMATION: Segment of nucleic acid molecule

<400> SEQUENCE: 45
ccctttaggc caaggg                                                   16

<210> SEQ ID NO 46
<211> LENGTH: 16
<212> TYPE: DNA
<213> ORGANISM: ARTIFICIAL SEQUENCE
<220> FEATURE:
<223> OTHER INFORMATION: Segment of nucleic acid molecule

<400> SEQUENCE: 46
cccttcggaa caaggg                                                   16

<210> SEQ ID NO 47
<211> LENGTH: 16
<212> TYPE: DNA
<213> ORGANISM: ARTIFICIAL SEQUENCE
<220> FEATURE:
<223> OTHER INFORMATION: Segment of nucleic acid molecule

<400> SEQUENCE: 47
cccttgttcc gaaggg                                                   16
```

COMPOSITIONS AND METHODS FOR RAPIDLY GENERATING RECOMBINANT NUCLEIC ACID MOLECULES This application claims the benefit under 35 U.S.C. 119(e) of U.S. Ser. No. 60/254,510, filed Dec. 8, 2000, and U.S. Ser. No. 60/326,092, filed Sep. 28, 2001, the entire contents of each of which is incorporated herein by reference.

BACKGROUND OF THE INVENTION

1. Field of the Invention

The invention relates generally to compositions and methods for facilitating the construction of recombinant nucleic acid molecules, and more specifically to compositions for using one or more topoisomerases to generate covalently closed recombinant nucleic acid molecules and to methods of making such recombinant nucleic acid molecules.

2. Background Information

The advent of recombinant DNA technology has allowed the cloning and identification of genes from many different organisms, and the determination of the complete genomes of an ever-increasing number of organisms, including humans. The elucidation of a large number of new and uncharacterized genes creates a pressing need for technologies that enable rapid expression and analysis of these genes. The ability to construct recombinant nucleic acid molecules has provided a means to produce novel "gene products" and to express gene products, particularly heterologous gene products, in cells, tissues and organisms in which they are not normally produced. Thus, recombinant DNA technology has led, for example, to the fields of gene therapy, in which defective genes are replaced by copies of a normal gene; and "biopharming," in which, for example, a gene product such as an antibody, which normally is produced by an animal, is expressed in a plant, thereby allowing large scale production of the gene product.

Despite the great leaps in progress that have resulted from the discovery and development of recombinant DNA methods, a great number of steps often is required to prepare a novel DNA construct having desired properties. A significant bottleneck in recombinant DNA methodology is the requirement that each nucleic acid sequence that is to be used to prepare a construct must be cloned into a vector, the vector must be introduced into and amplified in a host cell (generally a bacterial cell), the amplified vector must be isolated from the host cell, and then must be transformed or transfected into the appropriate cell type for expression. Vectors with the appropriate functional elements such as a promoter, an origin of replication, a selectable marker, an epitope tag, or the like may need to be constructed. Such methods require multiple restriction enzyme digestion and ligation steps, in addition to numerous purification and characterization steps.

Methods and products are being developed to reduce the number of steps required to obtain a desired nucleic acid construct. For example, many commercial suppliers provide vectors that contain one or more functional elements of interest, and have cloning sites such that a desired nucleotide sequence can be cloned in frame with the sequences in the vector. However, such vectors are limited in that only the most commonly used elements such as particularly useful promoters or tags or the like can be included in the vectors in order for the vector to be commercially viable.

In some cases, there may be no need to covalently ligate together nucleic acid sequences that have been allowed to join. For example, non-covalently linked constructs formed by hybridization of complementary overhanging ends can be used to transfect cells with a reasonably high efficiency. However, such constructs effectively contain "nicks" at the sites of hybridization and, therefore, are more susceptible to endonuclease degradation than covalently linked sequences. Furthermore, constructs containing nicks are not suitable for certain further manipulations such as amplification by a polymerase chain reaction. Thus, a need exists to identify methods for facilitating the preparation of nucleic acid constructs. The present invention satisfies this need and provides additional advantages.

SUMMARY OF THE INVENTION

The present invention relates to methods of covalently linking, in one or both strands, two or more double stranded (ds) nucleotide sequences using one or more topoisomerases. As such, the invention also provides, in part, nucleotide sequences that can be covalently linked according to such methods, recombinant nucleic acid molecules generated therefrom, and compositions comprising the nucleotide sequence and/or recombinant nucleic acid molecules (e.g., reaction mixtures), wherein the nucleotide sequences contain at least one topoisomerase attached thereto (e.g., a covalently linked topoisomerase), at least one topoisomerase recognition site, or a combination thereof.

In particular embodiments, at least one topoisomerase recognition site can be internal, i.e., within one or more nucleotide sequences, or can be at or near one or both termini of a single stranded nucleotide sequence or one or both strands of double stranded nucleotide sequence; or at least one bound topoisomerase can be at or near one or both termini of a single stranded nucleotide sequence or one or both strands of a double stranded nucleotide sequence, and can be present on 5' overhang, a 3' overhang, or at a blunt end. For example, one or more of the at least one topoisomerase or the at least one topoisomerase recognition site can be located at or near a 5' terminus, at or near a 3' terminus, at or near both 5' termini, at or near both 3' termini, at or near a 5' terminus and a 3' terminus, at or near a 5' terminus and both 3' termini, or at or near a 3' terminus and both 5' termini. The invention provides methods for preparing and using nucleotide sequences and covalently linked recombinant nucleic acid molecules generated therefrom, compositions containing one or more of such nucleotide sequences or recombinant nucleic acid molecule, and nucleic acid molecules and compositions derived therefrom. In specific aspects, the invention provides nucleotide sequences 1) to which topoisomerases of various types (e.g., a type IA topoisomerase, a type IB topoisomerase, a type II topoisomerase, etc.) are attached (e.g., covalently bound); and/or 2) which contain two or more topoisomerase recognition sites that can be bound and/or cleaved by various types of topoisomerases; and/or 3) which contain a combination of such bound various topoisomerases and various topoisomerase recognition sites, as well as methods for preparing and using compositions comprising such nucleotide sequences.

The invention further provides methods for covalently linking two or more nucleotide sequences, wherein at least one of the nucleotide sequences contains at least one topoisomerase bound thereto or one topoisomerase recognition site. Further, when nucleotide sequences used in methods of the invention contain more than one topoisomerase, either on the same or different nucleotide sequences, the topoisomerase can be of the same type or of different types.

Similarly, when nucleotide sequences used in methods of the invention contain more than one topoisomerase recognition site, either on the same or different nucleotide sequences, the topoisomerase recognition sites can be recognized by topoisomerases of the same type or of different types. Thus, the invention provides methods for covalently linking nucleotide sequences employing any one topoisomerase or topoisomerase recognition site. The invention also provides methods for covalently linking nucleotide sequences using any combination of topoisomerases and/or topoisomerase recognition sites. The invention also provides covalently linked recombinant nucleic acid molecules produced by such methods, and further provides compositions containing such recombinant nucleic acid molecules and uses of these molecules.

The present invention generally provides, in part, methods for covalently linking any number of nucleotide sequences (e.g., two, three, four, five, six, seven, eight, nine, ten, etc.), including nucleotide sequences containing different functional or structural elements. As such, the invention provides, in part, methods for covalently linking any number of nucleotide sequences (e.g., two, three, four, five, six, seven, eight, nine, ten, etc.) that confer different properties upon a covalently linked recombinant nucleic acid molecule generated therefrom. In many instances, the methods of the invention result in the formation of recombinant nucleic acid molecules having operative interactions of properties and/or elements of individual nucleotide sequences that are covalently linked to generate the recombinant nucleic acid molecules (e.g., an operative interaction/linkage between an expression control element and an open reading frame). Examples of 1) functional and structural elements and 2) properties that can be conferred upon a recombinant nucleic acid molecule generated according to a method of the invention include, but are not limited to, multiple cloning sites (e.g., nucleotide sequences that contain at least two restriction endonuclease cleavage sites), packaging signals (e.g., viral packaging signals such as adenoviral packaging signals, alphaviral packaging signals, etc.), restriction endonuclease cleavage sites, open reading frames (e.g., intein coding sequences, affinity purification tag coding sequences, etc.), expression control sequences (e.g., promoters, operators, etc.), and the like. Additional elements and properties that can be conferred by one or more nucleotide sequences upon a product recombinant nucleic acid molecule are exemplified herein or otherwise known in the art. The present invention also provides covalently linked recombinant nucleic acid molecules produced by the methods described above, as well as uses of these molecules and compositions containing these molecules.

The invention also provides compositions that contain nucleotide sequences and/or recombinant nucleic acid molecules as disclosed herein. For example, compositions of the invention include, but are not limited to, mixtures (e.g., reaction mixtures) containing a nucleotide sequence comprising at least one topoisomerase recognition site, and at least one topoisomerase that recognizes at least one of the at least one topoisomerase recognition sites of the nucleotide sequence. Compositions of the invention further include at least one nucleotide sequence comprising 1) at least one topoisomerase recognition site or at least one nucleotide sequence to which at least one topoisomerase is attached (e.g., covalently bound) and 2) one or more additional components. Examples of such additional components include, but are not limited to, topoisomerases; additional nucleotide sequence that can, but need not, comprise one or more topoisomerases or topoisomerase recognition sites; buffers; salts; polyamines (e.g., spermine, spermidine, etc.); water; or any other component as disclosed herein or as desired.

In one embodiment, the invention provides a method of using a topoisomerase (e.g., a type JA or type IB topoisomerase) to covalently link a first ds nucleotide sequence to at least a second ds nucleotide sequence, thereby generating a recombinant ds nucleic acid molecule that is covalently linked in at least one strand. Such a method can be used, for example, to covalently link three or more (e.g., 3, 4, 5, 6, 7, etc.) ds nucleotide sequences, so as to generate a recombinant ds nucleic acid molecule containing one strand that has no nicks. In particular embodiments of a method of generating a recombinant double stranded nucleic acid molecule that is covalently linked in only one strand, the topoisomerase is not a type IB topoisomerase.

In another embodiment, the invention provides a method of using a type IA topoisomerase and a type IB topoisomerase to covalently link at least two ds nucleotide sequences in at least one strand. For example, a first ds nucleotide sequence can contain a type IA topoisomerase at the 5' terminus of one end and a type IB topoisomerase at the 3' terminus of the second end of the same strand, thereby providing a means to covalently link a strand of the first ds nucleotide sequence to one or more other ds nucleotide sequences to generate a recombinant ds nucleic acid molecule that is covalently linked in one strand. In another embodiment, the present invention provides a method to covalently link two or more ds nucleotide sequences in both strands, for example, by contacting an end of a first ds nucleotide sequence having a type IA or a type IB topoisomerase bound thereto, to an end of a second ds nucleotide sequence having a type IA or type IB topoisomerase, respectively, bound thereto; or by contacting a first ds nucleotide sequence having a type IA topoisomerase and a type IB topoisomerase bound to the 5' terminus and 3' terminus, respectively, of an end, with a second ds nucleotide sequence. The invention also provides compositions comprising nucleic acid molecules with topoisomerase bound to a 5' terminus and/or a 3' terminus, as well as precursor nucleotide sequences having one or more topoisomerase recognition sites for preparing covalently linked recombinant nucleic acid molecules having a topoisomerase bound to a 5' and/or 3' terminus.

The present invention also relates to methods of generating a double stranded recombinant nucleic acid molecule, which is covalently linked in one or both strands, by contacting two or more (e.g., 2, 3, 4, 5, 6, 7, 8, 9, 10, etc) ds nucleotide sequences with at least one (e.g., 1, 2, 3, 4, 5, 6, 7, 8, 9, 10, etc.) topoisomerase. For example, the present invention provides methods for generating a ds recombinant nucleic acid molecule covalently linked in both strands, and methods for generating a ds recombinant nucleic acid molecule covalently linked in at least one strand.

A method for generating a ds recombinant nucleic acid molecule that is covalently linked in one strand generally is performed by contacting a site-specific topoisomerase (e.g., a type IA or type IB topoisomerase) and at least one (e.g., 1, 2, 3 4, 5, 6, 7, 8, 9, 10, etc.) ds nucleotide sequences to be joined under conditions such that at least one strand of an end of each ds nucleotide sequence is covalently linked to at least one strand of an end of any one or two other ds nucleotide sequences. Such a method can be used to generate, for example, a ds recombinant nucleic acid molecule, wherein one strand contains a nick at the site or sites at which the substrate ds nucleotide sequences are ligated. The present invention also provides recombinant nucleic acid molecules prepared by such a method, further provides nucleotide sequences used in such a method.

A method of generating a ds recombinant nucleic acid molecule covalently linked in at least one strand can be performed using various combinations of components. For example, the method can be performed by contacting at least one (e.g., 1, 2, 3 4, 5, 6, 7, 8, 9, 10, etc.) substrate ds nucleotide sequence to be linked and at least one (e.g., 1, 2, 3 4, 5, 6, 7, 8, 9, 10, etc.) site-specific topoisomerase (e.g., a type IA topoisomerase or type IB topoisomerase), wherein the topoisomerase cleaves one or both strands of the substrate ds nucleotide sequences and forms a stable complex with a nucleotide at a terminus of the cleavage site. The topoisomerase-charged end or topoisomerase-charged ds nucleotide sequence is then contacted with another end or ds nucleotide sequence, which is, or can be, charged with a topoisomerase, (e.g., a type IA or type IB topoisomerase) such that one strand, but not both strands, at one or both ends of the substrate ds nucleotide sequences is linked, thereby generating one or more ds recombinant nucleic molecules covalently linked in one strand. The site-specific type IA topoisomerase, and type IB topoisomerase when present, links one strand of each ds nucleotide sequence through the formation of a phosphodiester bond at each linkage site.

A method of generating a ds recombinant nucleic acid molecule that is covalently linked in at least one strand also can be performed by contacting at least one site-specific topoisomerase-charged ds nucleotide sequence (e.g., a ds nucleotide sequence charged with a type IA or a type IB topoisomerase), with at least a second topoisomerase-charged ds nucleotide sequence (e.g., a ds nucleotide sequence charged with a type IA or a type IB topoisomerase); or by contacting at least one topoisomerase-charged ds nucleotide sequence (e.g., a ds nucleotide sequence charged with a type IA or type IB topoisomerase) with at least one ds nucleotide sequence that contains a topoisomerase cleavage site, in the presence of excess topoisomerase; or by contacting at least one site-specific topoisomerase-charged ds nucleotide sequence (e.g., a ds nucleotide sequence charged with a type IA or a type IB topoisomerase) with at least one ds nucleotide sequence; or by contacting at least one ds nucleotide sequence that contains a site-specific topoisomerase cleavage site (e.g., a type IA or type IB topoisomerase cleavage site), and at least one ds nucleotide sequence, in the presence of an excess of site-specific topoisomerase (e.g., type IA or type IB topoisomerase, respectively). The present invention also provides recombinant nucleic acid molecules prepared by such a method, as well as compositions for performing such methods. Such compositions include, for example, a topoisomerase-charged ds nucleotide sequence, wherein topoisomerase is covalently linked to one or both 5' termini; a 5' terminus and one or both 3' termini; or both 5' termini and both 3' termini.

Such a method also can be performed by contacting 1) a first ds nucleotide sequence having a first end and a second end, wherein the first ds nucleotide sequence has a site-specific topoisomerase recognition site (e.g., a type IA or type II topoisomerase recognition site) at or near the 5' terminus of the first end or the second end; 2) at least a second ds nucleotide sequence having a first end and a second end; and 3) at least one (e.g., 1, 2, 3, 4, 5, 6, 7, 8, 9, 10, etc.) site specific topoisomerase, under conditions such that all components are in contact and the at least one topoisomerase can effect its activity. For example, the topoisomerase can be a type IA topoisomerase such as *E. coli* topoisomerase I, *E. coli* topoisomerase III, or a eukaryotic topoisomerase III. Upon cleavage of the first ds nucleotide sequence, the topoisomerase preferably is stably bound to a 5' terminus. Preferably, upon cleavage by the topoisomerase, the cleaved ds nucleotide sequence comprises a 3' overhanging sequence.

The method also can be performed by contacting 1) a first ds nucleotide sequence having a first end and a second end, wherein the first ds nucleotide sequence has a site-specific topoisomerase recognition site (e.g., a type IA or a type II topoisomerase recognition site) at or near the 5' terminus of the first end or the second end or both ends; 2) at least a second ds nucleotide sequence that has, or can be made to have, a first end and a second end; and 3) at least one (e.g., 1, 2, 3, 4, 5, 6, 7, 8, 9, 10, etc.) site-specific type IA topoisomerase, under conditions such that all components are in contact and the at least one topoisomerase can effect its activity. For example, the topoisomerase can be a type IA topoisomerase such as *E. coli* topoisomerase I, *E. coli* topoisomerase III, or a eukaryotic topoisomerase III. Upon cleavage of a ds nucleotide sequence, the topoisomerase preferably is stably bound to the 5' terminus. Preferably, upon cleavage by the topoisomerase, the cleaved ds nucleotide sequence comprises a 3' overhanging sequence. As such, a method of the invention provides a means wherein any combination of ends can be linked, and wherein one strand of the product recombinant nucleic acid molecule is covalently linked and the second strand is not covalently linked (i.e., contains a nick).

A method of generating a ds recombinant nucleic acid molecule covalently linked in one strand, involving a first ds nucleotide sequence and at least a second ds nucleotide sequence, can further include a step of amplifying the ds recombinant nucleic acid molecule covalently linked in one strand. The amplification can be carried out by contacting the ds recombinant nucleic acid molecule with an amplification reaction primer pair, wherein a first primer of the primer pair can bind to the covalently linked strand, at or near one end of the first or second ds nucleotide sequence, and prime an amplification reaction in a direction toward the other (i.e., second or first, respectively) ds nucleotide sequence to generate a first extension product that is identical in nucleotide sequence to the nicked strand of the ds recombinant nucleic acid molecule. The second primer of the primer pair is selected such that it can bind to the first extension product, typically at or near the 3' terminus of the first extension product, and, in the presence of the first primer, can generate an amplification product using the covalently-linked strand and the first extension product (or extension products generated therefrom) as templates. For example, the method can be performed such that the topoisomerase recognition site (e.g., type IA topoisomerase recognition site) is at or near the first end of the first ds nucleotide sequence, and the method can further include contacting the generated ds recombinant nucleic acid molecule with an amplification reaction primer pair, wherein a forward primer is capable of binding at or near the second end of the first ds nucleotide sequence and wherein a reverse primer is capable of binding to a nucleotide sequence complementary to at least a portion of the second end of the second ds nucleotide sequence; and amplifying the ds recombinant nucleic acid molecule. By way of example, the first ds nucleotide sequence can include a coding region and the second ds nucleotide sequence can include a regulatory element, and the generated recombinant nucleic acid molecule can comprise an expressible nucleotide sequence.

A method for generating a ds recombinant nucleic acid molecule covalently linked in one strand also can be performed by contacting 1) a first ds nucleotide sequence having a first end and a second end, wherein the first ds nucleotide sequence has a site-specific topoisomerase recognition site (e.g., type IA or type II topoisomerase recognition site) at or near the 5' terminus of the first end or the second end or both; 2) at least a second ds nucleotide sequence that has, or can be made to have, a first end and a second end; 3) at least a third ds nucleotide sequence which has, or can be made to have, a first end and a second end, each end further comprising a 5' terminus and a 3' terminus; and 4) at least one (e.g., 1, 2, 3, 4, 5, 6, 7, 8, 9, 10, etc.) site-specific topoisomerase (e.g., at least one type IA topoisomerase), under conditions such that all components are in contact and the at least one topoisomerase can effect its activity. For example, the topoisomerase can be a type IA topoisomerase such as E. coli topoisomerase I, E. coli topoisomerase III, or a eukaryotic topoisomerase III. Upon cleavage of a ds nucleotide sequence, the topoisomerase preferably is stably bound to the 5' terminus. Preferably, upon cleavage by the topoisomerase, the cleaved ds nucleotide sequence comprises a 3' overhanging sequence.

A method of the invention for generating a ds recombinant nucleic acid molecule covalently linked in one strand, involving a first ds nucleotide sequence that contains a site-specific topoisomerase recognition site (e.g., a type IA or type IB topoisomerase recognition site), or cleavage product thereof, at least a second ds nucleotide sequence, and at least a third ds nucleotide sequence can be performed such that any combination of ends are linked, and one strand at the ends being linked is covalently linked and one strand is nicked. Furthermore, in this embodiment, any of the ends can contain a type IA or type IB topoisomerase recognition site, or cleavage product thereof, provided that the first ds recombinant nucleotide molecule contains a type IA or type II topoisomerase recognition site at or near a 5' terminus, or cleavage product thereof, and only one topoisomerase or topoisomerase recognition site is present at the ends that are to be linked. For example, where the first ds nucleotide sequence comprises a type IA site-specific topoisomerase recognition site at or near each of said first end and said second end, the method further can include contacting the first ds nucleotide sequence and the second ds nucleotide sequence with at least a third ds nucleotide sequence which has, or can be made to have, a first end and a second end, each end further comprising a 5' terminus and a 3' terminus, under conditions such that the type IA topoisomerase can covalently link the 5' terminus of the first end of the first ds nucleotide sequence with the 3' terminus of the first end of the second nucleotide sequence, and the 5' terminus of the second end of the first ds nucleotide sequence with the 3' terminus of the first end of the third nucleotide sequence. It will be recognized that other combinations of ends and topoisomerase recognition sites, or cleavage products thereof, can be used in practicing a method of the invention.

In another embodiment, a method for generating a ds recombinant nucleic acid molecule covalently linked in one strand can be performed by contacting 1) a first ds nucleotide sequence having a first end and a second end, wherein the first ds nucleotide sequence has a site-specific topoisomerase recognition site (e.g., a type IA or type II topoisomerase recognition site) at or near the 5' terminus of an end and a type IB topoisomerase recognition site at or near the 3' terminus of the other end; 2) at least a second ds nucleotide sequence that has, or can be made to have, a first end and a second end; 3) at least one (e.g., 1, 2, 3, 4, 5, 6, 7, 8, 9, 10, etc.) site-specific type IA topoisomerase; and 4) at least one (e.g., 1, 2, 3, 4, 5, 6, 7, 8, 9, 10, etc.) type IB topoisomerase under conditions such that all components are in contact and the at least one topoisomerase can effect its activity. For example, the topoisomerase recognition site at or near a 5' terminus of the first ds nucleotide sequence can be a type IA topoisomerase such as E. coli topoisomerase I, E. coli topoisomerase III, or a eukaryotic topoisomerase III. Upon cleavage of a ds nucleotide sequence, the type IA topoisomerase preferably is stably bound to the 5' terminus, and the type IB topoisomerase preferably is stably bound at the 3' terminus. Preferably, upon cleavage by the topoisomerases, the cleaved ds nucleotide sequence comprises a 3' overhanging sequence and a 5' overhanging sequence.

Methods of the invention can further include contacting the ds recombinant nucleic acid molecule with one or more (e.g., 1, 2, 3, 4, 5, etc.) enzymes or agents having ligase activity (e.g., a DNA ligase such as T4 DNA ligase) 1) to covalently link gaps, particularly nicks, in one or both strands of the product ds recombinant nucleic acid molecule to obtain a ds recombinant nucleic acid molecule covalently linked in both strands; 2) to link a product ds nucleic acid molecule to one or more other molecules; and/or 3) to circularize the product ds recombinant nucleic acid molecule.

A method for generating a ds recombinant nucleic acid molecule covalently linked in one strand, involving a first ds nucleotide sequence, a second ds nucleotide sequence, and at least a third ds nucleotide sequence, can further include a step for amplifying the ds recombinant nucleic acid molecule covalently linked in one strand using, for example, an amplification reaction such as a polymerase chain reaction. Such a method can be used to amplify any portion of the generated ds recombinant nucleic acid molecule, particularly all or a portion of the covalently linked strand, including a portion of the covalently linked strand that includes all or a part of each of the substrate first, second and third ds nucleotide sequences. For example, where the ds recombinant nucleic acid molecule comprises an end of the first ds nucleotide sequence linked to an end of the second ds nucleotide and an end of the third ds nucleotide sequence linked to the other end of the second ds nucleotide sequence, the amplification can be carried out by contacting the ds recombinant nucleic acid molecule with an amplification reaction primer pair, wherein a first primer of the primer pair is capable of binding to the covalently linked strand at or near one end of the first or third ds nucleotide sequence and priming an amplification reaction in a direction toward the second ds nucleotide sequence to generate a first extension product that is complementary to the covalently linked strand; and the second primer of the primer pair can bind to the first extension product, typically at or near the 3' terminus of the first extension product, which can include a sequence complementary to at least a portion of the second nucleotide sequence and can further include a sequence complementary to the third or first ds nucleotide sequence, respectively, and, in the presence of the first primer, can generate an amplification product using the covalently linked strand and the extension product (or extension products generated therefrom) as templates. The method can be performed such that the topoisomerase recognition site (e.g., type IA or type IB topoisomerase recognition site) is at or near the first end of the first ds nucleotide sequence, and the method further includes contacting the ds recombinant nucleic acid molecule with an amplification reaction primer pair, wherein a forward primer is capable of binding to a nucleotide sequence at or near the second end of the first ds nucleotide sequence and wherein a reverse primer is capable of binding to a nucleotide sequence complementary to at least a portion of the third ds nucleotide sequence; and amplifying the ds recombinant nucleic acid molecule. By way of example, the first ds nucleotide sequence can include a first regulatory element such as a transcriptional promoter and/or an operator (e.g., a tetracycline operator), the second ds nucleotide sequence can include a coding region, and the third ds nucleotide sequence can include a second regulatory element such as a transcriptional termination sequence. Furthermore, ends being linked according to a method of the invention can contain complementary overhanging sequences. The present invention also provides recombinant nucleic acid molecules or amplification products thereof produced using such a method.

Methods of the invention for generating a ds recombinant nucleic acid molecule covalently linked in one strand, are further exemplified by contacting 1) a first ds nucleotide sequence having a first end and a second end, wherein, at the first end, second end, or both ends, the first ds nucleotide sequence has a topoisomerase covalently bound to a 5' terminus (i.e., a topoisomerase-charged 5' terminus); and 2) at least a second nucleotide sequence, under condition such that the topoisomerases can covalently link one strand, but not both strands, of one or both ends of the first ds nucleotide sequence with one or both ends of at least the second ds nucleotide sequence. The ds nucleotide sequences can contain a 3' hydroxyl group at the end of a strand being linked to a 5' terminus by topoisomerase, or a 3' hydroxyl group can be generated using a phosphatase. As disclosed herein, such a method can be performed using only a first ds nucleotide sequence and a second ds nucleotide sequence, or can include a third, fourth, fifth, or more ds nucleotide sequences as desired, wherein each nucleotide sequence is as defined, including optionally comprising one or two topoisomerase-charged termini. A second (or other) ds nucleotide sequence independently can have a topoisomerase covalently bound to a 5' terminus of one end or at both ends of the ds nucleotide sequence, and, unless indicated otherwise, the first and second (or other) ds nucleotide sequences can be the same or can be different.

Methods of the invention for generating a ds recombinant nucleic acid molecule covalently linked in one strand, are further exemplified by contacting 1) a first ds nucleotide sequence having a first end and a second end, wherein, at the first end, second end, or both ends, the first ds nucleotide sequence has a topoisomerase covalently bound to a 5' terminus (i.e., a topoisomerase-charged 5' terminus); 2) at least a second nucleotide sequence which may or may not be charged with topoisomerase; and 3) at least a third nucleotide sequence which may or may not be charged with topoisomerase, under condition such that the topoisomerases can covalently link one strand, but not both strands, of one or both ends of the first ds nucleotide sequence with one or both ends of at least the second ds nucleotide sequence, or one or both ends of at least the third ds nucleotide sequence. The ds nucleotide sequences can contain a 3' hydroxyl group at the end of a strand being linked to a 5' terminus by topoisomerase, or a 3' hydroxyl group can be generated using a phosphatase. The second, third, (or other) ds nucleotide sequence independently can have a topoisomerase covalently bound to a 5' terminus of one end or at both ends of the ds nucleotide sequence, and, unless indicated otherwise, the first, second, third (or other) ds nucleotide sequences can be the same or can be different.

In another embodiment, a method for generating a ds recombinant nucleic acid molecule covalently linked in one strand can be performed by contacting 1) a first ds nucleotide sequence having a first end and a second end, wherein a site-specific topoisomerase (e.g., a type IA or type II topoisomerase) is bound at the 5' terminus of the first end, the second end, or both the first end and the second end; and 2) at least a second ds nucleotide sequence that has, or can be made to have, a first end and a second end, under conditions such that all components are in contact and the at least one topoisomerase can effect its activity. For example, a type IA topoisomerase such as *E. coli* topoisomerase I, *E. coli* topoisomerase III, or a eukaryotic topoisomerase III, can be used. The ds nucleotide sequences can include a 3' overhanging sequence, a 5' overhanging sequence, or can be blunt ended.

In another embodiment, a method for generating a ds recombinant nucleic acid molecule covalently linked in one strand can be performed by contacting 1) a first ds nucleotide sequence having a first end and a second end, wherein a site-specific topoisomerase (e.g., a type IA or type II topoisomerase) is bound at the 5' terminus of the first end, the second end, or both the first end and the second end; 2) at least a second ds nucleotide sequence that has, or can be made to have, a first end and a second end; wherein a site-specific topoisomerase (e.g., a type IA or type II topoisomerase) can be bound at the 5' terminus of the first end, the second end, or both the first end and the second end; and 3) at least a third ds nucleotide sequence that has, or can be made to have, a first end and a second end, wherein a site-specific topoisomerase (e.g., a type IA or type II topoisomerase) can be bound at the 5' terminus of the first end, the second end, or both the first end and the second end; under conditions such that all components are in contact and the at least one topoisomerase can effect its activity. For example, the type IA topoisomerase can be *E. coli* topoisomerase I, *E. coli* topoisomerase III, or a eukaryotic topoisomerase III. The ds nucleotide sequences can include 3' overhanging sequences, 5' overhanging sequences, or can be blunt ended, or can have various combinations of such ends, which can facilitate directional linkage.

The present invention also relates to a method of generating a ds recombinant nucleic acid molecule covalently linked in one strand by 1) amplifying a portion of a first ds nucleotide sequence using a PCR primer pair, wherein at least one primer of the primer pair encodes a site-specific type IA topoisomerase recognition site, thereby producing an amplified first ds nucleotide sequence having a first end and a second end, wherein the first end, second end, or both ends have a topoisomerase recognition site at or near the 5' terminus; and 2) contacting a) the amplified first ds nucleotide sequence; b) at least a second ds nucleotide sequence having a first end and a second end; and c) at least one (e.g., 1, 2, 3, 4, 5, 6, 7, 8, 9, 10, etc.) site specific type IA topoisomerase, under conditions such that the at least one topoisomerase can cleave the first and/or second end of the amplified first ds nucleotide sequence having a type IA topoisomerase recognition site, and can effect its ligating activity. The PCR primer encoding the topoisomerase recognition site can further comprise a nucleotide sequence at its 5' terminus, i.e., 5' to the topoisomerase recognition site, such that, upon cleavage of the amplified first ds nucleotide sequence by a site specific topoisomerase, the ds nucleotide sequence contains a 3' overhanging sequence, which can be complementary to a 3' overhanging sequence of a second (or other) ds nucleotide sequence to which the first ds nucleotide sequence is to be linked according to a method of the invention for generating a ds recombinant nucleic acid molecule covalently linked in one strand. A second primer of the PCR primer pair can include the complement of a type IB topoisomerase recognition site, thereby producing an amplification product having a first end and a second end, wherein the amplification product comprises a type IA topoisomerase recognition site at or near the 5' terminus of one end and a type IB topoisomerase recognition site at or near the 3' terminus of the other end.

The present invention further relates to a ds recombinant nucleic acid molecule having, or which can be made to have, a first end and a second end, each end including a 5' terminus and a 3' terminus, wherein the ds recombinant nucleic acid molecule comprises a site-specific topoisomerase recognition site (e.g., type IA topoisomerase recognition site) at or near a 5' terminus of the first end, the second end, or both the first end and the second end. The ds recombinant nucleic acid molecule can further include a type IB topoisomerase recognition site at or near a 3' terminus of an end that does not include a type IA tupoisomerase recognition site. The ds recombinant nucleic acid molecule can be a vector, or can be a component of a vector, for example, a component that allows for convenient insertion of a regulatory element or an origin of replication or the like.

The present invention also relates to a topoisomerase-charged ds recombinant nucleic acid molecule having a first end and a second end, each end having a 5' terminus and a 3' terminus, wherein a site-specific type IA topoisomerase is bound at the 5' terminus of the first end, the second end, or both the first end and the second end. For example, the topoisomerase-charged nucleic acid ds recombinant nucleic acid molecule can include a type IA topoisomerase bound at the 5' termini of each of the first and second ends. The topoisomerase-charged nucleic acid ds recombinant nucleic acid molecule can include, for example, a type IB topoisomerase bound at a 3' terminus of an end not bound by a type IA topoisomerase, or can contain a site-specific topoisomerase recognition site at an end not bound by a type IA topoisomerase. The topoisomerase-charged nucleic acid ds recombinant nucleic acid molecule can comprise a vector or a component thereof, or can comprise a regulatory element or coding sequence or any other nucleic acid molecule of interest.

In one aspect, the methods of the invention allow joining of two or more nucleic acid sequences in a desired orientation and/or order, which, if desired, can be further manipulated or used in a variety of assays or procedures, including a transcription or transfection procedure, which can be performed in vitro or in vivo, a translation reaction or other protein expression procedure, and the like. In another aspect, (1) three or more, four or more, five or more, etc., or (2) a population or library of the same or different ds nucleotide sequences can be linked according to a method of the invention. In still another aspect, the methods of the invention can be used to link each end of a single nucleic acid molecule to form a circular or supercoiled molecule. In addition, where two or more nucleic acid sequences have been joined, the ends of the resulting ds recombinant nucleic acid molecule can be covalently linked in one or both strands according to a method of the invention to circularize the molecule.

The nucleotide sequences to be linked can be derived from any source, and can be naturally occurring and chemically or recombinantly synthesized nucleic acid molecules such as cDNA, genomic DNA, plasmids, vectors, oligonucleotides, and the like. Furthermore, the nucleotide sequences can, but need not, contain one or more functional sequences such as gene regulatory elements; origins of replication; splice sites; polyadenylation sites; packaging signals; multiple cloning sites; open reading frames, which can encode, for example, tag sequences, detectable or selectable markers, cell localization domains, or other peptide or polypeptide, or can encode an antisense nucleic acid molecule, ribozyme, tRNA or other RNA molecule; and the like. As such, a method of the invention allows any number of nucleotide sequences, which can be the same or different, to be covalently linked in one or both strands, including, if desired, in a predetermined order or orientation or both.

The ds nucleotide sequences to be linked can be in any form, for example, linear, circular, or supercoiled, and are characterized, in part, in that each ds nucleotide sequence to be linked is a substrate for a selected topoisomerase or can be modified to be a substrate. The topoisomerase can be any topoisomerase that can covalently link one strand of a ds nucleotide sequence to one strand of another ds nucleotide sequence, preferably through a phosphodiester bond. The topoisomerase can be a site specific topoisomerase or can have relaxed specificity, and preferably forms a stable complex (e.g., a covalent complex) with one strand of the ds nucleotide sequence at or near the site at which cleavage is effected.

In certain aspects, the present invention provides methods for generating a ds recombinant nucleic acid molecule that is covalently linked in both strands. Such a method can be performed by contacting topoisomerase and the ds nucleotide sequences to be joined under conditions such that both strands of an end of one ds nucleotide sequence are ligated to both strands of an end of at least one (e.g., 1, 2, 3 4, 5, 6, 7, 8, 9, 10, etc.) other ds nucleotide sequence. As such, a method of the invention generates a ds recombinant nucleic acid molecule that is covalently linked in both strands and, therefore, does not contain a nick in either strand at the site or sites at which the substrate ds nucleotide sequences are ligated. The present invention also provides recombinant nucleic acid molecules prepared according to such a method.

A method of generating a ds recombinant nucleic acid molecule covalently linked in both strands can be performed using various combinations of components. For example, the method can be performed by contacting two or more substrate ds nucleotide sequences to be covalently linked and at least one topoisomerase, wherein the topoisomerase cleaves one or both strands of the ds nucleotide sequences and forms a stable complex with a nucleotide at a terminus of the cleavage site. The topoisomerase-charged ends or topoisomerase-charged ds nucleotide sequences are then contacted with each other such that each strand of the substrate ds nucleotide sequences is linked, thereby generating one of more covalently linked ds recombinant nucleic molecules. Preferably, the topoisomerase mediates the formation of a phosphodiester bond at each linkage site. The method also can be performed by contacting two or more topoisomerase-charged ds nucleotide sequences, either alone, or in the presence of excess topoisomerase, or by contacting one or more topoisomerase-charged ds nucleotide sequences with one or more ds nucleotide sequences that contain a topoisomerase cleavage site, and a topoisomerase. The present invention also provides recombinant nucleic acid molecules prepared by such a method.

In various embodiments, the topoisomerase can have a relatively relaxed specificity such that it can bind to and cleave a variety of different nucleotide sequences, or the topoisomerase can be a site-specific topoisomerase, which binds to and cleaves a specific nucleotide sequence. The topoisomerase also can be a type I topoisomerase, which cleaves one strand of a ds nucleotide sequence, or can be a type II topoisomerase, which cleaves both strands of a ds nucleotide sequence. Where the topoisomerase is a type I topoisomerase, cleavage is effected such that a linear ds nucleotide sequence is produced, and is topoisomerase-charged at one or both ends. Preferably, the strand of the ds nucleotide sequence that is complementary to the strand containing the bound topoisomerase forms an overhanging sequence.

An advantage of performing a method of the invention is that the ligation reaction performed by a topoisomerase occurs very quickly and over a wide range of temperatures. Another advantage of the methods of the invention is that generated ds recombinant nucleic acid molecules that are covalently linked in one or both strands can be used directly in a subsequent procedure, for example, as a substrate for an amplification reaction such as a polymerase chain reaction (PCR), or as a substrate for a transcription or translation or coupled transcription/translation reaction.

By way of example, a method of the invention for generating a ds recombinant nucleic acid molecule covalently linked in both strands, can be performed by contacting 1) a first ds nucleotide sequence having a first end and a second end, wherein, at the first end or second end or both, the first ds nucleotide sequence has a topoisomerase recognition site at or near the 3' terminus; 2) at least a second ds nucleotide sequence having a first end and a second end, wherein, at the first end or second end or both, the at least second double stranded nucleotide sequence has a topoisomerase recognition site at or near a 3' terminus; and 3) at least one site specific topoisomerase (e.g., a type IA and/or a type IB topoisomerase), under conditions such that all components are in contact and the topoisomerase can effect its activity. Preferably, the strand complementary to that containing the topoisomerase recognition sequence comprises a 5' hydroxyl group, and more preferably, upon cleavage by the topoisomerase, comprises a 5' overhanging sequence.

A method of generating a ds recombinant nucleic acid molecule covalently linked in both strands also can be performed by contacting 1) a ds nucleotide sequence having a first end and a second end, wherein each of the first end and second end contains a topoisomerase recognition site at or near the 3' terminus, and 2) a site specific topoisomerase, under conditions such that the components are in contact and the topoisomerase can effect its activity. For example, the topoisomerase can be a type IB topoisomerase such as a Vaccinia topoisomerase or an *S. cerevisiae* topoisomerase. Such a method provides a means to prepare a covalently closed circular or supercoiled ds recombinant nucleic acid molecule.

A method of generating a ds recombinant nucleic acid molecule covalently linked in both strands also can be performed by contacting 1) a first ds nucleotide sequence having a first end and a second end, wherein the first ds nucleotide sequence has a topoisomerase recognition site at or near the 5' terminus of the first end or the second end or both; 2) at least a second ds nucleotide sequence having a first end and a second end, wherein the at least second double stranded nucleotide sequence has a topoisomerase recognition site at or near the 5' terminus of the first end or the second end or both; and 3) at least one site specific topoisomerase, under conditions such that all components are in contact and the at least one topoisomerase can effect its activity. For example, the topoisomerase can be a type IA topoisomerase such as *E. coli* topoisomerase I, *E. coli* topoisomerase III, or a eukaryotic topoisomerase III. Upon cleavage of a ds nucleotide sequence, the topoisomerase preferably is stably bound to the 5' terminus. The 3' terminus of the end containing the topoisomerase recognition site, or bound topoisomerase, can comprise a 3' hydroxyl group, or can be modified to comprise a 3' hydroxyl group. Preferably, upon cleavage by the topoisomerase, the cleaved ds nucleotide sequence comprises a 3' overhanging sequence.

The methods of the invention as exemplified herein can be performed using two or more site specific topoisomerases, wherein the first, second or other ds nucleotide sequence substrates correspondingly have, at or near a 3' terminus or 5' terminus of an end, a topoisomerase recognition site for one of the two or more topoisomerases. The use of two or more topoisomerases, and corresponding topoisomerase recognition sites, can facilitate the joining of the ds nucleotide sequences in a predetermined order, orientation, or combination thereof. Thus, it will be recognized that, where a method of the invention is exemplified using a topoisomerase, the method similarly can be performed using two or more topoisomerases. In some cases, reference is made to the use of at least one topoisomerase, and, unless indicated otherwise, the methods can be performed using one, two, three or more topoisomerases, provided the substrate ds nucleotide sequences contain the appropriate topoisomerase recognition sites. Similar considerations are relevant to topoisomerase-charged ds nucleotide sequence substrates, including that the topoisomerases can be the same or different.

The present invention provides methods for generating a ds recombinant nucleic acid molecule that is covalently linked in both strands. Such a method can be performed by contacting 1) a first ds nucleotide sequence having a first end and a second end, wherein the first ds nucleotide sequence has a topoisomerase recognition site at or near the 3' terminus and a topoisomerase recognition site at or near the 5' terminus of the first end or of the second end or of both ends; 2) at least a second ds nucleotide sequence having a first end and a second end; and 3) at least two (e.g., 2, 3, 4, 5, 6, 7, 8, 9, 10, etc.) site specific topoisomerases, under conditions such that all components are in contact and each of the topoisomerases can effect its activity. Upon cleavage of the termini of the substrate first ds nucleotides sequence by the topoisomerases, the 5' terminus or the 3' terminus of one or both of the first or second ends can comprise an overhanging sequence, or can be blunt ended, or a first end can contain an overhang and the second end can be blunt ended. Where present, an overhanging sequence of a first end will generally have sufficient complementarity to an overhanging sequence of a second (or other) end to allow for specific hybridization of the two ends to each other. Further, when the first and second ends are on different molecules, methods of the invention result in the two molecules becoming linked and when the first and second ends are on the same molecule, the methods result in the molecule becoming circularized.

The number of different topoisomerases useful in such an embodiment will depend, in part, on whether the first ds nucleotide sequence contains topoisomerase recognition sites at only the first end or the second end, or contains topoisomerase recognition sites at both ends, and further, where the ds nucleotide sequence contains topoisomerase recognition sites on both ends, whether the 3' recognition sites or the 5' recognition sites are different. In addition, the method can be performed such that one or more of the at least second ds nucleotide sequences also can contain a topoisomerase recognition site at or near the 3' terminus and/or a topoisomerase recognition site at or near the 5' terminus of the first end or of the second end or of both ends, wherein the topoisomerase recognition sites at or near the 3' terminus or the 5' terminus or both of the other ds nucleotide sequence can the same as or different from the topoisomerase recognition sites in the first ds nucleotide sequence. As such, the number of different topoisomerases further can depend on the number of different substrate ds nucleotide sequences being linked according to a method of the invention.

An advantage of performing a method of the invention using a site specific topoisomerase is that the first ds nucleotide sequence, the second ds nucleotide sequence, and one or more additional ds nucleotide sequences can be covalently linked, in one or both strands, in a predetermined directional orientation. An additional advantage is that a product comprising nucleotide sequences spanning the linkage site can be selected in vitro by performing an amplification reaction using a first primer that selectively hybridize to a sequence downstream of the linkage site and a second primer complementary to a sequence upstream of the linkage site, for example, amplification primers specific for the termini or sequences near the termini of a ds recombinant nucleic acid molecule covalently linked in both strands. A ds recombinant nucleic acid molecule, covalently linked in one or both strands, generated according to a method of the invention can be used directly in further procedures such as, for example, for transfecting a cell; as a template for performing amplification (e.g., PCR); in an in vitro transcription reaction; in a coupled transcription/translation reaction; for linkage to other nucleotide sequences using a restriction endonuclease site, which can be contained in a multiple cloning site; or for chromosomal integration via homologous recombination. Accordingly, a ds recombinant nucleic acid molecule generated according to a method of the invention can be useful, without further manipulation, for various purposes.

In an aspect of the invention, the first ds nucleotide sequences are derived from at least a first population of nucleic acid molecules, for example, from a cDNA library or a combinatorial library such as a combinatorial library of synthetic oligonucleotides, and the second ds nucleotide sequences are derived from at least a second population of ds nucleotide sequences. According to a method of the invention, linking of first ds nucleotide sequences with second ds nucleotide sequences provides a means to generate combinatorial populations of ds recombinant nucleic acid molecules that are covalently linked in one or both strands. In accordance with such a method, one or more target nucleic acid molecules also can be linked with the recombinant nucleic acid molecules of the population to produce additional populations. Such populations of combinatorial molecules can be further manipulated or analyzed, for example, by protein expression and screening for fusion proteins having desirable characteristics.

In one embodiment, a method of the invention is performed such that the first ds nucleotide sequence comprises an open reading frame, for example, an isolated cDNA or coding sequence or exon of a gene, and a second ds nucleotide sequence comprises a regulatory element such as a promoter, which can be operatively covalently linked to the 5' end of the coding sequence such that the coding sequence can be transcribed therefrom. A second ds nucleotide sequence also can comprise two or more regulatory elements, for example, a promoter, an internal ribosome entry site and an ATG initiator methionine codon, in operative linkage with each other, which can be operatively covalently linked to the 5' end of a first ds nucleotide sequence comprising a coding sequence according to a method of the invention. Such a method can further include contacting a third ds nucleotide sequence comprising, for example, a polyadenylation signal and/or a suppressible STOP codon, which can be operatively covalently linked to the 3' end of the coding sequence. Such a method can be useful for generating an expressible nucleic acid molecule, which can be transcribed, translated, or both as a functional unit. In addition, or alternatively, a ds nucleotide sequence encoding a detectable marker, for example, an epitope tag, can be operatively linked to a first or second (or other) ds nucleotide sequence according to a method of the invention. The generation of a ds recombinant nucleic acid molecule having a desired directional orientation of the nucleotide sequences in such a construct can be facilitated by including complementary 5' or 3' overhanging sequences at the termini of the ds nucleotide sequences to be covalently linked together by the topoisomerase.

In an embodiment, a method of the invention is performed such that at least the first ds nucleotide sequence or the at least second ds nucleotide sequence is one of a plurality of nucleotide sequences, for example, a cDNA library, a combinatorial library of nucleotide sequences, or a variegated population of nucleotide sequences. In another embodiment, a method of the invention includes further contacting a ds recombinant nucleic acid molecule, covalently linked in one or both strands, with a PCR primer pair, and amplifying all or a portion of the covalently linked ds recombinant nucleic acid molecule. In addition to generating a large amount of product, the amplification reaction can be selective for constructs comprising a desired covalently linked ds recombinant nucleic acid molecule, particularly where the ds nucleotide sequences to be covalently linked comprise complementary overhanging sequences. As such, a method of the invention provides an in vitro selection means that is suitable for high throughput analysis.

A method for generating a ds recombinant nucleic acid molecule covalently linked in both strands is exemplified by contacting 1) a first ds nucleotide sequence having a first end and a second end, wherein, at the first end, second end, or both ends, the first ds nucleotide sequence has a topoisomerase covalently bound to the 3' terminus ("topoisomerase-charged"); and 2) at least a second ds nucleotide sequence, which can, but need not, be charged with topoisomerase. Preferably, the topoisomerase-charged ds nucleotide sequence or sequences contain a 5' hydroxyl group at the ends having the bound topoisomerase, although 5' hydroxy groups also can be generated using a phosphatase. The methods of the invention can be performed using only a first ds nucleotide sequence and a second ds nucleotide sequence, or can include a third, fourth or more ds nucleotide sequences as desired, wherein each nucleotide sequence is as defined above. A first or second (or other) ds nucleotide sequence independently can have a topoisomerase covalently bound to a 3' terminus of one end or at both ends of the nucleotide sequence, and, unless indicated otherwise, the first and second (or other) ds nucleotide sequences can be the same or can be different.

Methods of the invention for generating a ds recombinant nucleic acid molecule covalently linked in both strands are further exemplified by contacting 1) a first ds nucleotide sequence having a first end and a second end, wherein, at the first end, second end, or both ends, the first ds nucleotide sequence has a topoisomerase covalently bound to a 5' terminus (i.e., a topoisomerase-charged 5' terminus); and 2) at least a second nucleotide sequence, which can, but need not, be charged with topoisomerase. The topoisomerase-charged ds nucleotide sequence or sequences can contain a 3' hydroxyl group at the ends containing the bound topoisomerase, or a 3' hydroxyl group can be generated using a phosphatase. As disclosed herein, such a method can be performed using only a first ds nucleotide sequence and a second ds nucleotide sequence, or can include a third, fourth or more ds nucleotide sequences as desired, wherein each nucleotide sequence is as defined, including comprising at least one topoisomerase-charged 5' terminus. A first or second (or other) ds nucleotide sequence independently can have a topoisomerase covalently bound to a 5' terminus of one end or of both ends of the ds nucleotide sequence, and, unless indicated otherwise, the first and second (or other) ds nucleotide sequences can be the same or can be different.

A method of the invention is additionally exemplified by contacting 1) a first ds nucleotide sequence having a first end and a second end, wherein, at the first end, second end, or both ends, the first ds nucleotide sequence has a first topoisomerase covalently bound to the 5' terminus and a second topoisomerase covalently bound to the 3' terminus of the first end, the second end, or both ends (i.e., one or both ends contain a topoisomerase-charged 5' terminus and a topoisomerase-charged 3' terminus); and 2) at least a second ds nucleotide sequence, which, preferably, has, or can be made to have, hydroxyl groups at the 5' terminus and 3' terminus of an end to be covalently linked to an end of the first ds nucleotide sequence containing the topoisomerases. The method also can be performed wherein either the 5' terminus or 3' terminus of the end containing a topoisomerase-charged 3' terminus or topoisomerase-charged 5' terminus, respectively, contains a topoisomerase recognition site, wherein the method further includes contacting the components with a topoisomerase that can effect its activity with respect to the topoisomerase recognition site. Such a method of the invention can be performed using only a first ds nucleotide sequence and a second ds nucleotide sequence, or can include a third, fourth or more ds nucleotide sequence as desired, wherein the ds nucleotide sequences are as defined for the first ds nucleotide sequence, the second ds nucleotide sequence, or a combination thereof. A first or second (or other) ds nucleotide sequence independently can, but need not, have one or more topoisomerases covalently bound to a 5' terminus, 3' terminus, or both 5' and 3' termini of the second end (i.e., the undefined end). Unless indicated otherwise, the first and second (or other) ds nucleotide sequences can be the same or can be different.

The present invention further relates to a method of generating a ds recombinant nucleic acid molecule covalently linked in both strands by 1) amplifying a portion of a first ds nucleotide sequence using a PCR primer pair, wherein at least one primer of the primer pair encodes a complement of a topoisomerase recognition site, thereby producing an amplified first ds nucleotide sequence having a first end and a second end, wherein the first end or second end or both has a topoisomerase recognition site at or near the 3' terminus; and 2) contacting a) the amplified first ds nucleotide sequence; b) at least a second ds nucleotide sequence having a first end and a second end, wherein the first end or second end or both has a topoisomerase recognition site, or cleavage product thereof, at or near the 3' terminus and has, or can be made to have, a hydroxyl group at the 5' terminus of the same end; and c) a site specific topoisomerase, under conditions such that the topoisomerase can cleave the end of the amplified first ds nucleotide sequence having a topoisomerase recognition site and the end (or ends) of the at least second ds nucleotide sequence having a topoisomerase recognition site, and can effect its ligating activity. The PCR primer that encodes a complement of a topoisomerase recognition site can have a hydroxyl group at its 5' terminus, or the amplified first ds nucleotide sequence generated using the primer can be contacted with a phosphatase to generate a hydroxyl group at its 5' terminus. The PCR primer encoding the complement of a topoisomerase recognition site also can comprise a nucleotide sequence at its 5' terminus such that, upon cleavage by a site specific topoisomerase of a first ds nucleotide sequence amplified using the primer, the ds nucleotide sequence contains a 5' overhanging sequence, which is complementary to a 5' overhang of a second (or other) ds nucleotide sequence to which the first ds nucleotide sequence is to be covalently linked according to a method of the invention.

The present invention also relates to a method of generating a ds recombinant nucleic acid molecule covalently linked in both strands by 1) amplifying a portion of a first ds nucleotide sequence using a PCR primer pair, wherein at least one primer of the primer pair encodes a topoisomerase recognition site, thereby producing an amplified first ds nucleotide sequence having a first end and a second end, wherein the first end, second end, or both ends have a topoisomerase recognition site at or near the 5' terminus; and 2) contacting a) the amplified first ds nucleotide sequence; b) at least a second ds nucleotide sequence having a first end and a second end, wherein the first end, second end, or both ends have a topoisomerase recognition site at or near the 5' terminus and have, or can be made to have, a hydroxyl group at the 3' terminus of the same end; and c) at least one site specific topoisomerase, under conditions such that the at least one topoisomerase can cleave the first and/or second end of the amplified first ds nucleotide sequence having a topoisomerase recognition site and the end (or ends) of the at least second ds nucleotide sequence having a topoisomerase recognition site, and can effect its ligating activity. The amplified first ds nucleotide sequence generally has a hydroxyl group at the 3' terminus of the end containing the topoisomerase recognition site, or can be modified to contain such a 3' hydroxyl group. The PCR primer encoding the topoisomerase recognition site can further comprise a nucleotide sequence at its 5' terminus, i.e., 5' to the topoisomerase recognition site, such that, upon cleavage of the amplified first ds nucleotide sequence by a site specific topoisomerase, the ds nucleotide sequence contains a 3' overhanging sequence, which is complementary to a 3' overhanging sequence of a second (or other) ds nucleotide sequence to which the first ds nucleotide sequence is to be covalently linked according to a method of the invention.

The present invention further relates to a method of generating a ds recombinant nucleic acid molecule covalently linked in both strands by 1) amplifying a portion of a first ds nucleotide sequence using a PCR primer pair, wherein at least one primer of the primer pair includes a topoisomerase recognition site and a nucleotide sequence complementary to a topoisomerase recognition site, thereby producing an amplified first ds nucleotide sequence having a first end and a second end, wherein the amplified first ds nucleotide sequence has a topoisomerase recognition site at or near the 5' terminus and a topoisomerase recognition site at or near the 3' terminus of the first end, second end, or both ends; and 2) contacting a) the amplified first ds nucleotide sequence; b) at least a second ds nucleotide sequence having a first end and a second end, wherein the second ds nucleotide sequence has, or can be made to have, a 5' hydroxyl group and a 3' hydroxyl group at the first end, second end, or both ends; and c) at least two site specific topoisomerases, under conditions such that i) at least one topoisomerase can cleave the topoisomerase recognition site at or near the 5' terminus of the first and/or second end of the amplified first ds nucleotide sequence, and can effect its ligating activity, and ii) at least one topoisomerase can cleave the topoisomerase recognition site at or near the 3' terminus of the end of the amplified first ds nucleotide sequence, and can effect its ligating activity. Accordingly, the present invention provides a ds nucleotide sequence containing, at one or both ends, a topoisomerase recognition site at or near the 5' terminus and a topoisomerase recognition site at or near the 3' terminus. In addition, the invention provides such a ds nucleotide sequence, which is topoisomerase-charged at the 5' terminus, the 3' terminus, or both termini.

The present invention further relates to an isolated oligonucleotide containing a recognition site of a type IA site specific topoisomerase and/or a nucleotide sequence complementary to a recognition site of a type IB site specific topoisomerase, such an oligonucleotide being useful, for example, as a primer for a primer extension reaction or as one of a primer pair for performing an amplification reaction such as PCR, as well as products generated by incubation with a topoisomerase. Such an oligonucleotide, which is referred to an oligonucleotide primer, can be one of a primer pair, which can be useful, for example, for generating a ds nucleic acid amplification product that contains, at one end, a topoisomerase recognition site (e.g., a type IA or type II topoisomerase recognition site) at or near the 5' terminus and, at the same end, a topoisomerase recognition site (e.g., a type IB topoisomerase recognition site) at or near the 3' terminus. Generally, the oligonucleotide primer is about 12 to 100 nucleotides in length, and usually about 15 to 50 nucleotides in length, particularly about 18 to 30 nucleotides in length, wherein, when present, the nucleotide sequence of the type IA topoisomerase recognition site and the nucleotide sequence complementary to the type IB topoisomerase recognition site can, but need not, be separated by at least one or a few (e.g., 1, 2, 3, 4, 5, 6, 7, 8, etc.) nucleotides.

An oligonucleotide primer of the invention can further contain a nucleotide sequence encoding (or complementary to) any other nucleotide sequence or peptide of interest, for example, one or more (e.g., 1, 2, 3, 4, 5, 6, 7, 8, etc.) restriction endonuclease recognition sites, a peptide tag, and, if desired, one or more additional type IA, type II or type IB topoisomerase recognition sites, thereby allowing selection of one or more convenient or readily available topoisomerases for practicing a method of the invention. The oligonucleotide primer can further comprise a nucleotide sequence at its 5' terminus, i.e., 5' to the topoisomerase recognition site (e.g., type IA or type II topoisomerase recognition site) or to the nucleotide sequence complementary to a type IB topoisomerase recognition site, such that, upon cleavage of the amplified first ds nucleotide sequence by a site specific topoisomerase, the ds nucleotide sequence contains a 3' or 5' overhanging sequence, respectively, which is complementary to a 3' or 5' overhanging sequence, respectively, of a second (or other) ds nucleotide sequence to which the first ds nucleotide sequence is to be covalently linked according to a method of the invention, or the oligonucleotide primer can be designed such that, upon cleavage of an amplified ds nucleotide sequence generated therefrom, a blunt end topoisomerase-charged ds nucleotide sequence is generated.

The present invention also provides a primer pair, which includes at least one oligonucleotide primer as defined above, wherein one of the primers is useful as a forward primer and the primer is useful as a reverse primer in an amplification reaction. The first and/or second primer in such a primer pair can, but need not, include a type IA topoisomerase recognition site, a nucleotide sequence complementary to a type IB topoisomerase recognition site, or both, and can include any other nucleotide sequence of interest. In one embodiment, the primer pair includes at least two oligonucleotide primers of the invention, wherein one oligonucleotide primer is useful as a forward primer and the second oligonucleotide primer is useful as a reverse primer, such a primer pair being useful, for example, for generating a ds nucleotide sequence amplification product having topoisomerase recognition sites at both termini of both ends, wherein the type IA or type IB or both topoisomerase recognition sites at the termini are the same or different. Accordingly, primer pairs of the invention include, for example, a first primer encoding a type IA topoisomerase recognition site and a second primer encoding a nucleotide sequence complementary to a type IB topoisomerase recognition site; a first primer encoding a type IA topoisomerase recognition site and a second primer encoding a type IA topoisomerase recognition site, which can be the same or different as that encoded by the first primer; a first primer encoding a nucleotide sequence complementary to a type IB topoisomerase recognition site and a second primer encoding a nucleotide sequence complementary to a type IB topoisomerase recognition site, which can be the same or different from that encoded by the first primer; a first primer encoding a type IA topoisomerase recognition site and a second primer encoding a type II recognition site or a nucleotide sequence complementary thereto; a first primer encoding a nucleotide sequence complementary to a type IB topoisomerase recognition site and a second primer encoding a type II topoisomerase recognition site or a nucleotide sequence complementary thereto; a first primer encoding a type II topoisomerase recognition site or a nucleotide sequence complementary thereto and a second primer encoding a type II topoisomerase recognition site or a nucleotide sequence complementary thereto, which is the same or different from the type II topoisomerase recognition site of the first primer. The present invention also provides kits containing one or more primer pairs of the invention, for example, one or more of the primer pairs exemplified above, or can contain three primers, for example, a first primer encoding a type IA topoisomerase recognition site, a second primer encoding a nucleotide sequence complementary to a type IB topoisomerase recognition site, and a third primer encoding a type II topoisomerase recognition site or a nucleotide sequence complementary thereto, such a kit allowing a convenient means to generate a primer extension or amplification product that can be covalently linked according to a method of the invention.

Accordingly, the present invention further relates to a ds nucleotide sequence, which has a first end and a second end, and which contains a topoisomerase recognition site (e.g., a type IA or type II topoisomerase recognition site) at or near the 5' terminus and a type IB topoisomerase recognition site at or near the 3' terminus of the first end, the second end, or of both ends. In addition, the present invention provides a ds nucleotide sequence as defined above, except wherein the ds nucleotide sequence is a topoisomerase-charged molecule, comprising a stably bound type IA topoisomerase or a type IB topoisomerase or both, at one or both ends, as desired.

In one embodiment, the first ds nucleotide sequence comprises or encodes an expressible nucleotide sequence such as a nucleotide sequence encoding a polypeptide, an antisense nucleotide sequence, a ribozyme, a tRNA (e.g., a suppressor tRNA), a triplexing nucleotide sequence or the like, and the second (or other) ds nucleotide sequence comprises a transcription regulatory element such as a promoter (e.g., a GAL4 promoter), an enhancer, a silencer, a translation start site, or a polyadenylation signal, or encodes a translation regulatory element such as an initiator methionine, a STOP codon, a cell compartmentalization domain, a homology domain, or the like, or a combination thereof in operative linkage. A second (or other) ds nucleotide sequence, which can be an amplified second (or other) ds nucleotide sequence prepared as for the amplified first ds nucleotide sequence, also can comprise a detectable label, for example, an enzyme, a substrate for an enzyme, a fluorescent compound, a luminescent compound, a chemiluminescent compound, a radionuclide, a paramagnetic compound, and biotin; or can include a tag, which can be an oligonucleotide tag or can be a peptide tag, for example, a polyhistidine tag, a V5 epitope, or a myc epitope.

In another embodiment, a method of the invention is performed using a first ds nucleotide sequence that encodes a polypeptide, or a domain thereof, and a second (or other) ds nucleotide sequence that encodes a transcription activation domain or a DNA binding domain. Such a method can be used to generate covalently linked ds recombinant nucleic acid molecules, covalently linked in one or both strands, that encode chimeric polypeptides useful for performing a two hybrid assay system, particularly a high throughput two hybrid assay. In still another embodiment, the first ds nucleotide sequences comprises a plurality of nucleotide sequences, which can be a cDNA library, a combinatorial library of nucleotide sequences, a variegated population of nucleotide sequences, or the like.

A method of the invention provides a means to generate a ds recombinant nucleic acid molecule, covalently linked in one or both strands, useful for site specific insertion into a target genomic DNA sequence. The target genomic DNA sequence can be any genomic sequence, particularly a gene, and preferably a gene for which some or all of the nucleotide sequence is known. The method can be performed utilizing two sets of amplification primer pairs such as PCR primer pairs and a ds nucleotide sequence. The ds nucleotide sequence has a first end and a second end and generally encodes a polypeptide, for example, a selectable marker, wherein the ds nucleotide sequence comprises a topoisomerase recognition site or cleavage product thereof at the 3' terminus of each end and, optionally, a hydroxyl group at the 5' terminus of each end, and wherein, preferably, the 5' termini comprise overhanging sequences, which are different from each other. Similarly, the ds nucleotide sequence can comprise a topoisomerase recognition site (or cleavage product thereof) at or near the 5' terminus of one or both ends and, optionally, a hydroxyl group at the 3' terminus of one or both end, and wherein one or both of the 3' termini can comprise overhanging sequences, which can be the same as or different from each other; or the 5' terminus and 3' terminus of one or both ends of the ds nucleotide sequence each can comprise a topoisomerase recognition site or cleavage product thereof (see FIGS. 4 and 5).

The two sets of PCR primer pairs generally are selected such that, in the presence of an appropriate DNA polymerase such as Taq polymerase and a template comprising the sequences to be amplified, the primers amplify portions of a genomic DNA sequence that are upstream (and adjacent to) and downstream (and adjacent to) of the target site for insertion of the polypeptide (e.g., selectable marker). The sets of PCR primer pairs also are designed such that the amplification products contain a topoisomerase recognition site at least at the end to be covalently linked in one or both strands to the selectable marker, including at or near the 5' terminus, the 3' terminus, or both termini, as appropriate for the particular method of the invention being practiced. As such, the first PCR primer pair can include, for example, 1) a first primer, which comprises, in an orientation from 5' to 3', a nucleotide sequence complementary to a 5' overhanging sequence of the end of the selectable marker to which the amplification product is to be covalently linked, a nucleotide sequence complementary to a topoisomerase recognition site, and a nucleotide sequence complementary to a 3' sequence of a target genomic DNA sequence; and 2) a second primer, which comprises a nucleotide sequence of the target genomic DNA upstream of the 3' sequence to which the first primer is complementary. The second PCR primer pair includes 1) a first primer, which comprises, from 5' to 3', a nucleotide sequence complementary to the 5' overhanging sequence of the end of the selectable marker to which it is to be covalently linked, a nucleotide sequence complementary to a topoisomerase recognition site, and a nucleotide sequence of a 5' sequence of a target genomic DNA sequence, wherein the 5' sequence of the target genomic DNA is downstream of the 3' sequence of the target genomic DNA to which the first primer of the first PCR primer pair is complementary; and 2) a second primer, which comprises a nucleotide sequence complementary to a 3' sequence of the target genomic DNA that is downstream of the 5' sequence of the target genomic DNA contained in the first primer.

Upon contact of the ds nucleotide sequence comprising the selectable marker, the PCR amplification products, and at least one topoisomerase, a ds recombinant nucleic acid molecule, covalently linked in one or both strands, is generated according to a method of the invention. The generated ds recombinant nucleic acid molecule is useful for performing homologous recombination in a genome, for example, to knock-out the function of a gene in a cell, or to confer a novel phenotype on the cell containing the generated ds recombinant nucleic acid molecule. The method can further be used to produce a transgenic non-human organism having the generated recombinant nucleic acid molecule stably maintained in its genome.

The present invention also relates to compositions prepared according to the methods of the invention, and to compositions useful for practicing the methods. Such compositions can include one or more reactants used in the methods of the invention and/or one or more ds recombinant nucleic acid molecules produced according to a method of the invention. Such compositions can include, for example, one or more topoisomerase-charge ds nucleotide sequences; one or more primers useful for preparing a ds nucleotide sequence containing a topoisomerase recognition site at one or both termini of one or both ends of an amplification product prepared using these primers; one or more topoisomerases; one or more substrate ds nucleotide sequences, including, for example, nucleotide sequences encoding tags, markers, regulatory elements, or the like; one or more ds recombinant nucleic acid molecules covalently linked in one or both strands, produced according to a method of the invention; one or more cells containing or useful for containing a ds nucleotide sequence, primer, or recombinant nucleic acid molecule as disclosed herein; one or more polymerases for performing a primer extension or amplification reaction; one or more reaction buffers; and the like. In one embodiment, a composition of the invention comprises two or more different topoisomerase-charged ds nucleotide sequences. The composition can further comprise at least one topoisomerase. A composition of the invention also can comprise a site specific topoisomerase and a ds recombinant nucleic acid molecule covalently linked in one or both strands, wherein the recombinant nucleic acid molecule contains at least one topoisomerase recognition site for the site specific topoisomerase in each strand. The topoisomerase recognition site in one strand can be any distance from a topoisomerase recognition site in the complementary strand, for example, wherein a topoisomerase recognition site in one strand is within about 100 nucleotides of a topoisomerase recognition site in the complementary strand, or wherein the recognition sites are within about 50 nucleotides of each other, or within about 20 nucleotides of each other, or less.

Methods of the invention also can be used to link at least one end of a double stranded nucleic acid molecule (e.g., DNA or RNA) to at least one end of a single stranded nucleic acid molecule (e.g., DNA or RNA). Furthermore, the methods of the invention can be used to link at least one end of a single stranded nucleic acid molecule (e.g., DNA or RNA) to at least one end of a second (or other) single stranded nucleic acid molecule (e.g., DNA or RNA). In appropriate circumstances, the methods of the invention can be used to circularize nucleic acid molecules, including to concatenate and circularize nucleic acid molecules. Thus, one or more ds nucleotide sequences disclosed herein as useful in an aspect or embodiment of the invention can be replaced with one or more single stranded nucleotide sequences. The invention further includes compositions used in such methods and nucleic acid molecules produced by such methods. Thus, for example, the invention includes single-stranded nucleic acid molecules to which a site-specific topoisomerase (e.g., a type IA topoisomerase, a type IB topoisomerase, a type II topoisomerase, etc.) is attached to the 5' or 3' terminus. Methods for joining single stranded nucleic acid molecules to other single stranded nucleic acid molecules are described, for example, in Internatl. Publ. No. WO 00/56878, which is incorporated herein by reference.

The present invention provides methods for joining DNA molecules to RNA molecules, as well as compositions used in such methods and nucleic acid molecules produced by such methods. Thus, nucleotide sequences of the invention can comprise, for example, DNA (e.g., cDNA, genomic DNA, plasmid DNA, synthetic DNA, etc.) or RNA (e.g., mRNA, rRNA, tRNA, synthetic RNA, ribozymes, etc.). Examples of such methods are set out, for example, in FIG. 8 and in Internatl. Publ. No. WO 98/56943, which is incorporated herein by reference.

The present invention also relates to a kit, which contains components that can be useful for practicing a method of the invention. A kit of the invention can contain, for example, one or more topoisomerase-charged ds nucleotide sequence substrates, which can include one or more control nucleotide sequences that can be useful, for example, to test the accuracy or fidelity of the components of the kit; one or more topoisomerases; one or more primers, which can comprise a topoisomerase recognition site, a nucleotide sequence complementary to a topoisomerase recognition site, or both; one or more cells, which can contain or be useful for containing a nucleotide sequence of the kit or a nucleic acid molecule generated using the kit; one or more reagents, polymers, buffers, or the like, for performing a method using the kit; instructions for performing a method using the kit, for example, instructions for covalently linking one strand of first nucleotide sequence to one strand of at least a second nucleotide sequence, either or both of which can be single stranded or double stranded nucleotide sequences, or instructions for covalently linking both strands of a first ds nucleotide sequence to both strands of at least a second ds nucleotide sequence; and the like.

In one aspect, a kit of the invention contains a ds nucleotide sequence having a first end and a second end and encoding a polypeptide, which can be expressed, for example, a selectable marker, wherein the ds nucleotide sequence comprises a topoisomerase recognition site or cleavage product thereof at the 3' terminus of one or both ends. Optionally, the ds nucleotide sequence contains a hydroxyl group at the 5' terminus of one or both of the other ends, preferably at the end containing the topoisomerase recognition site or that is topoisomerase-charged. In particular embodiments, one or both 5' termini comprise overhanging sequences, which can be the same or can be different from each other.

A kit of the invention also can contain a ds nucleotide sequence having a first end and a second end, and encoding a polypeptide to be expressed, for example, a selectable marker, wherein the ds nucleotide sequence comprises a topoisomerase recognition site or cleavage product thereof at the 5' terminus of one or both ends. Optionally, the ds nucleotide sequence contains a hydroxyl group at the 3' terminus of one or both ends, and preferably, one or both 3' termini comprise overhanging sequences, which can be the same or can be different from each other. In addition, a kit of the invention can contain a ds nucleotide sequence having a first end and a second end, and encoding a polypeptide to be expressed, for example, a selectable marker, wherein the ds nucleotide sequence comprises a topoisomerase recognition site or cleavage product thereof at the 5' terminus and the 3' terminus of one or both ends. As such, it should be recognized that a kit of the invention can include any of various combinations of such ds nucleotide sequences comprising one or more topoisomerase recognition sites or topoisomerase-charged ds nucleotide sequences, including ds nucleotide sequences having a topoisomerase recognition site at a terminus or both termini of one or both ends and that is topoisomerase-charged at one or more termini.

A kit of the invention also can contain a ds nucleotide sequence comprising a regulatory element or other nucleotide sequence, for example, a coding sequence, and a topoisomerase recognition site or cleavage product thereof at a 3' terminus of at least a first end and, optionally, a hydroxyl group at the 5' terminus of an end containing the recognition site; or comprising a topoisomerase recognition site or cleavage product thereof at a 5' terminus of at least a first end, and, optionally, a hydroxyl group at the 3' terminus of the end containing the recognition site; or comprising a topoisomerase recognition site at the 5' terminus and 3' terminus of at least a first end. Preferably, the kit contains a variety of upstream regulatory elements, a variety of downstream regulatory elements, a variety of elements useful detecting or identifying a molecule containing the element, and combinations thereof. For example, the kit can contain a variety of gene promoter elements, which are constitutively active or inducible in one or a few or many different types of cells, elements that permit or facilitate ribosome binding such as an internal ribosome entry site, an element encoding a Kozak sequence or an initiator methionine, or the like. In addition, or alternatively, the kit can contain a variety of downstream regulatory elements such a polyadenylation signal sequences, sequences that terminate transcription or translation, or the like; and also can contain enhancers, silencers, and the like. Similarly, the kit can contain elements encoding detectable markers such as epitope tags, or the like. Preferably, the kit contains a variety of such elements, each of which contains at least one topoisomerase recognition site. More preferably, the elements further contain an overhanging sequence such that they can be operatively covalently linked to each other or to a ds nucleotide sequence encoding a polypeptide such as a selectable marker according to a method of the invention.

Optionally, a kit of the invention can contain element specific primers, which can be used to amplify a construct containing one of the variety of elements included in the kit. Where the kit contains such primers, the ds nucleotide sequences comprising the regulatory or other element has a nucleotide sequence that can be specifically bound by the primer such that extension of the primer through and including the regulatory element can be effected. In particular, the kit can contain element specific forward and reverse primers, which can be combined to produce a primer pair useful for amplifying, for example, a recombinant nucleic acid molecule containing a particular 5' regulatory element and a particular 3' regulatory element of the kit. Such a primer pair can selectively amplify a desired functional ds recombinant nucleic acid molecule covalently linked in both strands generated according to a method of the invention, but does not amplify partial reaction products.

In another embodiment, a kit of the invention contains a first ds nucleotide sequence, which has a first end and a second end, contains a topoisomerase recognition site, or cleavage product thereof, at one or both 3' termini, and encodes a transcription activation domain; and a second ds nucleotide sequence, which has a first end and a second end, contains a topoisomerase recognition site, or cleavage product thereof, at one or both 3' termini, and encodes a DNA binding domain; or contains a first ds nucleotide sequence, which has a first end and a second end, contains a topoisomerase recognition site, or cleavage product thereof, at one or both 5' termini, and encodes a transcription activation domain; and a second ds nucleotide sequence, which has a first end and a second end, and optionally contains a topoisomerase recognition site, or cleavage product thereof, at one or both 5' termini, and encodes a DNA binding domain. A kit of the invention also can contain a first ds nucleotide sequence, which has a first end and a second end, and encodes a transcription activation domain, and a second ds nucleotide sequence, which has a first end and a second end, and encodes a DNA binding domain, wherein at least the first ds nucleotide sequence or the second ds nucleotide sequence contains a topoisomerase recognition site, or cleavage product thereof, at a 5' terminus and a 3' terminus of at least one end, and wherein the other ds nucleotide contains a 3' hydroxyl and 5' hydroxyl at the end to be covalently linked to the end of the ds nucleotide sequence comprising the recognition sites.

Such a kit is useful, for example, for generating a ds recombinant nucleic acid molecule covalently linked in both strands, or a ds recombinant nucleic acid molecule covalently linked in one strand, encoding chimeric polypeptides for performing a two hybrid assay. The kit can further contain a primer pair, which can amplify a nucleotide sequence to be operatively linked to the first or second ds nucleotide sequence, wherein at least one primer of the primer pair comprises a topoisomerase recognition site, a complement of a topoisomerase recognition site, or both. Preferably, an amplification product generated using such a primer pair contains, following cleavage by a site-specific topoisomerase, a 3' or 5' overhanging sequence that is complementary to the first or second ds nucleotide sequence to which it is to be covalently linked. Such a kit can facilitate the generation of recombinant polynucleotides that comprise a first or second nucleotide sequence of the kit and encode a chimeric polypeptide useful for performing a two hybrid assay.

In another embodiment, a kit of the invention contains a first ds nucleotide sequence having a first end and a second end, each end having a 5' terminus and a 3' terminus; and instructions for using a topoisomerase to covalently linking the 5' terminus and 3' terminus of at least one of the first end and the second end to a 5' terminus and a 3' terminus of a second ds nucleotide sequence. Such a kit also can contain a second (or more) ds nucleotide sequence, to which the first ds nucleotide sequence can be covalently linked in both strands according to the instructions. In addition, the kit can contain a topoisomerase, for example, a type IB topoisomerase such as a Vaccinia type IB topoisomerase. The first ds nucleotide sequence is such a kit can contain at least one topoisomerase recognition site at or near the 5' terminus or 3' terminus of the first end or second end or both ends, for example, a type IB topoisomerase recognition site at or near a 3' terminus of one or both ends; or can have a topoisomerase bound to at least one terminus of the first end or second or both ends, for example, a type IB topoisomerase bound to a 3' terminus of the first end or second end or both.

BRIEF DESCRIPTION OF THE FIGURES

In FIGS. 2A and 2B, one (FIG. 2B) or both (FIG. 2A) of the overhang sequences are palindromic in nature. Sequences are shown in conventional orientation, with the top strand in a 5' to 3' orientation from left to right, and the bottom strand in a 3' to 5' orientation from left to right. Number in parentheses above or below sequence indicates SEQ ID NO:.

FIG. 3A shows the amount of each construct used for transfection. A "p" preceding an amount or volume of reactant indicates plasmid form, "l" indicates linear form, and "PCR" indicates PCR amplification reaction mixture.

FIG. 3B shows the level of β-galactosidase activity ("LacZ activity") associated with each transfected sample. Increased LacZ activity is indicative of a positive interaction.

FIG. 5A shows a first ds nucleotide sequence having a topoisomerase linked to each of the 5' terminus and 3' terminus of one end, and further shows linkage of the first ds nucleotide sequence to a second ds nucleotide sequence.

FIG. 5B shows a first ds nucleotide sequence having a topoisomerase bound to the 3' terminus of one end, and a second ds nucleotide sequence having a topoisomerase bound to the 3' terminus of one end, and further shows a covalently linked ds recombinant nucleic acid molecule generated due to contacting the ends containing the topoisomerase-charged substrate ds nucleotide sequences.

FIG. 5C shows a first ds nucleotide sequence having a topoisomerase bound to the 5' terminus of one end, and a second ds nucleotide sequence having a topoisomerase bound to the 5' terminus of one end, and further shows a covalently linked ds recombinant nucleic acid molecule generated due to contacting the ends containing the topoisomerase-charged substrate ds nucleotide sequences.

FIG. 5D shows a ds nucleotide sequence having a topoisomerase linked to each of the 5' terminus and 3' terminus of both ends, and further shows linkage of the topoisomerase-charged ds nucleotide sequence to two ds nucleotide sequences, one at each end. The topoisomerases at each of the 5' termini and/or at each of the 3' termini can be the same or different.

DETAILED DESCRIPTION OF THE INVENTION

Figure 4:
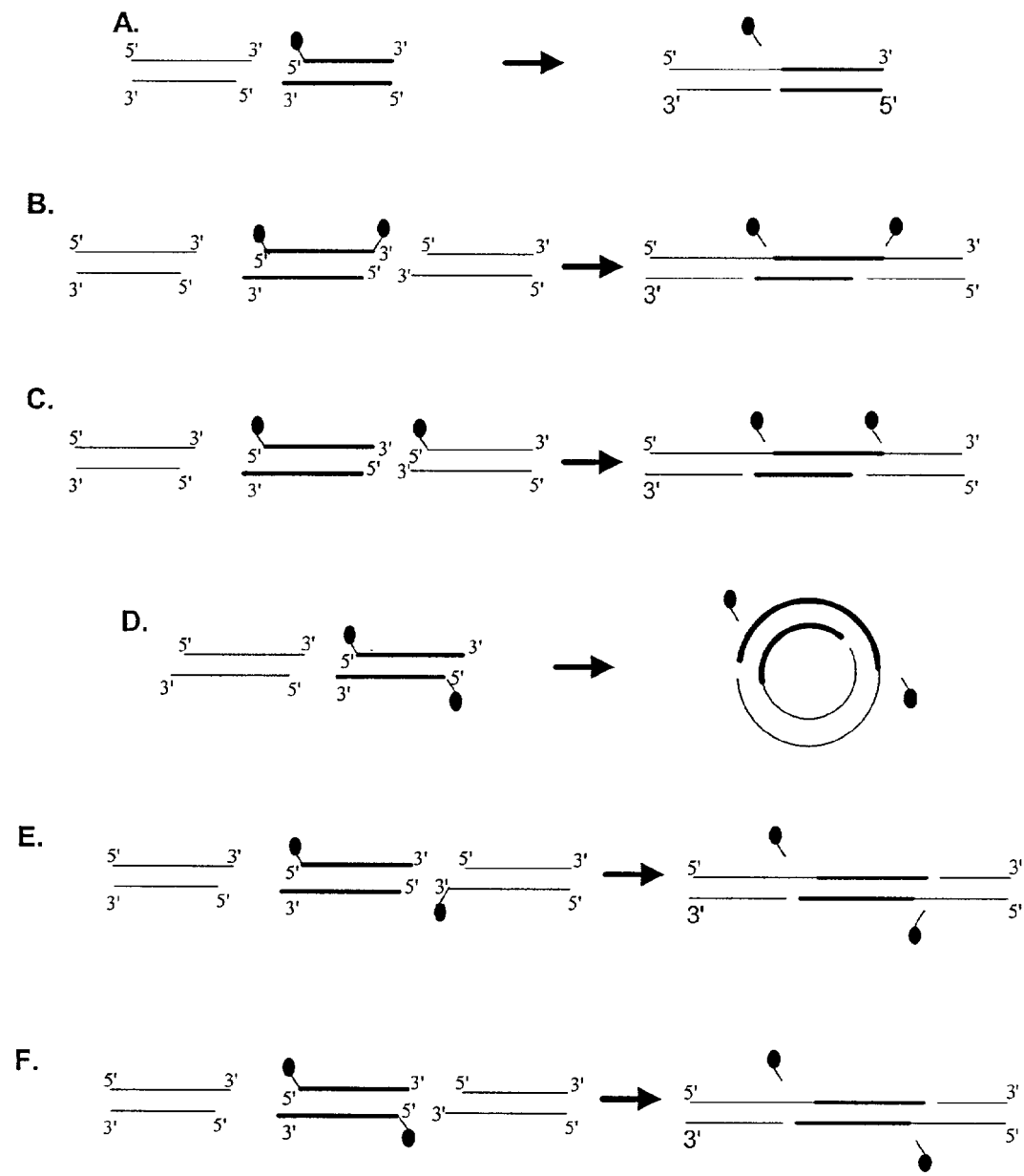
FIGS. 4A to 4F represent various embodiments of the composition and methods for generating a ds recombinant nucleic acid molecule covalently linked in one strand. Topoisomerase is shown as a solid circle, and is either attached to a terminus of a substrate ds nucleotide sequence or is released following a linking reaction.

The present invention relates to methods of using one or more topoisomerases to generate a recombinant nucleic acid molecule from two or more nucleotide sequences. In a first aspect, the invention provides a method for generating a ds recombinant nucleic acid molecule that is covalently linked in one strand. Such a method is directed to linking a first and at least a second nucleotide sequence with at least one (e.g., 1, 2, 3, 4, 5, 6, 7, 8, 9, 10, etc.) topoisomerase (e.g., a type IA, type IB, and/or type II topoisomerase) such that one strand, but not both strands, is covalently linked (see, for example, FIG. 4). In a second aspect, the invention provides a method for generating a ds recombinant nucleic acid molecule covalently linked in both strands. Such a method is directed to linking a first and at least a second nucleotide sequence with at least one topoisomerase, such that ligated ends are covalently linked in both strands (i.e., the ds recombinant nucleic acid molecule contain no nicks at the positions where ends were ligated; see, for example, FIG. 5). In a third aspect, the invention provides a method for generating a recombinant nucleic acid molecule covalently linked in one strand, wherein the substrate nucleotide sequences linked according to the method include at least one single stranded nucleotide sequence, which can be covalently linked to a second (or more) single stranded nucleotide sequence or to a ds nucleotide sequence (see, for example, FIG. 8).

Figure 9:
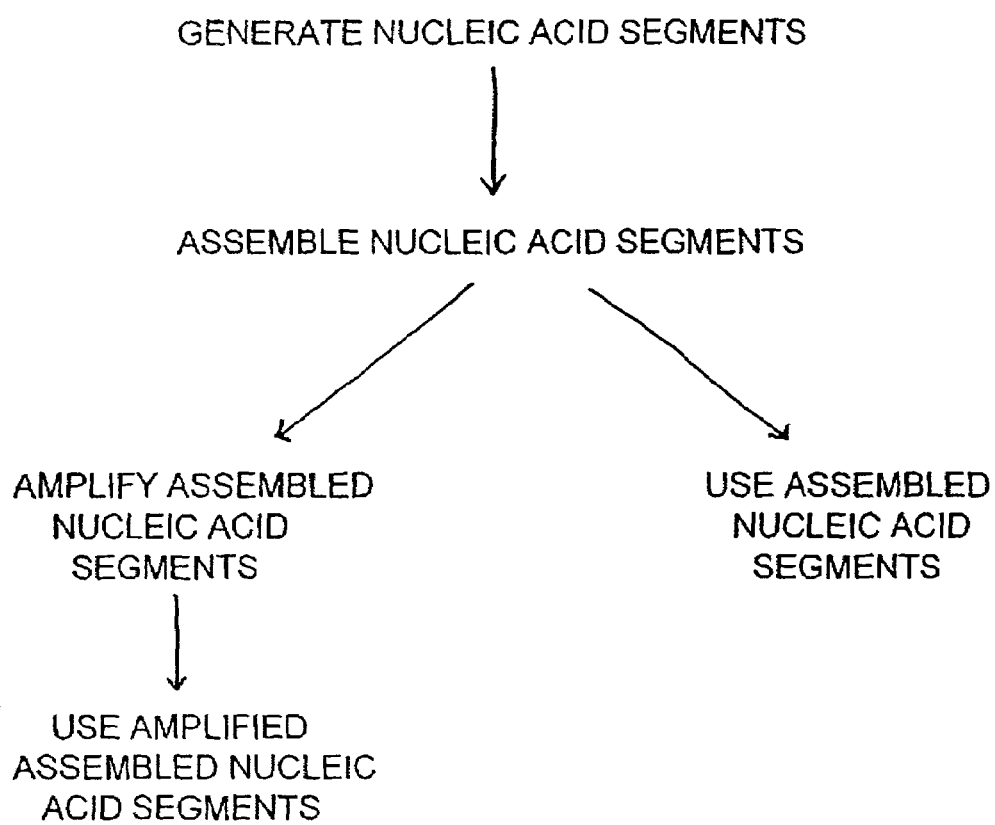
FIG. 9 provides a schematic outline exemplifying methods of the invention. In the first step, nucleotide sequences to be assembled are generated using an amplification method such as PCR. In the second step, the nucleotide sequences generated in the first step are assembled using a method of the invention (e.g., a method utilizing a topoisomerase to covalently link at least one strand of one nucleotide sequence to at least one strand of a second (or other) nucleotide sequence). In the third step as exemplified, assembled nucleic acid molecules (i.e., recombinant nucleic molecules) generated in the second step can be used directly or can be amplified, then used for any purpose as disclosed herein or otherwise desired.

Covalently linked recombinant nucleic acid molecules assembled using the methods of the invention can be used directly, or can be amplified, first, then used for any number of procedures as exemplified herein or otherwise known in the art. As disclosed herein, covalently linked recombinant nucleic acid molecules can be generated from nucleotide sequence in any of a number of ways (see, for example, FIG. 9). The nucleotide sequences useful in practicing the methods can be obtained using any of various well known methods, including, for example, by chemical synthesis, by isolation of restriction fragments or other cleavage products of genomic DNA, or by isolation of RNA, which can be used directly or converted to a cDNA using a reverse transcription method. Where the nucleotide sequences to be used according to a method of the invention lack one or more termini or regions suitable for generation of a recombinant nucleic acid molecule, the termini and/or regions can be added to the nucleotide sequence, for example, by an amplification reaction such as PCR, wherein one or both primers encode the desired sequence or a complement thereof (e.g., a topoisomerase recognition site, an overhanging sequence, etc) or by ligating one or more (e.g., one, two, three, four, etc.) adapter linkers, which can contain, for example, one or more topoisomerase recognition sites, or the nucleotide sequence can be modified using, for example, a method such as site directed mutagenesis to convert, for example, a sequence resembling a topoisomerase site to an actual topoisomerase recognition site. The nucleotide sequences having suitable termini and/or regions then can be assembled using methods of the invention as disclosed herein. The covalently linked recombinant nucleic acid molecule generated therefrom then can be amplified in vivo or in vitro, then used in any number of methods or processes, including those exemplified herein or otherwise known in the art. The covalently linked recombinant nucleic acid molecules also can be used directly for applications such as in vitro transcription/translation, recombinational cloning, or for transforming or transfecting cells. Accordingly, the present invention provides versatile methods for manipulating nucleotide sequences and for generating covalently linked recombinant nucleic acid molecules having desirable characteristic, and further provides compositions containing such nucleotide sequences and/or recombinant nucleic acid molecules, as well as methods of using the covalently linked recombinant nucleic acid molecules.

A method for generating a ds recombinant nucleic acid molecule covalently linked in one strand can be performed by contacting a first ds nucleotide sequence which has a site-specific topoisomerase recognition site (e.g., a type IA or a type II topoisomerase recognition site), or a cleavage product thereof, at a 5' or 3' terminus, with a second (or other) ds nucleotide sequence, and optionally, a topoisomerase (e.g., a type IA, type IB, and/or type II topoisomerase), such that the second nucleotide sequence can be covalently attached to the first nucleotide sequence. As disclosed herein, the methods of the invention can be performed using any number of nucleotide sequences, typically ds nucleotide sequences wherein at least one of the nucleotide sequences has a site-specific topoisomerase recognition site (e.g., a type IA, or type II topoisomerase), or cleavage product thereof, at one or both 5' termini (see, for example, FIGS. 4A–4F).

A method for generating a ds recombinant nucleic acid molecule covalently linked in both strands can be performed, for example, by contacting a first ds nucleotide sequence having a first end and a second end, wherein, at the first end or second end or both, the first ds nucleotide sequence has a topoisomerase recognition site (or cleavage product thereof) at or near the 3' terminus; at least a second ds nucleotide sequence having a first end and a second end, wherein, at the first end or second end or both, the at least second double stranded nucleotide sequence has a topoisomerase recognition site (or cleavage product thereof) at or near a 3' terminus; and at least one site specific topoisomerase (e.g., a type IA and/or a type IB topoisomerase), under conditions such that all components are in contact and the topoisomerase can effect its activity. A covalently linked ds recombinant nucleic acid generated according to a method of this aspect of the invention is characterized, in part, in that it does not contain a nick in either strand at the position where the ds nucleotide sequences are joined. In one embodiment, the method is performed by contacting a first ds nucleotide sequence and a second (or other) ds nucleotide sequence, each of which has a topoisomerase recognition site, or a cleavage product thereof, at the 3' termini or at the 5' termini of two ends to be covalently linked. In another embodiment, the method is performed by contacting a first ds nucleotide sequence having a topoisomerase recognition site, or cleavage product thereof, at the 5' terminus and the 3' terminus of at least one end, and a second (or other) ds nucleotide sequence having a 3' hydroxyl group and a 5' hydroxyl group at the end to be linked to the end of the first ds nucleotide sequence containing the recognition sites. As disclosed herein, the methods can be performed using any number of ds nucleotide sequences having various combinations of termini and ends (see, for example, FIGS. 5A–5D).

Topoisomerases are categorized as type I, including type IA and type IB topoisomerases, which cleave a single strand of a double stranded nucleic acid molecule, and type II topoisomerases (gyrases), which cleave both strands of a nucleic acid molecule. Type IA and IB topoisomerases cleave one strand of a ds nucleotide sequence. Cleavage of a ds nucleotide sequence by type IA topoisomerases generates a 5' phosphate and a 3' hydroxyl at the cleavage site, with the type IA topoisomerase covalently binding to the 5' terminus of a cleaved strand. In comparison, cleavage of a ds nucleotide sequence by type IB topoisomerases generates a 3' phosphate and a 5' hydroxyl at the cleavage site, with the type IB topoisomerase covalently binding to the 3' terminus of a cleaved strand. As disclosed herein, type I and type II topoisomerases, as well as catalytic domains and mutant forms thereof, are useful for generating ds recombinant nucleic acid molecules covalently linked in both strands according to a method of the invention.

Type IA topoisomerases include *E. coli* topoisomerase I, *E. coli* topoisomerase III, eukaryotic topoisomerase II, archeal reverse gyrase, yeast topoisomerase III, *Drosophila* topoisomerase III, human topoisomerase III, *Streptococcus pneumoniae* topoisomerase III, and the like, including other type IA topoisomerases (see Berger, *Biochim. Biophys. Acta* 1400:3–18, 1998; DiGate and Marians, *J. Biol. Chem.* 264:17924–17930, 1989; Kim and Wang, *J. Biol. Chem.* 267:17178–17185, 1992; Wilson et al., *J. Biol. Chem.* 275: 1533–1540, 2000; Hanai et al., *Proc. Natl. Acad. Sci., USA* 93:3653–3657, 1996, U.S. Pat. No. 6,277,620, each of which is incorporated herein by reference). *E. coli* topoisomerase III, which is a type IA topoisomerase that recognizes, binds to and cleaves the sequence 5'-GCAACTT-3', can be particularly useful in a method of the invention (Zhang et al., *J. Biol. Chem.* 270:23700–23705, 1995, which is incorporated herein by reference). A homolog, the traE protein of plasmid RP4, has been described by Li et al. (*J. Biol. Chem.* 272:19582–19587, 1997) and can also be used in the practice of the invention. A DNA-protein adduct is formed with the enzyme covalently binding to the 5'-thymidine residue, with cleavage occurring between the two thymidine residues.

Type IB topoisomerases include the nuclear type I topoisomerases present in all eukaryotic cells and those encoded by vaccinia and other cellular poxviruses (see Cheng et al., *Cell* 92:841–850, 1998, which is incorporated herein by reference). The eukaryotic type IB topoisomerases are exemplified by those expressed in yeast, *Drosophila* and mammalian cells, including human cells (see Caron and Wang, *Adv. Pharmacol.* 29B,:271–297, 1994; Gupta et al., *Biochim. Biophys. Acta* 1262:1–14, 1995, each of which is incorporated herein by reference; see, also, Berger, supra, 1998). Viral type IB topoisomerases are exemplified by those produced by the vertebrate poxviruses (vaccinia, Shope fibroma virus, ORF virus, fowlpox virus, and molluscum contagiosum virus), and the insect poxvirus (*Amsacta moorei* entomopoxvirus) (see Shuman, *Biochim. Biophys. Acta* 1400:321–337, 1998; Petersen et al., *Virology* 230:197–206, 1997; Shuman and Prescott, *Proc. Natl. Acad. Sci., USA* 84:7478–7482, 1987; Shuman, *J. Biol. Chem.* 269:32678–32684, 1994; U.S. Pat. No. 5,766,891; PCT/US95/16099; PCT/US98/12372, each of which is incorporated herein by reference; see, also, Cheng et al., supra, 1998).

Type II topoisomerases include, for example, bacterial gyrase, bacterial DNA topoisomerase IV, eukaryotic DNA topoisomerase II, and T-even phage encoded DNA topoisomerases (Roca and Wang, *Cell* 71:833–840, 1992; Wang, *J. Biol. Chem.* 266:6659–6662, 1991, each of which is incorporated herein by reference; Berger, supra, 1998). Like the type IB topoisomerases, the type II topoisomerases have both cleaving and ligating activities. In addition, like type IB topoisomerase, substrate ds nucleotide sequences can be prepared such that the type II topoisomerase can form a covalent linkage to one strand at a cleavage site. For example, calf thymus type II topoisomerase can cleave a substrate ds nucleotide sequence containing a 5' recessed topoisomerase recognition site positioned three nucleotides from the 5' end, resulting in dissociation of the three nucleotide sequence 5' to the cleavage site and covalent binding the of the topoisomerase to the 5' terminus of the ds nucleotide sequence (Andersen et al., supra, 1991). Furthermore, upon contacting such a type II topoisomerase-charged ds nucleotide sequence with a second nucleotide sequence containing a 3' hydroxyl group, the type II topoisomerase can ligate the sequences together, and then is released from the recombinant nucleic acid molecule. As such, type II topoisomerases also are useful for performing methods of the invention.

Structural analysis of topoisomerases indicates that the members of each particular topoisomerase families, including type IA, type IB and type II topoisomerases, share common structural features with other members of the family (Berger, supra, 1998). In addition, sequence analysis of various type IB topoisomerases indicates that the structures are highly conserved, particularly in the catalytic domain (Shuman, supra, 1998; Cheng et al., supra, 1998; Petersen et al., supra, 1997). For example, a domain comprising amino acids 81 to 314 of the 314 amino acid vaccinia topoisomerase shares substantial homology with other type IB topoisomerases, and the isolated domain has essentially the same activity as the full length topoisomerase, although the isolated domain has a slower turnover rate and lower binding affinity to the recognition site (see Shuman, supra, 1998; Cheng et al., supra, 1998). In addition, a mutant vaccinia topoisomerase, which is mutated in the amino terminal domain (at amino acid residues 70 and 72) displays identical properties as the full length topoisomerase (Cheng et al., supra, 1998). In fact, mutation analysis of vaccinia type IB topoisomerase reveals a large number of amino acid residues that can be mutated without affecting the activity of the topoisomerase, and has identified several amino acids that are required for activity (Shuman, supra, 1998). In view of the high homology shared among the vaccinia topoisomerase catalytic domain and the other type IB topoisomerases, and the detailed mutation analysis of vaccinia topoisomerase, it will be recognized that isolated catalytic domains of the type IB topoisomerases and type IB topoisomerases having various amino acid mutations can be used in the methods of the invention.

The various topoisomerases exhibit a range of sequence specificity. For example, type II topoisomerases can bind to a variety of sequences, but cleave at a highly specific recognition site (see Andersen et al., *J. Biol. Chem.* 266: 9203–9210, 1991, which is incorporated herein by reference). In comparison, the type IB topoisomerases include site specific topoisomerases, which bind to and cleave a specific nucleotide sequence ("topoisomerase recognition site"). Upon cleavage of a ds nucleotide sequence by a topoisomerase, for example, a type IB topoisomerase, the energy of the phosphodiester bond is conserved via the formation of a phosphotyrosyl linkage between a specific tyrosine residue in the topoisomerase and the 3' nucleotide of the topoisomerase recognition site. Where the topoisomerase cleavage site is near the 3' terminus of the nucleic acid molecule, the downstream sequence (3' to the cleavage site) can dissociate, leaving a nucleic acid molecule having the topoisomerase covalently bound to the newly generated 3' end (see FIG. 1).

A method of the invention for generating a ds recombinant nucleic acid molecule covalently linked in one strand, can be performed by contacting 1) a first ds nucleotide sequence having a first end and a second end, wherein the first ds nucleotide sequence has a site-specific topoisomerase recognition site (e.g., a type IA or a type II topoisomerase recognition site) at or near the 5' terminus of the first end or the second end or both; 2) at least a second ds nucleotide sequence that has, or can be made to have, a first end and a second end; and 3) at least one (e.g., 1, 2, 3, 4, 5, 6, 7, 8, 9, 10, etc.) site-specific topoisomerase (e.g., a type IA or a type IB topoisomerase recognition site), under conditions such that all components are in contact and the at least one topoisomerase can effect its activity. For example, the topoisomerase can be a type IA topoisomerase such as *E. coli* topoisomerase I, *E. coli* topoisomerase III, or a eukaryotic topoisomerase III. Upon cleavage of a ds nucleotide sequence, the topoisomerase preferably is stably bound to the 5' terminus. Preferably, upon cleavage by the topoisomerase, the cleaved ds nucleotide sequence comprises a 3' overhanging sequence.

A method of the invention for generating a ds recombinant nucleic acid molecule covalently linked in one strand can be performed such that any combination of ends are linked, and wherein one strand at the ends being linked is covalently linked and the other strand is not covalently linked, but contains a nick. For example, the first ds nucleotide sequence can comprise a coding sequence, wherein the ATG start codon is at or near the first end and a poly A signal is encoded at or near the second end; and a second ds nucleotide sequence can comprise a promoter element, which functions when positioned upstream of a coding sequence, and the first end is upstream of the second end, the method can be performed wherein a site-specific topoisomerase recognition site (e.g., a type IA or a type II topoisomerase recognition site) is at or near the 5' terminus of the first end of the first ds nucleotide sequence, and wherein the contacting is performed under conditions such that the topoisomerase (e.g., a type IA or a type II topoisomerase) can covalently link the 5' terminus of the first end of the first ds nucleotide sequence to the 3' terminus of the first end of the second ds nucleotide sequence, thereby generating a ds recombinant nucleic acid molecule, in which a polypeptide can be expressed from the coding sequence. Alternatively, the method can be performed wherein the topoisomerase recognition site (e.g., a type IA or a type II topoisomerase recognition site) is at or near the 5' terminus of the second end of the first ds nucleotide sequence, and wherein the contacting is performed under conditions such that the topoisomerase (e.g., a type IA or a type II topoisomerase recognition site) can covalently link the 5' terminus of the second end of the first ds nucleotide sequence to the 3' terminus of the first end of the second ds nucleotide sequence, thereby generating a ds recombinant nucleic acid molecule from which an antisense molecule can be expressed.

As another example using the first ds nucleotide sequence and second ds nucleotide sequence described above, the method can be performed, wherein the topoisomerase recognition site (e.g., a type IA or a type II topoisomerase recognition site) is at or near the 5' terminus of each of the first end and the second end of the first ds nucleotide sequence, and wherein the contacting is performed under conditions such that the type IA topoisomerase can covalently link the 5' terminus of the first end of the first ds nucleotide sequence to the 3' terminus of the first end of the second ds nucleotide sequence, and the 5' terminus of the second end of the first ds nucleotide sequence to the 3' terminus of the second end of the second ds nucleotide sequence. As such, the ds recombinant nucleic acid molecule generated by the method is circularized, and includes a nick in each strand opposite the location where a strand was covalently linked by a topoisomerase (e.g., a type IA or a type II topoisomerase). Furthermore, the promoter of the second ds nucleotide sequence can initiate expression of the first ds nucleotide sequence. In one embodiment, the circularized ds recombinant nucleic acid molecule comprises a vector.

As another example using the first ds nucleotide sequence and second ds nucleotide sequence described above, the method can be performed, wherein the topoisomerase recognition site (e.g., a type IA or a type II topoisomerase recognition site) is at or near the 5' terminus of each of the first end and the second end of the first ds nucleotide sequence, and wherein the contacting is performed under conditions such that the topoisomerase (e.g., a type IA or a type II topoisomerase) can covalently link the 5' terminus of the first end of the first ds nucleotide sequence to the 3' terminus of the second end of the second ds nucleotide sequence, and the 5' terminus of the second end of the first ds nucleotide sequence to the 3' terminus of the first end of the second ds nucleotide sequence. As such, the ds recombinant nucleic acid molecule generated by the method is circularized, and includes a nick in each strand opposite the location where a strand was covalently linked by topoisomerase (e.g., a type IA or a type II topoisomerase recognition site). Furthermore, the promoter of the second ds nucleotide sequence can initiate expression of an antisense sequence. In one embodiment, the circularized ds recombinant nucleic acid molecule comprises a vector.

As disclosed herein, a method of generating a ds recombinant nucleic acid molecule covalently linked in one strand, involving a first ds nucleotide sequence and at least a second ds nucleotide sequence, can further include a step for amplifying the ds recombinant nucleic acid molecule covalently linked in one strand. The amplification reaction can be carried out by contacting the ds recombinant nucleic acid molecule with an amplification reaction primer pair, wherein a first primer of the pair is capable of binding to the covalently linked strand, at or near one end of the first or second ds nucleotide sequence, and priming an amplification reaction toward the other ds nucleotide sequence to generate a first extension product that is identical in nucleotide sequence to the nicked strand of the ds recombinant nucleic acid molecule; and the second primer of the pair is capable of binding to the first extension product, typically at or near the 3' terminus, and, in the presence of the first primer, can generate an amplification product using the covalently linked strand and the extension product (or extension products generated therefrom) as templates. For example, the method can be performed such that the type IA topoisomerase recognition site is at or near a first end of the first ds nucleotide sequence, and the method further includes contacting the ds recombinant nucleic acid molecule with an amplification reaction primer pair, wherein a forward primer is capable of binding at or near the second end of the first ds nucleotide sequence, and wherein a reverse primer is capable of binding to a nucleotide sequence complementary to at least a portion of the second end of the second ds nucleotide sequence; and amplifying the ds recombinant nucleic acid molecule. The first ds nucleotide sequence can include a coding region and the second ds nucleotide sequence can include a regulatory element.

A method of generating a ds recombinant nucleic acid molecule covalently linked in one strand also can be performed by contacting 1) a first ds nucleotide sequence having a first end and a second end, wherein the first ds nucleotide sequence has a site-specific topoisomerase recognition site (e.g., a type IA or a type II topoisomerase recognition site) at or near the 5' terminus of the first end or the second end or both; 2) at least a second ds nucleotide sequence that has, or can be made to have, a first end and a second end; 3) at least a third ds nucleotide sequence which has, or can be made to have, a first end and a second end, each end further comprising a 5' terminus and a 3' terminus; and 4) at least one (e.g., 1, 2, 3, 4, 5, 6, 7, 8, 9, 10, etc.) site-specific topoisomerase (e.g., a type IA or a type II topoisomerase recognition site), under conditions such that all components are in contact and the at least one topoisomerase can effect its activity. For example, the topoisomerase can be a type IA topoisomerase such as E. coli topoisomerase I, E. coli topoisomerase III, or a eukaryotic topoisomerase III. Upon cleavage of a ds nucleotide sequence, the topoisomerase preferably is stably bound to the 5' terminus. Preferably, upon cleavage by the topoisomerase, the cleaved ds nucleotide sequence comprises a 3' overhanging sequence.

A method of the invention for generating a ds recombinant nucleic acid molecule covalently linked in one strand, involving a first ds nucleotide sequence that contains a site-specific topoisomerase recognition site (e.g., a type IA or a type IB topoisomerase recognition site), or cleavage product thereof, at least a second ds nucleotide sequence, and at least a third ds nucleotide sequence can be performed such that any combination of ends are linked, and one strand at the ends being linked is covalently linked and one strand is nicked. According to this embodiment, any of the ends can contain a type IA, type II, or type IB topoisomerase recognition site, or can comprise a cleavage product thereof, provided that the first ds recombinant nucleotide molecule contains a topoisomerase recognition site (e.g., a type IA or a type II topoisomerase recognition site) at or near a 5' terminus, or a cleavage product thereof, and only one topoisomerase or topoisomerase recognition site is present at the ends that are to be linked. For example, where the first ds nucleotide sequence comprises a site-specific type IA topoisomerase recognition site at or near each of the first end and the second end, the method further can include contacting the first ds nucleotide sequence and the second ds nucleotide sequence with at least a third ds nucleotide sequence which has, or can be made to have, a first end and a second end, each end further comprising a 5' terminus and a 3' terminus, under conditions such that the topoisomerase (e.g., a type IA or a type II topoisomerase) can covalently link the 5' terminus of the first end of the first ds nucleotide sequence with the 3' terminus of the first end of the second nucleotide sequence, and the 5' terminus of the second end of the first ds nucleotide sequence with the 3' terminus of the first end of the third nucleotide sequence. It will be recognized that other combinations of ends and topoisomerase recognition sites, or cleavage products thereof, can be used to perform such a method of the invention.

A method of the invention also can be performed by contacting a first ds nucleotide sequence and a second ds nucleotide sequence with at least a third ds nucleotide sequence, which comprises a first end and a second end, each end further comprising a 5' terminus and a 3' terminus, wherein the third ds nucleotide sequence comprises a type IB topoisomerase recognition site at or near the 3' terminus of said first end, or said second end, or both said first end and said second end; and at least one (e.g., 1, 2, 3, 4, 5, 6, 7, 8, 9, 10, etc.) type IB topoisomerase under conditions such that the type IB topoisomerase can covalently link the 3' terminus of the first end or second end of the third ds nucleotide sequence to the 5' terminus of the first end or second end of the second ds nucleotide sequence. In such a method, where the third ds nucleotide sequence comprises a type IB topoisomerase recognition site at or near the 3' terminus of the first end, the contacting can be performed under conditions such that the type IB topoisomerase can covalently link the 3' terminus of the first end of the third ds nucleotide sequence to the 5' terminus of the first end of the second ds nucleotide sequence. It will be recognized that other combinations of ends and topoisomerase recognition sites, or cleavage products thereof, can be used to perform such a method of the invention.

In another embodiment, a method for generating a ds recombinant nucleic acid molecule covalently linked in one strand can be performed by contacting 1) a first ds nucleotide sequence having a first end and a second end, wherein the first ds nucleotide sequence has a site-specific topoisomerase recognition site (e.g., a type IA or a type II topoisomerase recognition site) at or near the 5' terminus of an end and a type IB topoisomerase recognition site at or near the 3' terminus of the other end; 2) at least a second ds nucleotide sequence that has, or can be made to have, a first end and a second end; 3) at least one (e.g., 1, 2, 3, 4, 5, 6, 7, 8, 9, 10, etc.) site-specific topoisomerase (e.g., a type IA or a type II topoisomerase); and 4) at least one (e.g., 1, 2, 3, 4, 5, 6, 7, 8, 9, 10, etc.) type IB topoisomerase under conditions such that all components are in contact and the at least one topoisomerase can effect its activity. For example, the topoisomerase, for which a recognition site is at or near the 5' terminus, can be a type IA topoisomerase such as E. coli topoisomerase I, E. coli topoisomerase III, or a eukaryotic topoisomerase III. Upon cleavage of a ds nucleotide sequence, the type IA topoisomerase preferably is stably bound to the 5' terminus, and the type IB topoisomerase preferably is stably bound at the 3' terminus. Preferably, upon cleavage by the topoisomerases, the cleaved ds nucleotide sequence comprises a 3' overhanging sequence and a 5' overhanging sequence. The method can further include contacting the ds recombinant nucleic acid molecule with a DNA ligase, thereby generating a ds recombinant nucleic acid molecule covalently linked in both strands.

A method of generating a ds recombinant nucleic acid molecule covalently linked in one strand by contacting a first ds nucleotide sequence, a second ds nucleotide sequence, and at least a third ds nucleotide sequence, can further include a step for amplifying the ds recombinant nucleic acid molecule, particularly the covalently linked strand. The amplification can be carried out by contacting the ds recombinant nucleic acid molecule with an amplification reaction primer pair, wherein a first primer of the pair can bind selectively to the covalently linked strand at or near one end of the first or second ds nucleotide sequence and prime an amplification reaction toward the other ds nucleotide sequence to generate a first extension product that is complementary to the covalently-linked strand; and the second primer of the pair can bind selectively to the first extension product, typically at or near the 3' terminus, and, in the presence of the first primer, can generate an amplification product using the covalently linked strand and the extension product (or extension products derived therefrom) as templates. The method can be performed such that the topoisomerase recognition site (e.g., a type IA or a type IB topoisomerase recognition site) is at or near the first end of the first ds nucleotide sequence, and can further include contacting the ds recombinant nucleic acid molecule with an amplification reaction primer pair, wherein a forward primer is capable of binding to a nucleotide sequence at or near the second end of the first ds nucleotide sequence and wherein a reverse primer is capable of binding to a nucleotide sequence complementary to at least a portion of the third ds nucleotide sequence; and amplifying the ds recombinant nucleic acid molecule. The first ds nucleotide sequence can include a coding region and the third ds nucleotide sequence can include a regulatory element. Furthermore, the ends being linked can contain complementary overhanging sequences.

Representative embodiments of the disclosed methods for generating a ds recombinant nucleic acid molecule covalently linked in one strand are illustrated in FIGS. 4A–4F. In FIG. 4A, one of the ds nucleotide sequences has a topoisomerase attached to the 5' terminus of one end such that, when this molecule, which has a 3' overhang, is contacted with a second ds nucleotide sequence having a substantially complementary 3' overhang, under suitable conditions, the nucleotides comprising the 3' overhangs can hybridize and the topoisomerases can catalyze ligation. FIG. 4B shows a first ds nucleotide sequence having topoisomerase molecules linked to the 5' terminus and 3' terminus of two different ends of one nucleotide sequence, and further shows linkage of the first ds nucleotide sequence to two other nucleotide sequences to generate a nucleic acid molecule which has one strand without any nicks and another strand with two nicks. FIG. 4C shows a first ds nucleotide sequence having a topoisomerase molecule linked to the 5' terminus of one end and a second ds nucleotide sequence having a topoisomerase molecule linked to the 5' terminus of one end, and further shows linkage of the first and second ds nucleotide sequence to one other nucleotide sequence to generate a nucleic acid molecule which has one strand without any nicks and another strand with two nicks. In FIG. 4D, one of the ds nucleotide sequences to be linked has site-specific type IA topoisomerases attached to the 5' terminus of both ends such that, when the nucleotide sequences are contacted the complementary 3' overhangs can hybridize and the topoisomerases catalyze ligation. FIG. 4E shows another example of linking three ds nucleotide sequences together, using one ds nucleotide sequence that is topoisomerase-charged with a type IA topoisomerase at a 5' terminus and another ds nucleotide sequence that is topoisomerase-charged with a type IB topoisomerase at a 3' terminus of the opposite strand to be linked, such that when the nucleotide sequences are contacted the complementary 3' overhangs can hybridize and the topoisomerases catalyze ligation. FIG. 4F illustrates another example of linking three ds nucleotide sequences together, in this case using one ds nucleotide sequence that is topoisomerase-charged with a topoisomerase (e.g., a type IA or a type II topoisomerase) at a 5' terminus and with a type IB topoisomerase at a 3' terminus of the opposite strand, such that when the nucleotide sequences are contacted under suitable conditions, the complementary 3' overhangs can hybridize and the topoisomerases catalyze ligation.

The examples set forth in FIGS. 4A–4F show the ends of the ds nucleotide sequences opposite those being linked as having blunt ends, and shows the being linked as having 3' overhanging sequences. However, the substrate ds nucleotide sequences can have any ends and overhangs as desired, including both ends being blunt and/or complementary, or combinations thereof, such that the ends can be ligated to each other, for example, to form circular molecules or to other nucleic acid molecules having an appropriate end. Thus, one or more of the blunt ends as shown in FIGS. 4A–4F can be substituted with a nucleotide sequence comprising a 5' overhang or a 3' overhang, either of which can constitute a single nucleotide such as a thymidine residue or multiple nucleotides (e.g., two, three, four, five, six, seven, eight, nine, ten, eleven, twelve, thirteen, fourteen, fifteen, etc. nucleotides), which can be the same or different. In certain embodiments of the disclosed methods, a first ds nucleotide sequence contains a blunt end to be linked, and a second ds nucleotide sequence contains an overhang at the end which is to be linked by a site-specific topoisomerase (e.g., a type IA or a type IB topoisomerase), wherein the overhang includes a sequence complementary to that comprising the blunt end, thereby facilitating strand invasion as a means to properly position the ends for the linking reaction.

As exemplified in FIGS. 4A–4C, the ds recombinant nucleic acid molecule generated using the methods of this aspect of the invention include those in which one strand (not both strands) is covalently linked at the ends to be linked (i.e. ds recombinant nucleic acid molecules generated using these methods contain a nick at each position where two ends were joined). These embodiments are particularly advantageous in that a polymerase can be used to replicate the ds recombinant nucleic acid molecule by initially replicating the covalently linked strand. For example, a thermostable polymerase such as a polymerase useful for performing an amplification reaction such as PCR can be used to replicate the covalently strand, whereas the strand containing the nick does not provide a suitable template for replication.

Figure 5:
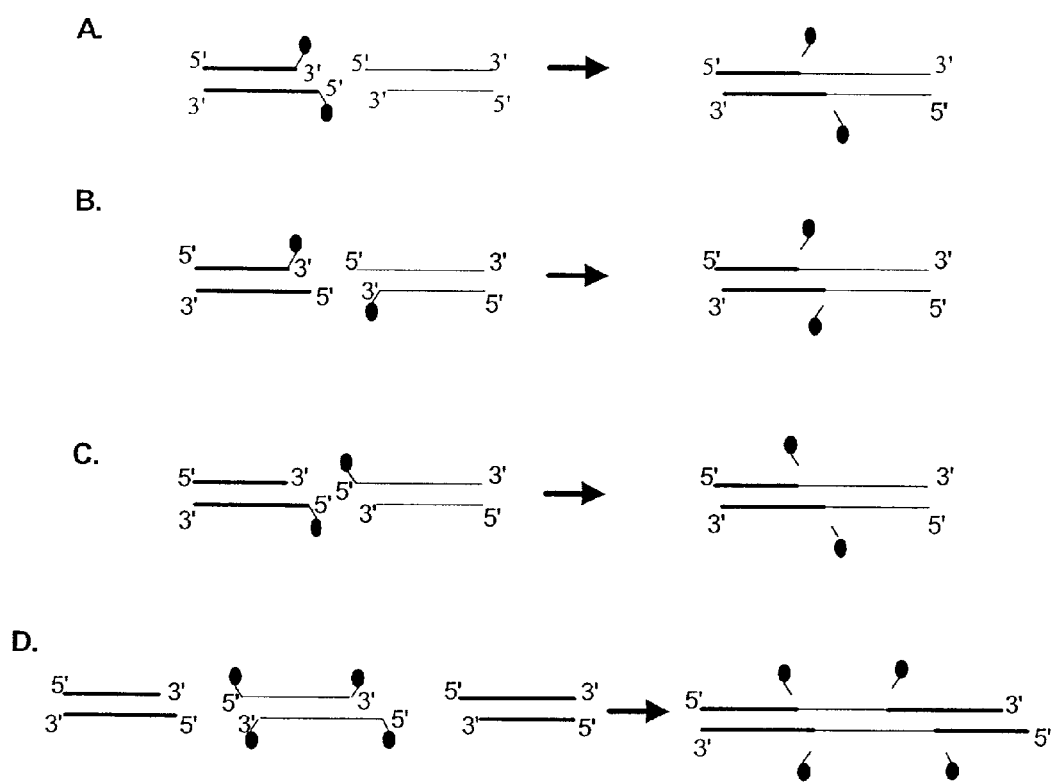
FIGS. 5A to 5D illustrate various embodiments of compositions and methods of the invention for generating a covalently linked ds recombinant nucleic acid molecule. Topoisomerase is shown as a solid circle, and is either attached to a terminus of a substrate ds nucleotide sequence or is released following a linking reaction. As illustrated, the substrate ds nucleotide sequences have 5' overhangs, although they similarly can have 3' overhangs or can be blunt ended. In addition, while the illustrated ds nucleotide sequences are shown having the topoisomerases bound thereto (topoisomerase-charged), one or more of the termini shown as having a topoisomerase bound thereto also can have a topoisomerase recognition site (i.e., one or more termini containing a topoisomerase recognition site), in which case the joining reaction would further require addition of one or more site specific topoisomerases, as appropriate.

The present invention also provides methods of covalently ligating the ends of two different ds nucleotide sequences or two ends of the same ds nucleotide sequence, such that the product generated is ligated in both strands and, therefore, does not contain a nick. Representative embodiments of this aspect of the invention are illustrated in FIG. 5. For example, in FIG. 5A, one of the ds nucleotide sequences has topoisomerase molecules attached to the 3' terminus and the 5' terminus of one end such that, when this molecule, which has a 5' overhang, is contacted with a second ds nucleotide sequence having a substantially complementary 5' overhang, under suitable conditions, the nucleotides comprising the 5' overhangs can hybridize and the topoisomerases can catalyze ligation of both strands of the ds nucleotide sequences. In FIG. 5B, each end of the ds nucleotide sequences to be linked has a topoisomerase molecule attached to the 3' terminus such that, when the nucleotide sequences are contacted under suitable conditions, nucleotides comprising the 5' overhangs can hybridize and the topoisomerases catalyze ligation (compare FIG. 5C, in which each of the ds nucleotide sequences to be linked has a topoisomerase attached to the 5' termini of the ends to be linked). FIG. 5D illustrates linking three ds nucleotide sequences together via a ds nucleotide sequence that is topoisomerase-charged at both termini of both ends. Similarly to FIG. 4, the examples set forth in FIGS. 5A–5D show the ends of the ds nucleotide sequences that are not being linked as having blunt ends. As discussed with respect to FIG. 4, however, the substrate ds nucleotide sequences utilized in methods as exemplified in FIG. 5 can have any ends as desired, including topoisomerase-charged ends, such that the ends can be ligated to each other, for example, to form circular molecules or to other nucleic acid molecules having an appropriate end, blunt ends, 5' overhangs, 3' overhangs, and the like, as desired.

A covalently bound topoisomerase, in addition to catalyzing a ligation reaction, also can catalyze the reverse reaction, for example, religation of the 3' nucleotide of the recognition sequence, to which the type IB topoisomerase is linked through the phosphotyrosyl bond, and the nucleotide sequence that, prior to cleavage, comprised the 5' terminus of the ds nucleotide sequence, and which, following cleavage, contains a free 5' hydroxy group. As such, methods have been developed for using a type IB topoisomerase to produce recombinant nucleic acid molecules. For example, cloning vectors containing a bound type IB topoisomerase have been developed and are commercially available (Invitrogen Corp., La Jolla Calif.). Such cloning vectors, when linearized, contain a covalently bound type IB topoisomerase at each 3' end ("topoisomerase-charged"). Nucleotide sequences such as those comprising a cDNA library, or restriction fragments, or sheared genomic DNA sequences that are to be cloned into such a vector are treated, for example, with a phosphatase to produce 5' hydroxyl termini, then are added to the linearized topoisomerase-charged vector under conditions that allow the topoisomerase to ligate the nucleotide sequences at the 5' terminus containing the hydroxyl group and the 3' terminus of the vector that contains the covalently bound topoisomerase. A nucleotide sequence such as a PCR amplification product, which is generated containing 5' hydroxyl ends, can be cloned into a topoisomerase-charged vector in a rapid joining reaction (approximately 5 minutes at room temperature). The rapid joining and broad temperature range inherent to the topoisomerase joining reaction makes the use of topoisomerase-charged vectors ideal for high throughput applications, which generally are performed using automated systems.

Type II topoisomerases have not generally been used for generating recombinant nucleic acid molecules or cloning procedures, whereas type IB topoisomerases, as indicated above, are used in a variety of procedures. As disclosed herein, type IA topoisomerases can be used in a variety of procedures similar to those described for the type IB topoisomerases. However, previously described methods of using type IB topoisomerases to ligate two or more nucleotide sequences have suffered from the disadvantage that the bound topoisomerase only effects the joining of the 3' end of the strand to which it is attached and a second strand containing a 5' hydroxyl group. Since the topoisomerase cannot ligate the complementary strands, the nucleic acid molecules that are generated contain nicks. While the presence of such nicks does not prevent the use of the recombinant molecules for transfection of a host cells, as the nicks generally are resolved intracellularly, the presence of such nicks in double stranded nucleic acid molecules significantly limits direct use of the recombinant molecules. For example, a strand of a nucleic acid molecule containing a nick cannot be amplified by PCR because the primer extension reaction terminates at the nick. Thus, nucleic acid constructs prepared using a topoisomerase according to previously described methods generally must be further treated, for example, with a DNA ligase, to obtain a ds recombinant nucleic acid molecule that is covalently linked in both strands and, therefore, useful for subsequent manipulations such as PCR.

Previously described methods for preparing nucleic acid constructs also generally required numerous steps, particularly where more than two nucleotide sequences are to be ligated, and even more so where the sequences must be ligated in a predetermined orientation. For example, the nucleotide sequences to be linked generally are ligated sequentially to produce intermediate constructs, each of which must be cloned, amplified in a host cell, isolated, and characterized. The constructs containing the correct sequences then must be isolated in a sufficient quantity and form such that the next nucleotide sequence can be ligated, and the process of cloning, amplifying, isolating and characterizing performed again to identify the proper construct. Clearly, as the number of different nucleotide sequences to be joined increases, so do the number of essentially repetitive procedures that must be performed, thus resulting in an expensive, laborious and lengthy process.

Figure 1A:
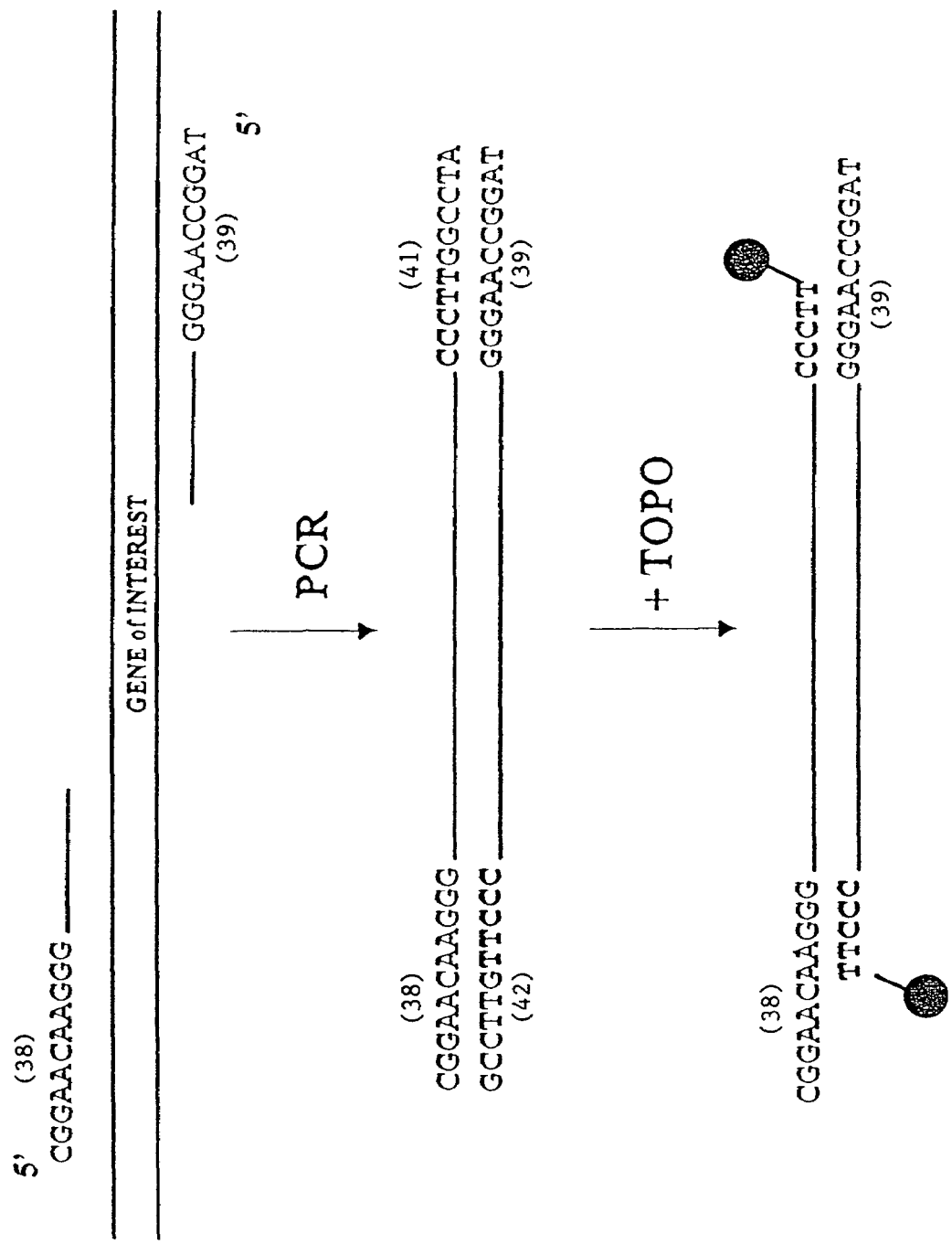
FIGS. 1A and 1B depict generating a covalently linked double stranded nucleotide sequence containing an element on each end according to a method of the invention. "PCR" indicates polymerase chain reaction; "TOPO" indicates topoisomerase; topoisomerase shown as circle attached to sequence; "P1" and "P2" indicate PCR primers. Topoisomerase recognition site is indicated in bold print. Number in parentheses above or below sequence indicates SEQ ID NO:.
Figure 1B:
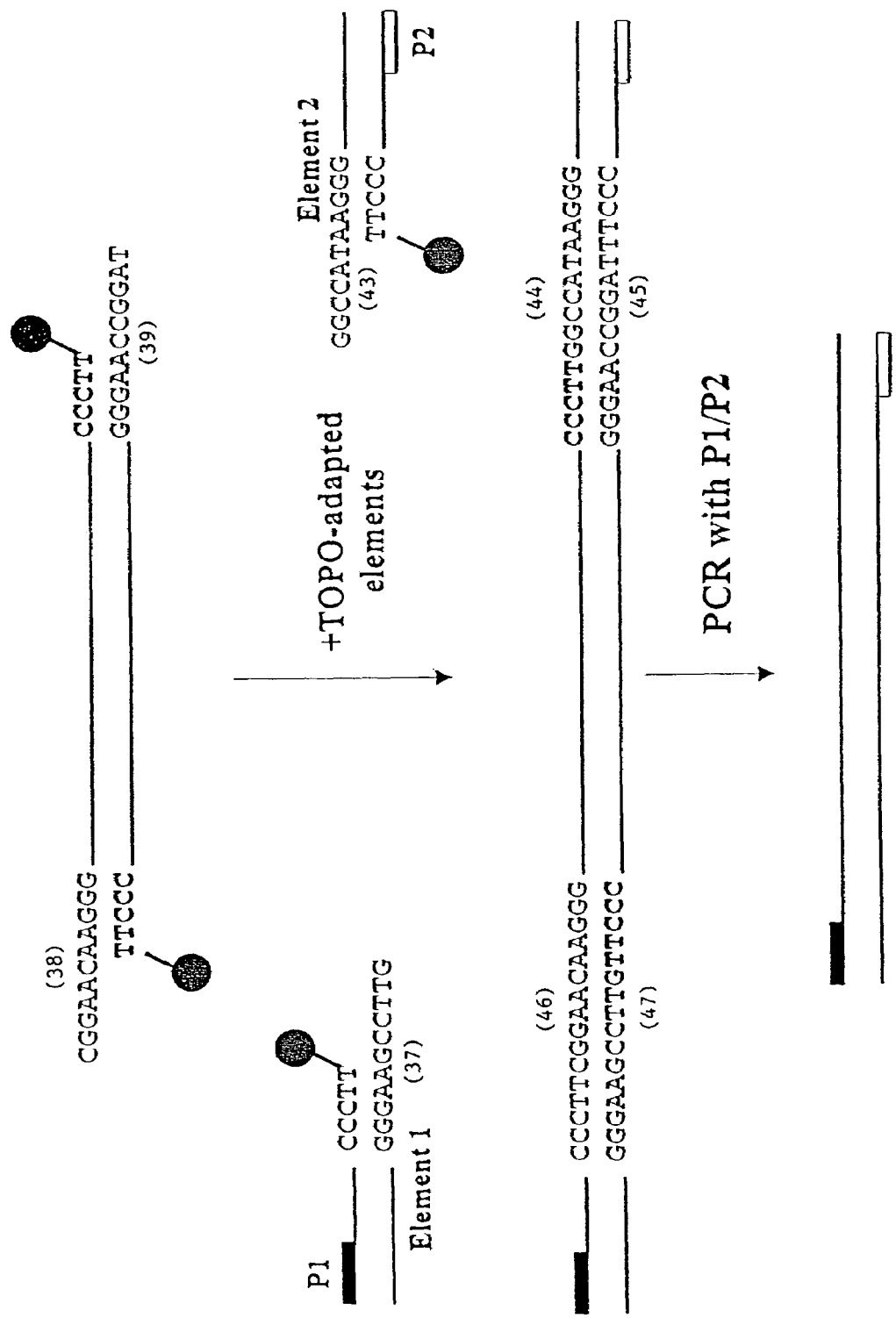

As disclosed herein, an advantage of a method of the invention for generating a ds recombinant nucleic acid molecule covalently linked in both strands is that there is no need to perform a separate ligation reaction in order to obtain a functional ds recombinant nucleic acid molecule covalently linked in both strands (see FIGS. 1 and 5). In addition, a method of this aspect of the invention can be performed such that, where a number of different ds nucleotide sequences are to be covalently linked in a predetermined orientation, there is no requirement that intermediate constructs be cloned, characterized and isolated before proceeding to a subsequent step (see Example 1.B). As such, the methods of this aspect of the invention provide a means to generate a ds recombinant nucleic acid molecule covalently linked in both strands much more quickly and at a substantially lower cost than was possible using previously known methods.

As an additional advantage, the generated ds recombinant nucleic acid molecules covalently linked in both strands are in a form that can be used directly in further procedures, for example, particular procedures involving extension or a primer such as a PCR amplification procedure, or other transcription or translation procedure, because the generated construct does not contain nicks at the sites where the ds nucleotides sequences have been joined. As disclosed herein, a method of the invention for generating a ds recombinant nucleic acid molecule covalently linked in one strand, in certain embodiments, also is advantageous in that the generated ds recombinant nucleic acid molecules are in a form that can be used directly in further procedures, for example, particular procedures involving extension of a primer such as a PCR amplification procedure, or other transcription or translation procedure, because in certain embodiments, the generated ds recombinant nucleic acid molecule contains one strand that does not contain a nick at the sites where the ds nucleotides sequences were joined.

The term "nucleotide sequence" or "ds nucleotide sequence" is used herein to refer to a discrete nucleic acid molecule. When used as such, the term "nucleotide sequence" is used merely for convenience such that the components in a composition or used in a method of the invention can be clearly distinguished. Thus, reference is made, for example, to "ds nucleotide sequences", which, in a method of the invention, correspond to the reactants (substrates) used to produce a recombinant "nucleic acid molecule" product.

Certain methods of the invention are exemplified generally herein with reference to the use of type IB topoisomerase such as the Vaccinia topoisomerase, or a type IA topoisomerase. However, it will be recognized that the methods also can be performed using a topoisomerase other than that exemplified, merely by adjusting the components accordingly. For example, as described in greater detail below, methods are disclosed for incorporating a type IB topoisomerase recognition site at one or both 3' termini of a linear ds nucleotide sequence using a PCR primer comprising, at least in part, a nucleotide sequence complementary to the topoisomerase recognition site. In comparison, a topoisomerase recognition site for a type IA or, if desired, type II topoisomerase, can be incorporated into a ds nucleotide sequence by using a PCR primer that contains the recognition site.

Cleavage of a ds nucleotide sequence by a site specific type IB topoisomerase results in the generation of a 5' overhanging sequence in the strand complementary to and at the same end as that containing the covalently bound topoisomerase. Furthermore, as disclosed herein, PCR primers can be designed that can incorporate a type IB topoisomerase recognition site into a ds nucleotide sequence, and that further can produce, upon cleavage of the ds nucleotide sequence by the topoisomerase, a 5' overhanging sequence in the complementary strand that has a defined and predetermined sequence. As such, the methods are readily adaptable to generating a ds recombinant nucleic acid molecule having the component ds nucleotide sequence operatively linked in a predetermined orientation. In view of the present disclosure, it will be recognized that PCR primers also can be designed such that a type IA topoisomerase recognition site can be introduced into a ds nucleotide sequence, including a library of diverse sequences, and, if desired, such that upon cleavage by a site-specific topoisomerase, generates a 3' overhanging sequence.

A method of generating a ds recombinant nucleic acid molecule covalently linked in both strands, as disclosed herein, extends the previously known methods by providing a topoisomerase at or near the terminus of each ds nucleotide sequence to be covalently linked. For example, with respect to a type IB topoisomerase, the method provides a topoisomerase recognition site, or a cleavage product thereof (i.e., a covalently bound type IB topoisomerase), at or near the 3' terminus of each linear ds nucleotide sequence to be linked. As used herein, the term "topoisomerase recognition site" means a defined nucleotide sequence that is recognized and bound by a site specific topoisomerase. For example, the nucleotide sequence 5'-(C/T)CCTT-3' is a topoisomerase recognition site that is bound specifically by most poxvirus topoisomerases, including vaccinia virus DNA topoisomerase I, which then can cleave the strand after the 3'-most thymidine of the recognition site to produce a nucleotide sequence comprising 5'-(C/T)CCTT-PO$_4$-TOPO, i.e., a complex of the topoisomerase covalently bound to the 3' phosphate through a tyrosine residue in the topoisomerase (see Shuman, *J. Biol. Chem.* 266:11372–11379, 1991;

Sekiguchi and Shuman, *Nucl. Acids Res.* 22:5360–5365, 1994; each of which is incorporated herein by reference; see, also, U.S. Pat. No. 5,766,891; PCT/US95/16099; PCT/US98/12372). In comparison, the nucleotide sequence 5'-GCAACTT-3' is the topoisomerase recognition site for type IA *E. coli* topoisomerase III.

Topoisomerase-charged ds nucleotide sequences, including those containing a topoisomerase covalently attached to a 5' terminus or 3' terminus or both, of one or both ends of the ds nucleotide sequence, can be generated by any of a number of methods. In some cases and under the appropriate conditions, type I topoisomerases can cleave a single stranded nucleotide sequence. For example, a domain comprising the amino-terminal 67 kDa domain of *E. coli* topoisomerase I, which is a type IA topoisomerase, can cleave a single stranded nucleotide sequence containing the topoisomerase recognition site. Where conditions are such that the topoisomerases can cleave a single stranded nucleotide sequence, cleavage of a ds nucleotide sequence containing topoisomerase recognition sites at the 5' and 3' termini of one end of ds nucleotide sequence can be performed in parallel. Alternatively, where one or both of the topoisomerases requires a ds nucleotide sequence for recognition and cleavage, the reactions are performed serially, wherein the more terminal (distal) of the topoisomerase recognition sites is cleaved first, then the more internal (proximal) site, which remains in a double stranded context, is cleaved. For example, a ds nucleotide sequence containing an *E. coli* topoisomerase III recognition site at or near a 5' terminus of an end and a Vaccinia type IB topoisomerase recognition site at or near the 3' terminus of the same end, and wherein the type IB recognition site is closer to the end than the type IA recognition site, the ds nucleotide sequence can be incubated with the Vaccinia topoisomerase, to produce a type IB topoisomerase-charged ds nucleotide sequence, then with the *E. coli* topoisomerase, to produce a ds nucleotide sequence having the type IA topoisomerase bound to the 5' terminus and the type IB topoisomerase bound to the 3' terminus. Accordingly, the invention includes methods for producing ds nucleotide sequence comprising a topoisomerase attached to one or both termini of at least one end, and further provides such topoisomerase-charged ds nucleotide sequences.

As used herein, the term "cleavage product," when used in reference to a topoisomerase recognition site, refers to a nucleotide sequence that has been cleaved by a topoisomerase, generally at its recognition site, and comprises a complex of the topoisomerase covalently bound, in the case of type IA or type II topoisomerase, to the 5' phosphate group of the 5' terminal nucleotide in the topoisomerase recognition site, or in the case of a type IB topoisomerase to the 3' phosphate group of the 3' terminal nucleotide in the topoisomerase recognition site. Such a complex, which comprises a topoisomerase cleaved ds nucleotide sequence having the topoisomerase covalently bound thereto, is referred to herein as a "topoisomerase-activated" or a "topoisomerase-charged" nucleotide sequence. Topoisomerase-activated ds nucleotide sequences can be used in a method of the invention, as can ds nucleotide sequences that contain an uncleaved topoisomerase recognition site and a topoisomerase, wherein the topoisomerase can cleave the ds nucleotide sequence at the recognition site and become covalently bound thereto.

In one embodiment of a method of generating a ds recombinant nucleic acid molecule covalently linked in both strands, a topoisomerase recognition site is present at or near the 3' terminus of the end of each nucleotide sequence to be linked such that, in the presence of a type IB topoisomerase, each nucleotide sequence is cleaved to produce a 3' terminus, which contains the topoisomerase covalently bound thereto (see FIG. 1). The nucleotide sequences to be covalently linked also can contain a 5' hydroxy group at the same end as that containing the topoisomerase recognition site, or a 5' hydroxyl group can be generated using a phosphatase. Upon contact of such nucleotide sequences, the site specific topoisomerase can ligate each strand containing a 3' phosphate to a respective 5' hydroxyl group, thereby generating a ds recombinant nucleic acid molecule covalently linked in both strands, which can be produced as a linear, circular, or positively or negatively supercoiled nucleic acid molecule.

Preferably, the 5' termini of the ends of the nucleotide sequences to be linked by a type IB topoisomerase according to a method of certain aspects of the invention contain complementary 5' overhanging sequences, which can facilitate the initial association of the nucleotide sequences, including, if desired, in a predetermined directional orientation. Alternatively, the 5' termini of the ends of the nucleotide sequences to be linked by a type IB topoisomerase according to a method of certain aspects of the invention contain complementary 5' sequences wherein one of the sequences contains a 5' overhanging sequence and the other nucleotide sequence contains a complementary sequence at a blunt end of a 5' terminus, to facilitate the initial association of the nucleotide sequences through strand invasion, including, if desired, in a predetermined directional orientation. The term "5' overhang" or "5"overhanging sequence" is used herein to refer to a strand of a ds nucleotide sequence that extends in a 5' direction beyond the terminus of the complementary strand of the ds nucleotide sequence. Conveniently, a 5' overhang can be produced as a result of site specific cleavage of a ds nucleotide sequence by a type IB topoisomerase (see Example 1).

Preferably, the 3' termini of the ends of the nucleotide sequences to be linked by a type IA topoisomerase according to a method of certain aspects of the invention contain complementary 3' overhanging sequences, which can facilitate the initial association of the nucleotide sequences, including, if desired, in a predetermined directional orientation. Alternatively, the 3' termini of the ends of the nucleotide sequences to be linked by a topoisomerase (e.g., a type IA or a type II topoisomerase) according to a method of certain aspects of the invention contain complementary 3' sequences wherein one of the sequences contains a 3' overhanging sequence and the other nucleotide sequence contains a complementary sequence at a blunt end of a 3' terminus, to facilitate the initial association of the nucleotide sequences through strand invasion, including, if desired, in a predetermined directional orientation. The term "3 overhang" or "3 overhanging sequence" is used herein to refer to a strand of a ds nucleotide sequence that extends in a 5' direction beyond the terminus of the complementary strand of the ds nucleotide sequence. Conveniently, a 3' overhang can be produced upon cleavage by a type IA or type II topoisomerase.

The 3' or 5' overhanging sequences can have any sequence, though generally the sequences are selected such that they allow ligation of a predetermined end of one ds nucleotide sequence to a predetermined end of a second nucleotide sequence according to a method of the invention (FIG. 2C, see, also Example 1.B). As such, while the 3' or 5' overhangs can be palindromic, they generally are not because ds nucleotide sequences having palindromic overhangs can associate with each other, thus reducing the yield of a ds recombinant nucleic acid molecule covalently linked in both strands comprising two or more ds nucleotide sequences in a predetermined orientation. For example, the 5' overhanging sequences of ds nucleotide sequences shown in FIG. 2A are palindrome and, therefore, the association, for example, of a first CMV element with a second CMV element through the AGCT overhang is just as likely as the association of a CMV element with a GFP element through the AGCT overhang. As such, the efficiency of generating a construct comprising an operatively covalently linked construct containing, in order from 5' to 3', a CMV element, a GFP element and a BGH element would be reduced as compared to the efficiency of generating such a construct using the elements as shown in FIG. 2C. The elements shown in FIG. 2B contain palindromic overhangs at one end of the GFP element and at the end of the BGH element shown and, therefore, would be less efficient than the elements of FIG. 2C, but more efficient than those in FIG. 2A, for generating the desired construct.

A nucleotide sequence used in the methods and kits of the current invention can be designed to contain a bridging phosphorothioate to prevent religation after topoisomerase-cleavage. For example, where the topoisomerase is *E. coli* topoisomerase III, the bridging phosphorothioate can be incorporated between the two thymidines of the GCAACTT cleavage/recognition sequence. When cleaved, the clipped sequence contains a 3'-SH instead of a 3'-OH, thus preventing religation (see Burgin et al, *Nucl. Acids Res.* 23:2973–2979, 1995).

A ds nucleotide sequence useful in a method or kit of an aspect of the invention can be amplified by an amplification method such as PCR to contain a topoisomerase recognition site at a 3' or 5' terminus of an end. Furthermore, one or both primers used for PCR can be designed such that, upon cleavage of an amplified ds nucleotide sequence, the cleaved ds nucleotide sequence contains a 5' or 3' overhang at one or both ends. In one embodiment, PCR primers are designed such that the 5' overhanging sequence on a first ds nucleotide sequence is complementary to a 5' overhanging sequence on a second (or other) ds nucleotide sequence, thereby facilitating the association of the nucleotide sequences, preferably in a predetermined orientation, whereupon they can be covalently linked according to a method of the invention. In accordance with the invention, by designing unique overhanging sequences for the different ds nucleotide sequence to be linked, any number of ds nucleotide sequences can be linked in a desired order and/or orientation.

It should be recognized that PCR is used in two ways with respect to the methods of the invention. In one aspect, PCR primers are designed to impart particular characteristics to a desired ds nucleotide sequence, for example, a ds nucleotide sequence that encodes a transcriptional or translational regulatory element or a coding sequence of interest such as an epitope tag or cell compartmentalization domain. In this aspect, the PCR primers can be designed such that, upon amplification, the ds nucleotide sequence contains a topoisomerase recognition site at one or both ends, as desired. As disclosed herein, the PCR primer also can include an additional sequence such that, upon cleavage of the amplification product by a site specific topoisomerase, the cleaved ds nucleotide sequence contains a 5' or 3' overhanging sequence at the topoisomerase cleaved end. In an embodiment of the invention involving a topoisomerase that binds and cleaves a 5' terminus (e.g., an embodiment involving a type IA topoisomerase), the PCR primers can be designed to contain a bridging phosphorothioate linkage (see above), which can block religation after topoisomerase cleavage and can assist in the generation of a topoisomerase-charged amplification product.

Overhanging sequences generated using PCR can include a single nucleotide overhang that is generated as an artifact of the PCR reaction. For example, a polymerase such at Taq, which does not have a proof-reading function and has an inherent terminal transferase activity, is commonly used, and produces PCR products containing a single, non-template derived 3' A overhang at each end. These amplification products can be linked to topoisomerase-charged ds nucleotide sequences containing a single 3' T overhang or a single 3' dU overhang, which, for a T/A cloning reaction, can be a vector (see U.S. Pat. Nos. 5,487,993 and 5,856,144, each of which is incorporated herein by reference), at one or both ends, using the methods of the invention.

Figure 6:
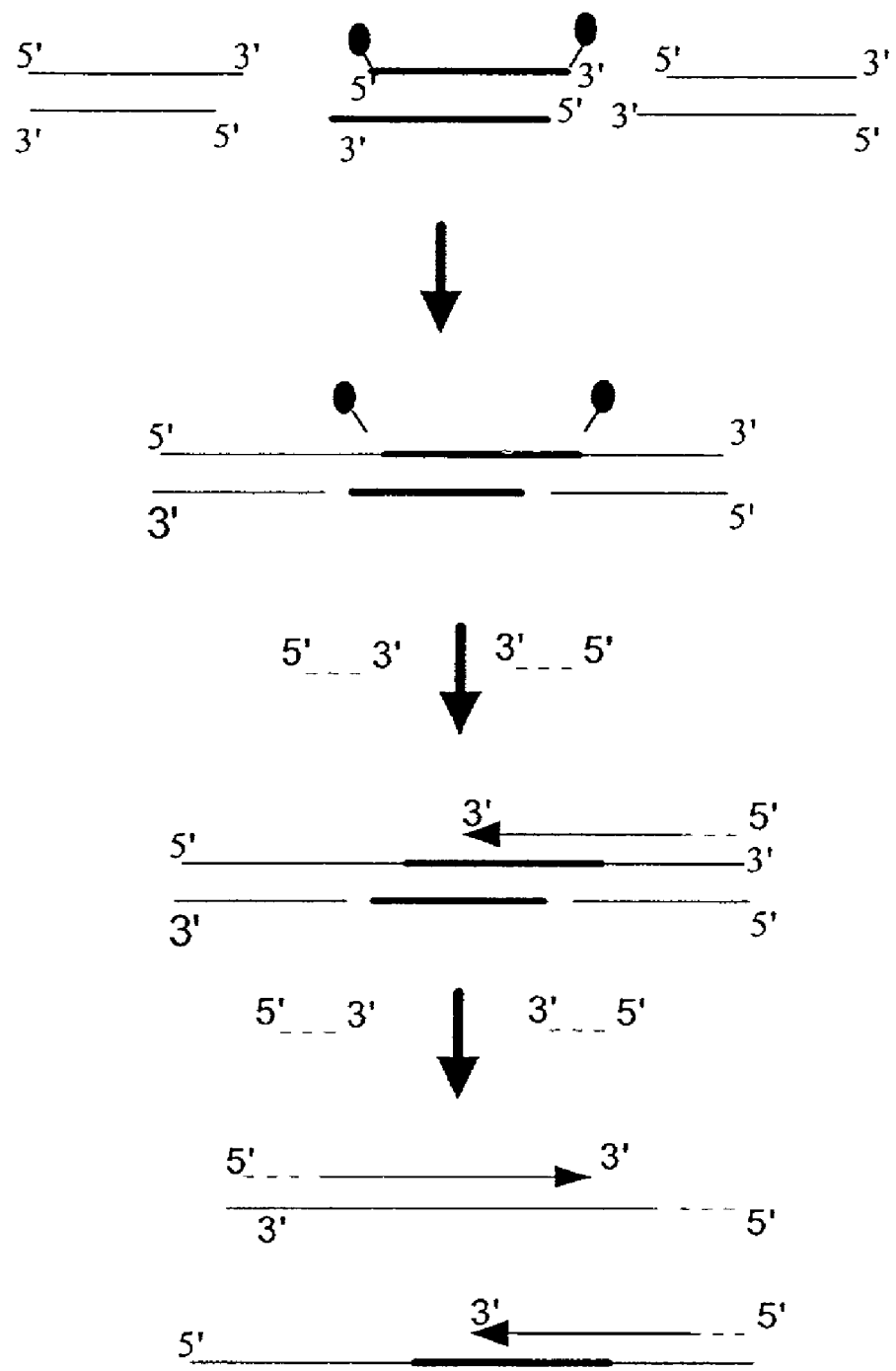
FIG. 6 illustrates the generation of an expressible ds recombinant nucleic acid molecule and amplification of the expressible ds recombinant nucleic acid molecule. Topoisomerase is shown as a solid circle, and is either attached to a terminus of a substrate ds nucleotide sequence or is released following a linking reaction. The expressible ds recombinant nucleic acid molecule is generated from three ds nucleotide sequences, including a nucleotide sequence comprising a promoter, a nucleotide sequence comprising a coding sequence, and a nucleotide sequence comprising a polyadenylation signal. Generation of the nucleic acid molecule can be facilitated by the incorporation of complementary 5' and/or 3' overhanging sequences at the ends of the ds nucleotides sequences to be joined. The expressible ds recombinant nucleic acid molecule is generated by contacting a first ds nucleotide sequence having a type IA topoisomerase at a 5' terminus of a first end and a type IB topoisomerase at a 3' terminus of a second end, with a second ds nucleotide sequence and a third double stranded nucleotide sequence. The expressible ds recombinant nucleic acid molecule is amplified using a first primer that hybridizes to the second ds recombinant nucleic acid molecule upstream of the promoter, and a second primer that hybridizes to the third ds recombinant nucleic acid molecule downstream of the polyadenylation signal.

PCR also is used to amplify a covalently linked ds recombinant nucleic acid molecule covalently linked in one or both strands, generated by a method of the invention. For example, as illustrated in FIG. 6, a method of the invention can generate an expressible ds recombinant nucleic acid molecule from three substrate ds nucleotide sequences, including a nucleotide sequence comprising a promoter, a nucleotide sequence comprising a coding sequence, and a nucleotide sequence comprising a polyadenylation signal. The generation of the ds recombinant nucleic acid molecule can be facilitated by the incorporation of complementary 3' (or 5') overhanging sequences at the ends of the ds nucleotides sequences to be joined. For example, the expressible ds recombinant nucleic acid molecule can be generated by contacting a first ds nucleotide sequence having a type IA topoisomerase at a 5' terminus of a first end and a type IB topoisomerase at a 3' terminus of a second end with a second ds nucleotide sequence and a third double stranded nucleotide sequence. By designing a PCR primer pair containing a first primer that is specific for a portion of the nucleotide sequence comprising the promoter that is upstream from the promoter, and a second primer that is specific for a portion of the nucleotide sequence comprising the polyadenylation signal that is down stream of the signal, only a full length functional ds recombinant nucleic molecule containing the promoter, coding sequence and polyadenylation signal in the correct (predetermined) orientation will be amplified. In particular, partial reaction products, for example, containing only a promoter linked to the coding sequence, and reaction products containing nicks are not amplified. Thus, PCR can be used to specifically design a ds nucleotide sequence such that it is useful in a method of the invention, and to selectively amplify only those reaction products having the desired components and characteristics.

As used herein, the term "covalently linked," when used in reference to a ds recombinant nucleic acid molecule, means that the nucleic acid molecule is generated from at least two ds nucleotide sequences that are ligated together, in both strands, by a topoisomerase mediated ligation. It should be recognized, for example, that a topoisomerase covalently bound to one of the ds nucleotide sequences to be covalently linked can be the same as or different from the topoisomerase covalently bound to the other ds nucleotide sequence. Thus, a Vaccinia topoisomerase can be covalently bound to one ds nucleotide sequence and another poxvirus or eukaryotic nuclear type IB topoisomerase can be bound to the other strand. Generally, however, the topoisomerases, where different, are members of the same family, for example, type IA or type IB or type II, although, where the topoisomerases are covalently bound, for example, to a 5' phosphate and generate complementary 3' overhangs, the topoisomerase can be from different families, for example, type IA and type II.

The term "covalently linked" also is used herein in reference to a single stranded or double stranded nucleic acid molecule that is generated from at least two nucleotide sequences that are ligated together in one strand. For example, a ds recombinant nucleic acid molecule that is generated when a first topoisomerase-charged ds nucleotide sequence that includes one topoisomerase bound at or near a 5' terminus contacts a second ds nucleotide sequence under conditions such that the topoisomerases can covalently link the 5' terminus of the first ds nucleotide sequence to which it is bound, to the 3' terminus of the second ds nucleotide sequence, can generate a ds recombinant nucleic acid molecule covalently linked in one strand.

In one embodiment, a ds recombinant nucleic acid molecule covalently linked in both strands generated according to a method of the invention does not contain a nick in either strand at the site where two nucleotide sequences are ligated, although it can contain nicks elsewhere in the molecule. In a method for generating a ds recombinant nucleic acid molecule covalently linked in one strand, a ds recombinant nucleic acid is generated that contains a nick at least at the position where ends were linked in the complementary strands. This nicked ds recombinant nucleic acid molecule can be converted to a ds recombinant nucleic acid molecule covalently linked in both strands by introducing the nicked ds recombinant nucleic acid molecule into a cell, or by subjecting the ds recombinant nucleic acid molecule to a ligation reaction, such as using a ligase, as is well known in the art.

The term "recombinant" is used herein to refer to a nucleic acid molecule that is produced by linking at least two nucleotide sequences according to a method of the invention. As such, a ds recombinant nucleic acid molecule encompassed within the present invention is distinguishable from a nucleic acid molecule that may be produced in nature, for example, during meiosis. For example, a ds recombinant nucleic acid molecule covalently linked in both strands generated according to a method of certain aspects of the invention can be identified by the presence of the two topoisomerase recognition sites, one present in each of the complementary strands, at or near the site at which the ds nucleotide sequences were joined.

A method of the invention can be performed by contacting a first ds nucleotide sequence having a first end and a second end, wherein at the first end or second end or both, the first ds nucleotide sequence has a topoisomerase recognition site, or cleavage product thereof, at or near the 3' terminus and has (or can be made to have, for example, by contact with a phosphatase) a hydroxyl group at the 5' terminus of the same end; at least a second ds nucleotide sequence having a first end and a second end, wherein at the first end or second end or both, the at least second ds nucleotide sequence has a topoisomerase recognition site, or cleavage product thereof, at or near the 3' terminus and has (or can be made to have) a hydroxyl group at the 5' terminus of the same end; and a topoisomerase, under conditions such that the components are in contact and the topoisomerase can effect its activity. Upon contact of the topoisomerase with the first and second (or other) ds nucleotide sequences, and cleavage, where necessary, each nucleotide sequence comprises at the cleavage site a covalently bound topoisomerase at the 3' terminus and has, or can have, a hydroxyl group at the 5' terminus such that, upon contact, the first and at least second nucleotide sequences are covalently linked in both strands. Accordingly, the invention provides a ds recombinant nucleic acid molecule covalently linked in both strands produced by such a method.

As used herein, the term "at or near," when used in reference to the proximity of a topoisomerase recognition site to the 3' (type IB) or 5' (type IA or type II) terminus of a nucleotide sequence, means that the site is within about 1 to 100 nucleotides from the 3' terminus or 5' terminus, respectively, generally within about 1 to 20 nucleotides from the terminus, and particularly within about 2 to 12 nucleotides from the respective terminus. An advantage of positioning the topoisomerase recognition site within about 10 to 15 nucleotides of a terminus is that, upon cleavage by the topoisomerase, the portion of the sequence downstream of the cleavage site can spontaneously dissociate from the remaining nucleotide sequence, which contains the covalently bound topoisomerase (referred to generally as "suicide cleavage"; see, for example, Shuman, supra, 1991; Andersen et al., supra, 1991). Where a topoisomerase recognition site is greater than about 12 to 15 nucleotides from the terminus, the nucleotide sequence upstream or downstream of the cleavage site can be induced to dissociate from the remainder of the sequence by modifying the reaction conditions, for example, by providing an incubation step at a temperature above the melting temperature of the portion of the duplex including the topoisomerase cleavage site.

An additional advantage of constructing a first or second (or other) ds nucleotide sequence to comprise, for example, a type IB topoisomerase recognition site about 2 to 15 nucleotides from one or both ends is that a 5' overhang is generated following cleavage of the ds nucleotide sequence by a site specific topoisomerase. Such a 5' overhanging sequence, which would contain 2 to 15 nucleotides, respectively, can be designed using a PCR method as disclosed herein to have any sequence as desired. Thus, where a cleaved first ds nucleotide sequence is to be covalently linked to a selected second (or other) ds nucleotide sequence according to a method of the invention, and where the selected sequence has a 5' overhanging sequence, the 5' overhang on the first ds nucleotide sequence can be designed to be complementary to the 5' overhang on the selected second (or other) ds sequence such that the two (or more) sequences are covalently linked in a predetermined orientation due to the complementarity of the 5' overhangs. As discussed above, similar methods can be utilized with respect to 3' overhanging sequences generated upon cleavage by, for example, a type IA or type II topoisomerase.

As used herein, reference to a nucleotide sequence having "a first end" and "a second end" means that the nucleotide sequence is linear. A substrate ds nucleotide sequence can be linear or circular, including supercoiled, although, as a result of cleavage by one or more topoisomerase, a linear topoisomerase-charged ds nucleotide sequence generally is produced. For example, a circular ds nucleotide sequence containing two type IB topoisomerase recognition sites within about 100 nucleotides of each other and in the complementary strands, preferably within about twenty nucleotides of each other and in the complementary strands, can be contacted with a site specific type IB topoisomerase such that each strand is cleaved and the intervening sequence dissociates, thereby generating a linear ds nucleotide sequence having a topoisomerase covalently bound to each end.

It should be recognized that reference to a first end or a second end of a ds nucleotide sequence is not intended to imply any particular orientation of the nucleotide sequence, and is not intended to imply a relative importance of the ends with respect to each other. Where a nucleotide sequence having a first end and second end is a double stranded nucleotide sequence, each end contains a 5' terminus and a 3' terminus. Thus, reference is made herein, for example, to a nucleotide sequence containing a topoisomerase recognition site at a 3' terminus and a hydroxyl group at the 5' terminus of the same end, which can be the first end or the second end.

A method of the invention can be performed using only a first ds nucleotide sequence and a second ds nucleotide sequence, or can additionally include a third, fourth or more ds nucleotide sequences as desired. Generally, each such nucleotide sequence contains a topoisomerase recognition site, or a cleavage product thereof, at or near at least one 3' or 5' terminus, and can contain a hydroxyl group at the 5' terminus of the same end, or a hydroxyl group can be generated using a phosphatase. Where a nucleotide sequence does not contain a topoisomerase recognition site at or near an end to be linked to a second nucleotide sequence, a topoisomerase recognition site can be introduced into the nucleotide sequence using a method as disclosed herein, for example, by PCR amplification of the sequence using a primer comprising a complement of the topoisomerase recognition site.

The terms "first nucleotide sequence," "second nucleotide sequence," "third nucleotide sequence," and the like, are used herein only to provide a means to indicate which of several nucleotide sequences is being referred to. Thus, absent any specifically defined characteristic with respect to a particular nucleotide sequence, the terms "first," "second," "third" and the like, when used in reference to a nucleotide sequence, or a population or plurality of nucleotide sequences, are not intended to indicate any particular order, importance or other information about the nucleotide sequence. Thus, where an exemplified method refers, for example, to using PCR to amplify a first ds nucleotide sequence such that the amplification product contains a topoisomerase recognition site at one or both ends, it will be recognized that, similarly, a second (or other) ds nucleotide sequence also can be so amplified.

The term "at least a second nucleotide sequence" is used herein to mean one or more nucleotide sequences in addition to a first nucleotide sequence. Thus, the term can refer to only a second nucleotide sequence, or to a second nucleotide sequence and a third nucleotide sequence (or more). As such, the term "second (or other) nucleotide sequence" or second (and other) nucleotide sequences" is used herein in recognition of the fact that the term "at least a second nucleotide sequence" can refer to a second, third or more nucleotide sequences. It should be recognized that, unless indicated otherwise, a nucleotide sequence encompassed within the meaning of the term "at least a second nucleotide sequence" can be the same or substantially the same as a first nucleotide sequence. For example, a first and second ds nucleotide sequence can be the same except for having complementary 5' overhanging sequences produced upon cleavage by a topoisomerase such that the first and second ds nucleotide sequences can be covalently linked using a method of the invention. As such, a method of the invention can be used to produce a concatenate of first and second ds nucleotide sequences, which, optionally, can be interspersed, for example, by a third ds nucleotide sequence such as a regulatory element, and can contain the covalently linked sequences in a predetermined directional orientation, for example, each in a 5' to 3' orientation with respect to each other.

As disclosed herein, a method of the invention provides a means to covalently link, two or more ds nucleotides in a predetermined directional orientation. The term "directional orientation" or "predetermined directional orientation" or "predetermined orientation" is used herein to refer to the covalent linkage, of two or more nucleotide sequences in a particular order. Thus, a method of the invention provides a means, for example, to covalently link, a promoter regulatory element upstream of a coding sequence, and to covalently link a polyadenylation signal downstream of the coding region to generate a functional expressible ds recombinant nucleic acid molecule; or to covalently link two coding sequences such that they can be transcribed and translated in frame to produce a fusion polypeptide.

A method of the invention also can be performed by contacting a first ds nucleotide sequence having a first end and a second end, wherein at the first end or second end or both, the first ds nucleotide sequence has a type IB topoisomerase covalently bound at the 3' terminus (topoisomerase-charged) and has (or can be made to have) a hydroxyl group at the 5' terminus of the same end; and at least a second type IB topoisomerase-charged ds nucleotide sequence, which has (or can be made to have) a hydroxyl group at the 5' terminus at the same end. Upon contact of the topoisomerase-activated first and at least second nucleotide sequences at the ends containing the topoisomerase and a 5' hydroxyl group, phosphodiester bonds are formed in each strand, thereby generating a ds recombinant nucleic acid molecule covalently linked in both strands.

The invention further provides methods for linking two or more (e.g., two, three, four, five, six, seven, etc.) nucleotide sequences, wherein the linked ds recombinant nucleic acid molecule is covalently linked in one strand, but not both strands, (i.e. the ds recombinant nucleic acid molecule contains a nick in one strand at each position where two ends were joined to generate the ds recombinant nucleic acid molecule. Using the schematic shown in FIG. 4A for purposes of illustration, the invention includes methods for linking at least two nucleotide sequences comprising contacting a first ds nucleotide sequence having a first end and a second end, wherein at the first end at the second end or at both ends, the first ds nucleotide sequence has a site-specific type IA topoisomerase covalently bound to the 5' termini; and a second ds nucleotide sequence which does not have topoisomerase covalently bound to either termini of at least one end. Further, the second nucleotide sequence will typically have hydroxyl groups at the 3' termini of the end being joined to the first ds nucleotide sequence. In many instances, the two nucleotide sequences to be joined will have either 3' or 5' overhangs with sufficient sequence complementarity to allow for hybridization. In related embodiments, the first and second ds nucleotide sequences described above may be first and second ends of the same ds nucleotide sequence. Thus, connection of the two ends results in the formation of a circularized molecule.

Using the schematic shown in FIG. 4B for purposes of illustration, the invention includes methods for joining three or more nucleotide sequences. While any number of variations of the invention are possible, three nucleotide sequences may be joined by the use of a linker molecule which contains topoisomerases at both the 5' and 3' termini of one end. Thus, upon joining of the three nucleotide sequences, a single nucleotide sequence is formed which contains a first strand with no nicks at the junction points, and a second strand with nicks at the junction points. This process has the advantage of employing a single topoisomerase modified molecule to join three nucleotide sequences together.

The invention further provides methods for covalently linking both strands of two or more (e.g., two, three, four, five, six, seven, etc.) ds nucleotide sequences. Using the schematic shown in FIG. 5A for purposes of illustration, the invention includes methods for linking at least two nucleotide sequences comprising contacting a first ds nucleotide sequence having a first end and a second end, wherein at the first end at the second end or at both ends, the first ds nucleotide sequence has two topoisomerases (e.g., a type IA and a type IB topoisomerase) one each covalently bound to the 3' and 5' termini; and a second ds nucleotide sequence which does not have topoisomerase covalently bound to either termini of at least one end. Further, the second nucleotide sequence will often have hydroxyl groups at the 5' and 3' termini of the end being joined to the first ds nucleotide sequence. In many instances, the two nucleotide sequences to be joined will have either 3' or 5' overhangs with sufficient sequence complementarity to allow for hybridization. In related embodiments, the first and second ds nucleotide sequences as described above can be first and second ends of the same ds nucleotide sequence. Thus, connection of the two ends results in the formation of a circularized molecule.

Using the schematic shown in FIG. 5D for purposes of illustration, the invention includes methods for joining three or more nucleotide sequences. While any number of variations of the invention are possible, three nucleotide sequences may be joined by the use of a linker molecule which contains topoisomerases at both the 5' and 3' termini of each end. Thus, upon joining of the three nucleotide sequences, a single nucleotide sequence is formed which contains no nicks at the junction points. This process has the advantage of employing a single topoisomerase modified molecule to join three nucleotide sequences together.

The present invention also provides compositions, and kits containing such compositions, including kits containing component useful for performing methods of the invention. In one aspect, a composition of the invention comprises isolated components characteristic of a step of a method of the invention. For example, a composition of the invention can comprise two or more of the same or different topoisomerase-charged ds nucleotide sequences. As used herein, the term "different," when used in reference to the ds nucleotide sequences of a composition of the invention, means that the ds nucleotide sequences share less than 95% sequence identity with each when optimally aligned, generally less than 90% sequence identity, and usually less than 70% sequence identity. Thus, ds nucleotide sequences that, for example, differ only in being polymorphic variants of each other or that merely contain different 5' or 3' overhanging sequences are not considered to be "different" for purposes of a composition of the invention. In comparison, different ds nucleotide sequences are exemplified by a first sequence encoding a polypeptide and second sequence comprising a regulatory element, or a first sequence encoding a first polypeptide a second sequence encoding a non-homologous polypeptide.

Where a composition of the invention comprises more than two different isolated ds nucleotide sequences or more than two different topoisomerase-charged ds nucleotide sequences, each of the ds nucleotide sequences is different from each other, i.e., they are all different from each other. However, it will be recognized that each of the ds nucleotide sequences, for example, a sequence referred to as a first ds nucleotide sequence, generally comprises a population of such nucleotide sequences, which are identical or substantially identical to each other. Thus, it should be clear that the term "different" is used in comparing, for example, a first (or population of first) ds nucleotide sequences with a second (and other) ds nucleotide sequence. A composition comprising two or more different topoisomerase-charged ds nucleotide sequences can further comprise a topoisomerase. Examples of such ds nucleotide sequences comprising the components of a composition of the invention are disclosed herein and include, for example, coding sequences, transcriptional regulatory element, translational regulatory elements, elements encoding a detectable or selectable markers such as an epitope tag or an antibiotic resistance gene, elements encoding polypeptide domains such as cell compartmentalization domains or signal peptides, and the like.

As used herein, the term "isolated" means that a molecule being referred to is in a form other than that in which it exists in nature. In general, an isolated nucleotide sequence, for example, can be any nucleotide sequence that is not part of a genome in a cell, or is separated physically from a cell that normally contains the nucleotide sequence. It should be recognized that various compositions of the invention comprise a mixture of isolated ds nucleotide sequences. As such, it will be understood that the term "isolated" only is used in respect to the isolation of the molecule from its natural state, but does not indicate that the molecule is an only constituent.

A composition of the invention can comprise two different ds nucleotide sequences, each of which contains a topoisomerase recognition site at or near one or both ends, and a site specific topoisomerase, which can bind to and cleave the ds nucleotide sequences at the topoisomerase recognition site. Optionally, at least one of the different ds nucleotide sequences can be a topoisomerase-charged ds nucleotide sequence. Preferably, the topoisomerase covalently bound to the topoisomerase-charge ds nucleotide sequence is of the same family as the topoisomerase in the composition.

Various combinations of components can be used in a method of the invention. For example, the method can be performed by contacting a topoisomerase-activated first ds nucleotide sequence; a second ds nucleotide sequence having a first end and a second end, wherein at the first end or second end or both, the second nucleotide sequence has a topoisomerase recognition site at or near the 3' terminus, and a hydroxyl group at the 5' terminus of the same end; and a topoisomerase. Where the 5' terminus of one or both ends to be linked has a 5' phosphate group, a phosphatase also can be contacted with the components of the reaction mixture. Upon such contacting, the topoisomerase can cleave the second nucleotide sequence to produce a topoisomerase-activated second ds nucleotide sequence, the phosphatase, if necessary, can generate a 5' hydroxyl group at the same end, and the second ds nucleotide sequence then can be covalently linked to the topoisomerase-activated first ds nucleotide sequence. As such, it will be recognized that a composition of the invention can comprise any of various combinations of components useful for performing a method of the invention.

In general, a method of the invention for generating a ds recombinant nucleic acid molecule covalently linked in both strands is based on the determination that a ds recombinant nucleic acid molecule covalently linked in both strands can be produced by contacting a first ds nucleotide sequence with a second ds nucleotide sequence, wherein the first and second sequences each have, at the ends to be linked, a topoisomerase recognition site, for example, 5'-(C/T)CCTT-3' (Shuman, supra, 1991; U.S. Pat. No. 5,766,891). Upon cleavage, the site specific topoisomerase is covalently bound at the 3' terminus. Where the cleaved nucleotide sequences also contain a 5' hydroxy group at the same end as the bound topoisomerase, and the ends of the two nucleotide sequences associate, the topoisomerase on each 3' terminus can covalently link that terminus to a 5' hydroxyl group on the associated nucleotide sequence (see FIG. 1).

As used herein, reference to contacting a first nucleotide sequence and at least a second nucleotide sequence "under conditions such that all components are in contact" means that the reaction conditions are appropriate for the topoisomerase-cleaved ends of the nucleotide sequences to come into sufficient proximity such that a topoisomerase can effect its enzymatic activity and covalently link the 3' or 5' terminus of a first nucleotide sequence to a 5' or 3' terminus, respectively,-of a second nucleotide sequence. Examples of such conditions, which include the reaction temperature, ionic strength, pH, and the like, are disclosed herein, and other appropriate conditions as required, for example, for particular 5' overhanging sequences of the termini generated upon topoisomerase cleavage, can be determined empirically or using formulas that predict conditions for specific hybridization of nucleotide sequences, as is well known in the art (see, for example, (Sambrook et al., *Molecular Cloning: A laboratory manual* (Cold Spring Harbor Laboratory Press 1989); Ausubel et al., *Current Protocols in Molecular Biology*, John Wiley and Sons, Baltimore, Md. (1987, and supplements through 1995), each of which is incorporated herein by reference).

In one embodiment, a method of the invention provides a means to render an open reading from a cDNA or an isolated genomic DNA sequence expressible by operatively linking one or more regulatory elements to the putative coding sequence. Accordingly, a first ds nucleotide sequence comprising an open reading frame can be amplified by PCR using a primer pair that generates an amplified first ds nucleotide sequence having a topoisomerase recognition site at one or both ends, as desired, preferably such that, upon cleavage by the site specific topoisomerase, one or both ends contains a defined 5' or 3' overhang. Where both ends of the amplified first ds nucleotide sequence are so constructed, the 5' or 3' overhanging sequences generally, but not necessarily, are different from each other. The amplified first ds nucleotide sequence then can be contacted with a second ds nucleotide sequence comprising a desired regulatory element such as a promoter and, in certain embodiments, a topoisomerase recognition site, and with a topoisomerase, such that the second nucleotide sequence is operatively covalently linked to the 5' end of the coding sequence according to a method of the invention.

In such a method, a second (or other) ds nucleotide sequence also can comprise two or more regulatory elements, for example, a promoter, an internal ribosome entry site and an ATG initiator methionine codon, or the like, or other sequence of interest, for example, an sequence encoding an epitope tag, in operative linkage with each other, and which can be operatively covalently linked to the 5' end of a first ds nucleotide sequence comprising a coding sequence. Such a method can further include contacting a third ds nucleotide sequence comprising, for example, a polyadenylation signal, which can be operatively covalently linked according to a method of the invention to the 3' end of the coding sequence, thereby generating an expressible ds recombinant nucleic acid molecule. As such, a method of the invention provides a means for generating a functional ds recombinant nucleic acid molecule that can be transcribed, translated, or both as a functional unit. As disclosed herein, the inclusion of complementary 5' or 3' overhanging sequences generated by topoisomerase cleavage at the termini of the ds nucleotide sequences to be linked together by the site specific topoisomerase facilitates the generation of a ds recombinant nucleic acid molecule having a desired directional orientation of the nucleotide sequences in the construct.

In another embodiment, a method of the invention is performed such that the first ds nucleotide sequence or a second (or other) ds nucleotide sequence, or combination thereof, is one of a plurality of nucleotide sequences. As used herein, the term "plurality," when used in reference to a first or at least a second nucleotide sequence, means that the nucleotide sequences are related but different. For purposes of the present invention, the nucleotide sequences of a plurality are "related" in that each nucleotide sequence in the plurality contains at least a topoisomerase recognition site, or a cleaved form thereof, at one or more termini. Furthermore, the nucleotide sequences of a plurality are "different" in that they can comprise, for example, a cDNA library, a combinatorial library of nucleotide sequences, a variegated population of nucleotide sequences, or the like. Methods of making cDNA libraries, combinatorial libraries, libraries comprising variegated populations of nucleotide sequences, and the like are well known in the art (see, for example, U.S. Pat. No. 5,837,500; U.S. Pat. No. 5,622,699; U.S. Pat. No. 5,206,347; Scott and Smith, *Science* 249: 386–390, 1992; Markland et al., *Gene* 109:13–19, 1991; O'Connell et al., *Proc. Natl. Acad. Sci., USA* 93:5883–5887, 1996; Tuerk and Gold, *Science* 249:505–510, 1990; Gold et al., *Ann. Rev. Biochem.* 64:763–797, 1995; each of which is incorporated herein by reference).

The present invention further provides a method of generating a ds recombinant nucleic acid molecule covalently linked in both strands by amplifying a portion of a first nucleotide sequence using a PCR primer pair, wherein at least one primer of the primer pair encodes a topoisomerase recognition site or a complement thereof, thereby producing a first ds nucleotide sequence having a first end and a second end, wherein the first end or second end or both has a topoisomerase recognition site at the 3' terminus and/or the 5' terminus; and contacting the first ds nucleotide sequence; at least a second ds nucleotide sequence having a first end and a second end, wherein the first end or second end or both has a topoisomerase recognition site at the 3' terminus and/or the 5' terminus, or a cleavage product thereof; and a topoisomerase (see FIG. 1). When contacted under conditions such that an end of the first ds nucleotide sequence having a topoisomerase recognition site and an end of the at least second ds nucleotide sequence having a topoisomerase recognition site can associate, a ds recombinant nucleic acid molecule covalently linked in both strands is generated.

As disclosed herein, a PCR method using primers designed to incorporate a topoisomerase recognition site at one or both ends of an amplified ds nucleotide sequence provides a convenient means for producing ds nucleotide sequences useful in a method of the invention. In certain embodiments, at least one of the primers of a primer pair is designed such that it comprises, in a 5' to 3' orientation, a nucleotide sequence complementary to a topoisomerase recognition site, and a nucleotide sequence complementary to the 3' end of a target nucleic acid molecule to be amplified (i.e., a target specific region). In addition, the primer can contain, in a position 5' to the complement of the topoisomerase recognition site, a desired nucleotide sequence of any length (generally about 1 to 100 nucleotide, usually about 2 to 20 nucleotides, and particularly about 4 to 12 nucleotides), which, upon cleavage of the amplification product by a site specific topoisomerase, forms a desired 5' overhang. The second primer of the PCR primer pair can be complementary to a desired sequence of the nucleotide sequence to be amplified, and can comprise a complement to a topoisomerase recognition site, a sequence that would generate a 5' overhang upon cleavage by a site specific topoisomerase, or any other sequence, as desired.

Such a primer can comprise or encode any other sequence of interest, including, for example, a site specific integration recognition site such as an att site, a lox site, or the like, or, as discussed above, can simply be used to introduce a topoisomerase recognition site into a ds nucleotide sequence comprising such a sequence of interest. A ds recombinant nucleic acid molecule generated according to a method of the invention and containing a site specific integration recognition site such as an att site or lox site can be integrated specifically into a desired locus such as into a vector, a gene locus, or the like, that contains the required integration site, for example, an att site or lox site, respectively, and upon contact with the appropriate enzymes required for the site specific event, for example, lambda Int and IHF proteins or Cre recombinase, respectively. The incorporation, for example, of attB or attP sequences into a ds recombinant nucleic acid molecule covalently linked in both strands according to a method of the invention allows for the convenient manipulation of the nucleic acid molecule using the GATEWAY™ Cloning System (Invitrogen Corp., La Jolla Calif.).

In one embodiment, a construct generated according to a method of the invention is further amplified by a PCR reaction or other amplification reaction. Direct PCR of a ds recombinant nucleic acid molecule generated according to a method of the invention is possible because the construct is covalently linked in at least one strand. As such, PCR can be used to generate a large amount of the construct. More importantly, as indicated above, PCR provides an in vitro selection method for obtaining only a desired product generated according to a method of the invention, without obtaining partial reaction products. For example, a method of the invention can be used to generate a ds recombinant nucleic acid molecule covalently linked in both strands comprising, operatively linked in a 5' to 3' orientation, a first ds nucleotide sequence comprising a promoter, a second ds nucleotide sequence comprising a coding region, and a third ds nucleotide sequence comprising a polyadenylation signal.

As disclosed herein, a construct having a predetermined orientation can be generated by including complementary 5' overhanging sequences on the ends of the ds nucleotide sequences to be joined. By selecting a PCR primer pair including a first primer complementary to the first ds nucleotide sequence and upstream of the promoter sequence, and a second primer complementary to the third ds nucleotide sequence and downstream of the polyadenylation signal, a functional amplification product comprising the promoter, coding region and polyadenylation signal can be generated. In contrast, partial reaction products that lack either the first ds nucleotide sequence or third ds nucleotide is not amplified because either the first or second primer, respectively, would not hybridize to the partial product. In addition, a construct lacking the second ds nucleotide sequence would not be generated due to the lack of complementarity of the 5' overhanging sequences of the first and third ds nucleotide sequences. As such, a method of the invention provides a means to obtain a desired functional ds recombinant nucleic acid molecule covalently linked in both strands.

The use of PCR in such a manner further provides a means to screen a large number of nucleic acid molecules generated according to a method of the invention in order to identify constructs of interest. Since methods for utilizing PCR in automated high throughput analyses are routine and well known, it will be recognized that the methods of the invention can be readily adapted to use in a high throughput system. Using such a system, a large number of constructs can be screened in parallel, and partial or incomplete reaction products can be identified and disposed of, thereby preventing a waste of time and expense that would otherwise be required to characterize the constructs or examine the functionality of the constructs in further experiments.

The methods of the invention have broad application to the field of molecular biology. As discussed in greater detail below, the methods of the invention can be used, for example, to label DNA or RNA probes, to perform directional cloning (see Example 1.B), to generate sense or antisense RNA molecules (see Example 2.A), to prepare bait or prey constructs for performing a two hybrid assay (see Example 2.C), to prepare linear expression elements (see Examples 2.A and 2.B), and to prepare constructs useful for coupled in vitro transcription/translation assays (see Example 2.B). For example, a method of generating ds recombinant nucleic acid molecules covalently linked in both strands provides a means to generate linear expression elements (LEEs), which consist of a linear nucleic acid molecule comprising two or more nucleotide sequences such as a promoter or other regulatory element linked to an open reading frame (see Example 1). LEEs have been reported to efficiently transfect cells, thus bypassing a requirement for cloning the expression element in a vector (Sykes and Johnston, *Nat. Biotechnol.* 17:355–359, 1999). The components of a LEE can be noncovalently linked, or can be covalently linked via a ligation reaction. The preparation of noncovalently linked LEEs requires using PCR primers containing deoxyuridine residues to amplify each nucleotide sequence component, then treating the PCR products with uracil-DNA glycosylase to generate overhanging ends that can hybridize. However, the efficiency of transfection using such noncovalently linked LEEs is variable, and, in some cases, much lower than the efficiency of covalently linked LEEs (Sykes and Johnston, supra, 1999). Furthermore, such LEEs are not suitable for use as templates for PCR amplification because the primer extension reaction cannot proceed past nicks in the template and, therefore, is terminated producing incomplete reaction products.

A method of the invention provides a straightforward and simple means to generate covalently linked LEEs, thereby avoiding the inconvenient and additional steps previously described for preparing a LEE, as well as reducing variability in transfection efficiency as observed using noncovalently linked LEEs. For example, a first ds nucleotide sequence, which encodes an open reading frame of interest, can be amplified by PCR as disclosed herein to contain a topoisomerase recognition site, or cleavage product thereof, on one or both ends. Furthermore, the PCR primers can be designed such that, upon cleavage of the amplified first ds nucleotide sequence by a site specific topoisomerase, the cleavage product contains a predetermined and desired 5' overhanging sequence. A second nucleotide sequence (and a third or more, as desired), in addition to containing a topoisomerase recognition site, or cleavage product thereof, can include or encode a regulatory element, for example, a promoter, an enhancer, a silencer, a splice acceptor site, a translation start site, a ribosome recognition site or internal ribosome entry site, a polyadenylation signal, an initiator methionine codon, or a STOP codon, or can encode any other desired sequence such as an epitope tag or cell compartmentalization domain. Preferably, the second (or other) ds nucleotide sequence to be covalently linked to the first ds nucleotide sequence has a 5' overhanging sequence that is complementary to the 5' overhang at the end of the first ds nucleotide sequence to which it is to be linked. Upon contact of such nucleotide sequences in presence of a topoisomerase a promoter, for example, can be operatively covalently linked to the 5' terminus of the open reading frame, and a polyadenylation signal can be operatively covalently linked to the 3' terminus of the open reading frame, thereby generating a covalently linked functional LEE (see Example 1).

Examples of regulatory elements useful in the present invention are disclosed herein and include transcriptional regulatory elements, translational regulatory elements, elements that facilitate the transport or localization of a nucleotide sequence or polypeptide in (or out of) a cell, elements that confer a detectable phenotype, and the like. Transcriptional regulatory elements include, for example, promoters such as those from cytomegalovirus, Moloney leukemia virus, and herpes virus, as well as those from the genes encoding metallothionein, skeletal actin, phosphoenolpyruvate carboxylase, phosphoglycerate, dihydrofolate reductase, and thymidine kinase, as well as a GAL4 promoter and promoters from viral long terminal repeats (LTRs) such as Rous sarcoma virus LTR; enhancers, which can be constitutively active such as an immunoglobulin enhancer, or inducible such as SV40 enhancer; and the like. For example, a metallothionein promoter is a constitutively active promoter that also can be induced to a higher level of expression upon exposure to a metal ion such as copper, nickel or cadmium ion. In comparison, a tetracycline (tet) inducible promoter is an example of a promoter that is induced upon exposure to tetracycline, or a tetracycline analog, but otherwise is inactive. A transcriptional regulatory element also can be a tissue specific regulatory element, for example, a muscle cell specific regulatory element, such that expression of an encoded product is restricted to the muscle cells in an individual, or to muscle cells in a mixed population of cells in culture, for example, an organ culture. Muscle cell specific regulatory elements including, for example, the muscle creatine kinase promoter (Sternberg et al., *Mol. Cell. Biol.* 8:2896–2909, 1988, which is incorporated herein by reference) and the myosin light chain enhancer/promoter (Donoghue et al., *Proc. Natl. Acad. Sci. USA* 88:5847–5851, 1991, which is incorporated herein by reference) are well known in the art. Other tissue specific promoters, as well as regulatory elements only expressed during particular developmental stages of a cell or organism are well known in the art.

Regulatory or other elements useful in generating a construct according to a method of the invention can be obtained in various ways. In particular, many of the elements are included in commercially available vectors and can be isolated therefrom and can be modified to contain a topoisomerase recognition site at one or both ends, for example, using a PCR method as disclosed herein. In addition, the sequences of or encoding the elements useful herein generally are well known and disclosed in publications. In many cases, the elements, for example, many transcriptional and translational regulatory elements, as well as cell compartmentalization domains, are relatively short sequences and, therefore, are amenable to chemical synthesis of the element or a nucleotide sequence encoding the element. Thus, in one embodiment, an element comprising a composition of the invention, useful in generating a ds recombinant nucleic acid molecule according to a method of the invention, or included within a kit of the invention, can be chemically synthesized and, if desired, can be synthesized to contain a topoisomerase recognition site at one or both ends of the element and, further, to contain an overhanging sequence following cleavage by a site specific topoisomerase.

A topoisomerase-charged vector can be generated in the following manner (*Genome Res.* 9: 383–392, 1999): A vector is linearized with a restriction enzyme that leaves "sticky ends". Using a ligase such as T4 DNA ligase, adapter oligonucleotides are ligated to both ends, and both strands, of the linearized DNA. The adapter oligonucleotides contain and position a 5'-CCCTT-3' Vaccinia topoisomerase type I recognition sequence such that it can be cleaved by topoisomerase and trap the covalent topoisomerase-DNA complex at each 3' end of the vector. The adapted vector is then incubated with purified Vaccinia topoisomerase and an annealing oligonucleotide that complete the "topoisomerase sites" at each end of the vector. The annealing oligonucleotide acts to leave a break, or nick, in the "bottom" strand opposite the last T in the 5'-CCCTT-3' containing oligonucleotide. The oligonucleotide adapter fragments that are "downstream" of the topoisomerase cleavage site (the "leaving groups") are released upon topoisomerase cleavage and are removed in the topoisomerase-vector purification process. In the absence of the 5' hydroxyl from the "leaving group", topoisomerase is trapped in a covalent complex with the DNA ends to produce a topoisomerase-charged vector.

Where ds nucleotide sequences are to be covalently linked according to a method of the invention, the nucleotide sequences generally are operatively linked such that the recombinant nucleic acid molecule that is generated has a desired structure and performs a desired function or encodes a desired expression product. As used herein, the term "operatively linked" means that two or more nucleotide sequences are positioned with respect to each other such that they act as a unit to effect a function attributable to one or both sequences or a combination thereof. The term "operatively covalently linked" is used herein to refer to operatively linked nucleotide sequences generated according to a method of the invention for generating a ds recombinant nucleic acid molecule covalently linked in one or both strands. For example, a nucleotide sequence containing an open reading frame can be operatively linked to a promoter such that the promoter confers its regulatory effect on the open reading frame similarly to the way in which it would effect expression of an open reading frame that it normally is associated with in a genome in a cell. Similarly, two or more nucleotide sequences comprising open reading frames can be operatively linked in frame such that, upon transcription and translation, a chimeric fusion polypeptide is produced.

Although a ds recombinant nucleic acid molecule covalently linked in one or both strands, generated according to a method of the invention generally is linear, the construct generated also can be a circularized ds recombinant nucleic acid molecule. Furthermore, a circular ds recombinant nucleic acid molecule can be generated such that it has the characteristics of a vector, and contains, for example, regulatory elements (expression control sequences) required for replication in a prokaryotic host cell, a eukaryotic host cell, or both; can contain a nucleotide sequence encoding a polypeptide that confers antibiotic resistance; a multiple cloning site; or the like. An advantage of such a method is that the generated ds recombinant nucleic acid molecule, which is circularized according to a method of the invention, can be transformed or transfected into an appropriate host cell, wherein the construct is amplified. Thus, in addition to an in vitro method such as PCR, which can be used to generate large amounts of a linear ds recombinant nucleic acid molecule generated according to a method of the invention, an in vivo method using a host cell can be used for obtaining a large amount of a circularized product generated according to a method of the invention. Such elements including bacterial origins of replication, antibiotic resistance genes, and the like, which comprise a topoisomerase recognition site according to the present invention, can be useful components to include in a kit of the invention as disclosed herein.

It should be recognized that a linear ds recombinant nucleic acid molecule covalently linked in one or both strands, also can be cloned into a vector, which can be a plasmid vector or a viral vector such as a bacteriophage, baculovirus, retrovirus, lentivirus, adenovirus, vaccinia virus, semliki forest virus and adeno-associated virus vector, all of which are well known and can be purchased from commercial sources (Promega, Madison Wis.; Stratagene, La Jolla Calif.; GIBCO/BRL, Gaithersburg Md.). If desired, the vector can be linearized and modified according to a method of the invention, for example, using a PCR method, to contain a topoisomerase recognition site, or cleavage product thereof, at one or both 3' termini, or can be constructed by one skilled in the art (see, generally, *Meth. Enzymol.*, Vol. 185, Goeddel, ed. (Academic Press, Inc., 1990); Jolly, *Canc. Gene Ther.* 1:51–64, 1994; Flotte, *J. Bioenerg. Biomemb.* 25:37–42, 1993; Kirshenbaum et al., *J. Clin. Invest.* 92:381–387, 1993; each of which is incorporated herein by reference).

Viral expression vectors can be particularly useful where a method of the invention is practiced for the purpose of generating a ds recombinant nucleic acid molecule covalently linked in one or both strands, that is to be introduced into a cell, particularly a cell in a subject. Viral vectors provide the advantage that they can infect host cells with relatively high efficiency and can infect specific cell types or can be modified to infect particular cells in a host.

Viral vectors have been developed for use in particular host systems and include, for example, baculovirus vectors, which infect insect cells; retroviral vectors, other lentivirus vectors such as those based on the human immunodeficiency virus (HIV), adenovirus vectors, adeno-associated virus (AAV) vectors, herpesvirus vectors, vaccinia virus vectors, and the like, which infect mammalian cells (see Miller and Rosman, *BioTechniques* 7:980–990, 1992; Anderson et al., *Nature* 392:25–30 Suppl., 1998; Verma and Somia, *Nature* 389:239–242, 1997; Wilson, *New Engl. J. Med.* 334:1185–1187 (1996), each of which is incorporated herein by reference). For example, a viral vector based on an HIV can be used to infect cells, a viral vector based on an adenovirus can be used, for example, to infect respiratory epithelial cells, and a viral vector based on a herpesvirus can be used to infect neuronal cells. Other vectors, such as AAV vectors can have greater host cell range and, therefore, can be used to infect various cell types, although viral or non-viral vectors also can be modified with specific receptors or ligands to alter target specificity through receptor mediated events.

The present invention also provides methods for preparing recombinant nucleic acid molecules containing viral nucleic acid sequences, as well as covalently linked recombinant nucleic acid molecules prepared by such methods and compositions containing the recombinant nucleic acid molecules. Viral vectors derived from adenoviruses, for example, have been used for introducing expressible polynucleotides into cells, including in methods of gene therapy. Adenoviral vectors are particularly attractive vehicles for delivering genes into respiratory epithelial cells. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells (see Kozarsky and Wilson, *Curr. Opin. Genet. Develop.* 3:499–503, 1993, presenting a review of adenovirus-based gene therapy; Bout et al., *Human Gene Ther.* 5:3–10, 1994, demonstrating the use of adenovirus vectors to transfer genes to the respiratory epithelia of rhesus monkeys; see, also, Rosenfeld et al., *Science* 252:431–434, 1991; Rosenfeld et al., *Cell* 68:143–155, 1992; Mastrangeli et al., *J. Clin. Invest.* 91:225–234, 1993; Internatl. Publ. Nos. WO94/12649 and WO 96/17053; U.S. Pat. No. 5,998,205; and Wang et al., *Gene Ther.* 2:775–783, 1995, each of which is incorporated herein by reference. Accordingly, the present invention provides methods of generating vectors containing adenoviral sequences, and further provides methods of using such adenoviral vectors for introducing a polynucleotide into cells such as respiratory epithelial cells.

Viral vectors derived from adeno-associated viruses (AAV) and herpesviruses also can be used for introducing a polynucleotide into cells, particularly mammalian cells, in vitro and in vivo, for example, for a gene therapy procedure (Walsh et al., *Proc. Soc. Exp. Biol. Med.* 204:289–300, 1993; U.S. Pat. No. 5,436,146; Wagstaff et al., *Gene Ther.* 5:1566–70, 1998, each of which is incorporated herein by reference). For example, viral vectors derived from herpesvirus are particularly useful for applications where it is desired to introduce and express a polynucleotide in nerve cells. Accordingly, the present invention also provides methods of generating vectors containing herpesvirus or AAV nucleotide sequences, and further provides methods of using such viral vectors for introducing a polynucleotide into cells.

As such, the present invention provides methods for preparing recombinant nucleic acid molecules having one or more functional properties of viral vectors (e.g., adenoviral vectors, alphaviral vectors, herpes viral vectors, AAV vectors, etc.). In particular embodiments, methods of the invention include the covalently linking nucleotide sequences, wherein one or more of the nucleotide sequences contains regions of a viral genome that confer a function characteristic of the virus from which the nucleotide sequence was derived, for example, the ability to replicate in one or few specific host cells, the ability to be packaged into viral particles, and the like.

In particular embodiments, the invention includes methods for preparing adenoviral vectors by covalently linking at least one (e.g., one, two, three, four, etc.) nucleotide sequence comprising adenoviral sequences to one or more other nucleotide sequences. Specific examples of adenoviral vectors and nucleotide sequences that can be used to prepare adenoviral vectors are disclosed in U.S. Pat. Nos. 5,932,210, 6,136,594, and 6,303,362, each of which is incorporated herein by reference. Adenoviral vectors prepared by methods of the invention can be replication competent or replication deficient. For example, when a replication deficient adenoviral vector is desired, the adenoviral nucleotide sequence can contain deletions of all or part of one or more of the E1a region, the E1b region, and the E3 region. Adenoviral vectors containing deletions of these regions are described, for example, in U.S. Pat. No. 6,136,594. Accordingly, adenoviral vectors prepared by methods of the invention are provided, as are compositions containing the vectors, and uses of such vectors, for example, use of the adenoviral vectors to deliver a heterologous polynucleotide to cells of a mammal (e.g., a human). Thus, the invention provides methods for preparing vectors suitable for use in gene therapy protocols. Typically, such vectors are replication deficient.

In specific embodiments, adenoviral vectors of the invention comprise substantially the entire adenoviral genome, except that one or more of the E1a region, the E1b region, and the E3 region are deleted. In further specific embodiments, non-adenoviral nucleotide sequences can be present in one or more of the E1a region, the E1 region, and the E3 region. In particular embodiments, adenoviral vectors prepared by methods of the invention contain at least one origin of replication and/or a selection marker, for example, a prokaryotic origin of replication, which allows for amplification of the vector in prokaryotic cells such as E. coli cells.

As described above, AAV and herpesvirus vectors also can be prepared according to the methods of the invention. In addition, the alphaviral vectors (e.g., Sindbis virus vectors, Semliki Forest virus vectors, Ross River virus vectors, Venezuelan equine encephalitis virus vectors, Western equine encephalitis virus vectors, Eastern equine encephalitis virus vectors, etc.) can be prepared according to a method of the invention. As such, the present invention provides herpesvirus vectors, AAV vectors, alphaviral vectors, and the like, prepared by such methods, compositions containing such viral vectors, and methods of using the viral vectors.

In particular embodiments, the invention includes methods for preparing alphaviral vectors by covalently linking at least one nucleotide sequence comprising alphaviral sequences to one or more other nucleotide sequences. Specific examples of alphaviral vectors and nucleotide sequences thereof useful for preparing alphaviral vectors are described in U.S. Pat. Nos. 5,739,026 and 6,224,879; Gibco/BRL Instruction Manual No. 10179-018, "SFV Gene Expression System" (Gaithersburg Md.); and Invitrogen Sindbis Expression System manual, catalog no. K750-01 (version E; Carlsbad Calif.), each of which is incorporated herein by reference. In specific embodiments, alphavirus nucleotide sequences used in methods of the invention to prepare alphaviral vectors contain one or more packaging signals, which can, but need not, be of alphaviral origin; one or more subgenomic promoters; one or more nucleotide sequences encoding a non-structural protein such as nsp1, nsp2, nsp3, nsp4, etc.; and combinations thereof.

Alphaviral vectors of the invention can be introduced into cells as DNA or RNA molecules. When DNA forms of the vectors are introduced into cells, expression control sequences (e.g., inducible, repressible or constitutive expression control sequences) can be used to generate RNA molecules, from which one or more non-structural proteins can be translated. In specific embodiments, the non-structural proteins form an RNA dependent RNA polymerase that can amplify RNA molecules corresponding to all or a portion of the transcript generated from the DNA form of the alphaviral vector. As such, these non-structural proteins can catalyze the production of additional copies of RNA molecules from RNA templates, resulting in RNA amplification. Further, one or more nucleotide sequences, for which high levels of expression are desired, can be operatively linked to a subgenomic promoter, thus resulting in the production of high levels of RNA corresponding to the one or more nucleotide sequences.

In an exemplary embodiment, alphaviral vectors prepared by methods of the invention comprise DNA, wherein an inducible promoter directs transcription of an RNA molecule encoding nsp1, nsp2, nsp3, and nsp4 of a Sindbis virus, and wherein a Sindbis subgenomic promoter is operatively linked to a nucleotide sequence that is not of Sindbis viral origin. The invention also provides alphaviral vectors prepared by methods of the invention, methods of using such alphaviral vectors, and compositions containing such alphaviral vectors.

The invention further provides methods for covalently linking nucleotide sequences, wherein one or more of the nucleotide sequences contains one or more (e.g., one, two, three, four, etc.) viral packaging signals (e.g., one or more packaging signal derived from a virus referred to above). The presence of such packaging signals directs the packaging of the recombinant nucleic acid molecule viral vector prepared by methods of the invention. One method for preparing packaged viral vectors is by introducing or expressing the viral vectors, which are prepared according to a method of the invention, into packaging cell lines, which express proteins suitable for the production of virus-like particles. Accordingly, the invention provides packaged recombinant nucleic acid molecules of the invention, methods for preparing such packaged nucleic acid molecules, and compositions containing the packaged nucleic acid molecules.

It will be recognized that a nucleotide sequence to be covalently linked to one or more other nucleotide sequences according to a method of the invention can be any nucleotide sequence, and generally is a nucleotide sequence providing some desirable structural or functional feature to the covalently linked recombinant nucleic acid molecule generated thereby. For example, the nucleotide sequence can contain a restriction endonuclease site or recombinase recognition site, or can comprise a multiple cloning site, which contains two or more restriction endonuclease site or recombinase recognition site or combinations thereof. As such, the present invention also provides methods for preparing a covalently linked recombinant nucleic acid molecule containing one or more (e.g., one, two, three, four, five, six, etc.) multiple cloning sites, which can be the same or different, and can be adjacent to each other or separated by one or more other nucleotide sequences in the covalently linked recombinant nucleic acid molecule. Thus, one or more nucleotide sequences used in a method of the invention can comprise one or more multiple cloning sites. One or more multiple cloning sites also can be added to nucleotide sequences used to prepare the recombinant nucleic acid molecules, for example, by attaching linkers that contain the one or more multiple cloning sites. In related aspects, the invention includes recombinant nucleic acid molecules that are prepared by methods of the invention and contain one or more multiple cloning sites, as well as the use of one or more these multiple cloning sites to modify recombinant nucleic acid molecules prepared by methods of the invention. The invention also provides recombinant nucleic acid molecules produced by such a method, as well as uses of these molecules and compositions containing these molecules. In one embodiment, the generated recombinant nucleic acid molecule further comprises nucleotides sequences that allow the recombinant nucleic acid molecule to function as a vector, for example, viral nucleotide sequences such as adenovirus, herpesvirus, retrovirus, AAV, or alphavirus nucleotide sequences.

Nucleotide sequences useful in a method of the invention also can also comprise or encode one or more operators.

Operators are well known in the art and include, for example, the tryptophan operator of the tryptophan operon of *E. coli*. The tryptophan repressor, when bound to two molecules of tryptophan, binds to the *E. coli* tryptophan operator and, when suitably positioned (i.e., operatively linked) with respect to the promoter, blocks transcription. Another example of an operator suitable for use with the invention is operator of the *E. coli* tetracycline operon. Components of the tetracycline resistance system of *E. coli* can function in eukaryotic cells and are useful for regulating gene expression in eukaryotic cells, for example, mammalian cells such as human cells. The tetracycline repressor, which binds to tetracycline operator in the absence of tetracycline and represses gene transcription, also has been expressed in plant cells at sufficiently high concentrations to repress transcription from a promoter containing tetracycline operator sequences (Gatz et al., *Plants* 2:397–404, 1992). Tetracycline regulated expression systems are described, for example in U.S. Pat. No. 5,789,156, which is incorporated herein by reference. Additional examples of operators that can be used in a method or to generate a composition of the invention include the Lac operator and the operator of the molybdate transport operator/promoter system of *E. coli* (see, for example, Cronin et al., *Genes Devel.* 15:1461–1467, 2001; Grunden et al., *J. Biol. Chem.* 274:24308–24315, 1999, each of which is incorporated herein by reference).

Thus, in particular embodiments, the invention provides methods for preparing covalently linked recombinant nucleic acid molecules that contain one or more operators, which can be used to regulate expression of an operatively linked expressible polynucleotide in prokaryotic cells or eukaryotic cells. As will be recognized, when such a recombinant nucleic acid molecule, which contains an operator, is placed under conditions in which transcriptional machinery is present, either in vivo or in vitro, regulation of expression of an operatively linked polynucleotide can be modulated by contacting the nucleic acid molecule with a repressor and one or more metabolites that facilitate binding of an appropriate repressor to the operator. Accordingly, the present invention further provides methods for preparing covalently linked recombinant nucleic acid molecules that encode one or more repressors, which modulate the function of operators, as well as the recombinant nucleic acid molecules produced by such methods, compositions containing the recombinant nucleic acid molecules, and uses of the recombinant nucleic acid molecules and the compositions.

A method of the invention can be used to operatively covalently link a first ds nucleotide sequence containing an open reading frame to a second (and other) ds nucleotide sequence containing an open reading frame such that a nucleic acid molecule encoding a chimeric polypeptide is generated. The chimeric polypeptide comprises a fusion polypeptide, in which the two (or more) encoded peptides (or polypeptides) are translated into a single product, i.e., the peptides are covalently linked through a peptide bond. For example, a first ds nucleotide sequence can encode a cell compartmentalization domain, such as a plasma membrane localization domain, a nuclear localization signal, a mitochondrial membrane localization signal, an endoplasmic reticulum localization signal, or the like, or a protein transduction domain such as the human immunodeficiency virus TAT protein transduction domain, which can facilitate translocation of a peptide linked thereto into a cell (see Schwarze et al., *Science* 285:1569–1572, 1999; Derossi et al., *J. Biol. Chem.* 271:18188, 1996; Hancock et al., *EMBO J.* 10:4033–4039, 1991; Buss et al., *Mol. Cell. Biol.* 8:3960–3963, 1988; U.S. Pat. No. 5,776,689 each of which is incorporated herein by reference). Such a domain can be useful to target a fusion polypeptide comprising the domain and a polypeptide encoded by a second ds nucleotide sequence, to which it is covalently linked according to a method of the invention, to a particular compartment in the cell, or for secretion from or entry into a cell. As such, the invention provides a means to generate ds recombinant nucleic acid molecules covalently linked in both strands that encode a chimeric polypeptide.

A fusion polypeptide expressed from a nucleic acid molecule generated according to a method of the invention also can comprise a peptide having the characteristic of a detectable label or a tag such that the express fusion polypeptide can be detected, isolated, or the like. For example, a ds nucleotide sequence containing a topoisomerase recognition site, or cleavage product thereof, as disclosed herein, can encode an enzyme such as alkaline phosphatase, β-galactosidase, chloramphenicol acetyltransferase, luciferase, or other enzyme; or can encode a peptide tag such as a polyhistidine sequence (e.g., hexahistidine), a V5 epitope, a c-myc epitope; a hemagglutinin A epitope, a FLAG epitope, or the like. Expression of a fusion polypeptide comprising a detectable label can be detected using the appropriate reagent, for example, by detecting light emission upon addition of luciferin to a fusion polypeptide comprising luciferase, or by detecting binding of nickel ion to a fusion polypeptide comprising a polyhistidine tag. Similarly, isolation of a fusion polypeptide comprising a tag can be performed, for example, by passing a fusion polypeptide comprising a myc epitope over a column having an anti-c-myc epitope antibody bound thereto, then eluting the bound fusion polypeptide, or by passing a fusion polypeptide comprising a polyhistidine tag over a nickel ion or cobalt ion affinity column and eluting the bound fusion polypeptide. Methods for detecting or isolating such fusion polypeptides will be well known to those in the art, based on the selected detectable label or tag (see, for example, Hopp et al., *BioTechnology* 6:1204, 1988; U.S. Pat. No. 5,011,912; each of which is incorporated herein by reference).

A method of the invention also can be used to detectably label a nucleotide sequence with a chemical or small organic or inorganic moiety such that the nucleotide sequence is useful as a probe. For example, a ds nucleotide sequence, which has a topoisomerase recognition site, or cleavage product thereof, at a 3' terminus, can have bound thereto a detectable moiety such as a biotin, which can be detected using avidin or streptavidin, a fluorescent compound (e.g., Cy3, Cy5, Fam, fluorescein, or rhodamine), a radionuclide (e.g., sulfur-35, technicium-99, phosphorus-32, or tritium), a paramagnetic spin label (e.g., carbon-13), a chemiluminescent compound, or the like, such that, upon generating a covalently linked double stranded recombinant nucleic acid molecule according to a method of the invention, the generated nucleic acid molecule will be labeled. Methods of detectably labeling a nucleotide sequence with such moieties are well known in the art (see, for example, Hermanson, "Bioconjugate Techniques" (Academic Press 1996), which is incorporated herein by reference). Furthermore, a detectable label can be used to allow capture of a ds nucleic acid molecule that is generated by the present invention. Finally, a detectable label, for example biotin, can be used to block ligation of a topoisomerase-charged end of a first ds nucleotide sequence to a labeled end of a second ds nucleotide sequence, thus providing a method to direct ligation to the unlabelled end of the second ds nucleotide sequence. It should be recognized that such elements as disclosed herein or otherwise known in the art, including nucleotide sequences encoding cell compartmentalization domains, or detectable labels or tags, or comprising transcriptional or translation regulatory elements can be useful components of a kit as disclosed herein.

A method of the invention provides a means to conveniently generate ds recombinant nucleic acid molecules that encode chimeric polypeptides useful, for example, for performing a two hybrid assay. In such a method, the first ds nucleotide sequence encodes a polypeptide, or a relevant domain thereof, that is suspected of having or being examined for the ability to interact specifically with one or more other polypeptides. The first ds nucleotide sequence is modified as disclosed herein to contain a topoisomerase recognition site at one or both ends and, if desired, a 5' overhanging sequence. The second ds nucleotide sequence, to which the first ds nucleotide sequence is to be covalently-linked according to a method of the invention, can encode a transcription activation domain or a DNA binding domain (Example 2.C), and contains a topoisomerase recognition site, or cleavage product thereof, and a 5' overhanging sequence complementary to that at the end of the first ds nucleotide sequence to which it is to be linked. Upon contact with a topoisomerase, if the nucleotide sequences are not already topoisomerase-charged, a first hybrid useful for performing a two hybrid assay (see, for example, Fields and Song, *Nature* 340:245–246, 1989; U.S. Pat. No. 5,283,173; Fearon et al., *Proc. Natl. Acad. Sci., USA* 89:7958–7962, 1992; Chien et al., *Proc. Natl. Acad. Sci., USA* 88:9578–9582, 1991; Young, *Biol. Reprod.* 58:302–311(1998), each of which is incorporated herein by reference), or modified form of a two hybrid assay such as the reverse two hybrid assay (Leanna and Hannink, *Nucl. Acids Res.* 24:3341–3347, 1996, which is incorporated herein by reference), the repressed transactivator system (U.S. Pat. No. 5,885,779, which is incorporated herein by reference), the protein recruitment system (U.S. Pat. No. 5,776,689, which is incorporated herein by reference), and the like, is generated. Similar methods are used to generate the second hybrid protein, which can comprise a plurality of polypeptides to be tested for the ability to interact with the polypeptide, or domain thereof, of the first hybrid protein.

Similarly, such a method of generating a chimeric protein can be performed according to a method of the current invention for generating a ds recombinant nucleic acid molecule covalently linked in one strand, using first and second ds nucleotide sequences comprising a site-specific topoisomerase recognition site (e.g., a type IA or a type II topoisomerase recognition site), or cleavage product thereof, at least at one 5' terminus of an end to be joined, wherein the ds nucleotide sequences can further comprise complementary 3' overhangs upon cleavage by the topoisomerase.

Similarly, such a method of generating a chimeric protein can be performed according to a method of the current invention for generating a ds recombinant nucleic acid molecule covalently linked in both strands using first and second ds nucleotide sequences comprising a topoisomerase recognition site, or cleavage product thereof, at least at the 5' terminus of the ends to be joined, wherein the ds nucleotide sequences can further comprise complementary 3' overhangs upon cleavage by the topoisomerase; or one of the first or second ds nucleotide sequences can comprise topoisomerase recognition sites, or cleavage products thereof, at the 5' terminus and the 3' terminus of at least one end, and the other ds nucleotide sequence can contain a 3' hydroxyl group and a 5' hydroxyl group at the end to be joined, and wherein, upon cleavage by the topoisomerases, the topoisomerase-charged ds nucleotide sequence can contain a 5' or 3' overhang that is complementary to, and facilitates hybridization to, a 5' or 3' overhang, respectively, at the end of the other ds nucleotide sequence to be joined.

As disclosed herein, a first ds nucleotide sequence can be one of a plurality of nucleotide sequences, for example, a cDNA library, a combinatorial library of nucleotide sequences, or a population of variegated nucleotide sequences. As such, a particularly useful embodiment of a method of the invention is in generating recombinant polynucleotides encoding chimeric polypeptides for performing a high throughput two hybrid assay for identifying protein—protein interactions that occur among populations of polypeptides (see U.S. Pat. No. 6,057,101 and U.S. Pat. No. 6,083,693, each of which is incorporated herein by reference). In such a method, two populations (pluralities) of nucleotide sequences encoding polypeptides are examined, each plurality having a complexity of from a few related but different nucleotide sequences to as high as tens of thousands of such sequences. By performing a method of the invention, for example, using a PCR primer pair to amplify each nucleotide sequence in the plurality, wherein at least one primer of the PCR primer pair comprises at least a topoisomerase recognition site or complement thereof, covalently linked recombinant polynucleotides encoding a population of chimeric bait polypeptides and a population of chimeric prey polypeptides readily can be generated by contacting the amplified pluralities of nucleotide sequences, each of which comprises a topoisomerase recognition site, with a topoisomerase and a nucleotide sequence, which contains a topoisomerase recognition site and encodes a transcription activation domain or a DNA binding domain.

In practicing a method of the invention, a first ds nucleotide sequence also can encode a ribonucleic acid (RNA) molecule, which can function, for example, as a riboprobe, an antisense nucleotide sequence, a ribozyme, a triplexing nucleotide sequence, interference RNA (RNAi), or a suppressor tRNA, or can be used in an in vitro translation reaction, and the second ds nucleotide sequence can encode a regulatory element useful for expressing an RNA from the first nucleotide sequence (see Example 2.A). For example, where it is desired to produce a large amount of RNA, a second ds nucleotide sequence component for performing a method of the invention can comprise an RNA polymerase promoter such as a T7, T3 or SP6 RNA polymerase promoter. Where the RNA molecule is to be expressed in a cell, for example, an antisense molecule to be expressed in a mammalian cell, the second (or other) ds nucleotide sequence can include a promoter that is active in a mammalian cell, particularly a tissue specific promoter, which is active only in a target cell. Furthermore, where the RNA molecule is to be translated, for example, in a coupled in vitro transcription/translation reaction, the first nucleotide sequence or second (or other) nucleotide sequence can contain appropriate translational regulatory elements (see Example 2.B).

The methods of the invention can be used, for example, to generate covalently linked recombinant nucleic acid molecules that encode suppressor tRNA molecules. The nucleotide sequence encoding the suppressor tRNA can be operatively linked to an expression control element, particularly a transcriptional promoter, which can be constitutively active or inducible, and can be operative in prokaryotic cells or eukaryotic cells. In addition, the same recombinant nucleic acid molecule or a different recombinant nucleic acid molecule can contain a first and second coding sequence, which are separated by a nucleotide sequence containing a STOP codon that can be suppressed by the suppressor tRNA. Expression of the suppressor tRNA can then suppress the STOP codon, thereby allowing the generation of fusion protein. For example, where the suppressor tRNA is expressible from an inducible promoter, the system, which can be introduced into a cell, provides a means to express a polypeptide encoded by the first coding sequence (in the absence of expression of the suppressor tRNA) or a fusion protein comprising the polypeptide encoded by the first coding sequence operatively linked to the polypeptide encoded by the second coding sequence (in the presence of expression of the suppressor tRNA), as desired, simply by including or excluding the inducing agent specific for the inducible promoter. The polypeptides of such a system can be any polypeptide as exemplified herein or otherwise known in the art.

Methods of the invention may also be used to produce constructs which allow for silencing of genes in vivo. One method of silencing genes involves the production of double stranded RNAi (see, for example, Mette et al., *EMBO J.* 19:5194–5201, 2000, which is incorporated herein by reference). The mechanism by which RNAi is believed to function, which is reviewed in Fjose et al., *Biotechnol. Ann. Rev.* 7:31–57, 2001, appears to be based on the ability of double stranded RNA to induce the degradation of specific RNA molecules. This mechanism is reported to involve the conversion of double-stranded RNA into short RNAs that direct ribonucleases to homologous RNA targets (e.g., mRNA targets). Methods of the invention can be used in a number of ways to produce molecules such as RNAi. Thus, expression products of nucleic acid molecules of the invention can be used to silence gene expression.

One example of a nucleic acid molecule designed to produce RNAi is a molecule in which a nucleic acid segment is linked to one or more promoters such that RNA corresponding to both strands are produced as two separate transcripts or as part of the same transcript. For example, two separate RNA polymerase promoters, which can be the same or different (e.g., a T7 promoter and/or an SP6 promoter) can be located 5' and 3' to a polynucleotide sequence encoding a polypeptide. Further, the RNA polymerase promoters can be operatively linked to the expressible polynucleotide such that transcription driven by each promoter results in the production of RNA corresponding to each strand of the expressible polynucleotide. Thus, transcription from one promoter results in the production of a sense RNA and transcription from the other promoter results in the production of an antisense RNA. Since the RNA strands are complementary, they can hybridize to each other under physiological conditions to produce an RNAi molecule.

Another example of a recombinant nucleic acid molecule that can be used to produce RNAi is one in which an open reading frame is flanked on each end by promoters that drive transcription of the open reading frame in opposing directions. As a third example, double stranded RNA can be produced from a recombinant nucleic acid molecule encoding an RNA molecule having a "snapback" region (e.g., a region that is six, seven, eight, nine ten, etc. nucleotides in length) at one terminus. Such an RNA transcript can form a hairpin turn at or near one terminus and, when incubated under appropriate conditions in the presence of an RNA dependent RNA polymerase, the double stranded region formed by the hairpin can prime second strand synthesis to form a double stranded RNA molecule such as an RNAi molecule.

Nucleotide sequence designed to produce RNAi from a recombinant nucleic acid molecules as described above can, but need not, correspond to the entire coding sequence of a gene (i.e., at least the portion containing all of the exons) or a full length open reading frame (ORF). For example, when the nucleotide sequence corresponds to a portion of an ORF and, therefore, encodes an RNA molecule that does not correspond to all of the ORF, the nucleotide sequence can include at least about 15 (e.g., about 20, about 30, about 40, about 50, about 60, etc.) nucleotides, for example, at least about 15 to about 30 (e.g., 15, 16, 17, 18, 19, 20, 21, 22, 23, 24, 25, 26, 27, 28, 29, or 30) nucleotides at the 5' end of the ORF, the 3' end of the ORF, or internal to the ORF. Thus, in particular embodiments, the invention provides methods for preparing recombinant nucleic acid molecules containing at least three covalently operatively linked nucleotide sequences. In some embodiments, at least two of the nucleotide sequences share at least one region of sequence identity (e.g., a region at least about 20, at least about 30, at least about 40, at least about 50, at least about 60, at least about 70, at least about 80, at least about 90, at least about 100 nucleotides, etc.) nucleotides in length, for example, a region of about 15 to 30 (e.g., 15, 16, 17, 18, 19, 20, 21, 22, 23, 24, 25, 26, 27, 28, 29, or 30) nucleotides in length. In other embodiments, one nucleotide sequence is flanked by a region that can confer transcription from the interior portion of the nucleotide sequence molecule in opposing directions, thus allowing the generation of sense and antisense RNA transcripts. As such, the invention provides covalently linked recombinant nucleic acid molecules prepared by methods of the invention, and further provides methods of using of such molecules to either inhibit gene expression or facilitate degradation of specific target RNA molecules.

The invention also provides methods for generating covalently linked recombinant nucleic acid molecules that can be used to express antisense RNA (e.g., antisense mRNA). Methods similar to those described above for the production of RNAi can be employed, although only the non-coding strand generally will be transcribed, thereby generating antisense RNA molecules.

Gene silencing methods involving the use of compounds such as RNAi and antisense RNA, for example, are particularly useful for identifying gene functions. More specifically, gene silencing methods can be used to reduce or inhibit the expression of one or more genes in a cell or organism. Phenotypic manifestations associated with the selective inhibition of gene functions can then be used to assign role to the "silenced" gene or genes. As an example, Chuang et al. (*Proc. Natl. Acad. Sci., USA* 97:4985–4990, 2000) demonstrated that in vivo production of RNAi can alter gene activity in *Arabidopsis thaliana*. Thus, the invention provides methods for regulating expression of nucleic acid molecules in vivo (e.g., in cells and tissues) and/or in vitro by expressing RNAi molecules, antisense RNA molecules, or a combination thereof. The invention further provides methods for preparing covalently linked recombinant nucleic acid molecules useful for producing RNA that corresponding to one or both strands of an expressible polynucleotide.

In related embodiments, promoters that drive transcription of a sense RNA or antisense RNA can be either constitutive (e.g., CMV promoter, SV40 promoter, etc.), inducible (e.g., a metallothionein promoter, etc.), or repressible. Thus, for example, two different inducible promoters can be used to drive transcription of sense RNA and antisense RNA. In such an instance, promoter activation can be used to induce production of sense RNA, antisense RNA, or both sense RNA and antisense RNA. Further, the amount of sense RNA and/or antisense RNA produced can be related by using, for example, graduated induction and/or derepression of the promoters.

The invention also relates to methods of generating a covalently linked recombinant nucleic acid molecule encoding a ribozyme, as well as to compositions containing such recombinant nucleic acid molecules and methods of using such molecules for gene silencing. In particular, the invention provides antisense RNA/ribozymes fusions, which comprise 1) antisense RNA corresponding to a target gene and 2) one or more ribozymes that cleave RNA (e.g., hammerhead ribozyme, hairpin ribozyme, delta ribozyme, Tetrahymena L-21 ribozyme, etc.). Further provided by the invention are vectors that express such fusions, methods for producing such vectors, and methods for using such vector to suppress gene expression.

Expression of antisense molecules fused to ribozymes can be used, for example, to cleave specific RNA molecules in a cell because the antisense RNA portion of the transcript can be designed to hybridize to particular mRNA molecules. Further, the ribozyme portion of the transcript can be designed to cleave the RNA molecule to which it has hybridized. For example, the ribozyme can be one which cleaves double stranded RNA (e.g., a Tetrahymena L-21 ribozyme).

The present invention further provides nucleotide sequences suitable for performing cloning reactions in which a first nucleotide, which shares one or more regions of homology with a second nucleotide sequence, is used to insert all or a portion of the second nucleotide sequence into the first nucleotide sequence. The invention further provides compositions and methods for performing such cloning reactions.

One example of such a process is RecE/T cloning (see Internatl. Publ. No. WO 01/04288, which is incorporated herein by reference). Typically, in RecE/T cloning, a linear first nucleotide sequence (e.g., a vector) is introduced into a cell that contains 1) regions at the termini that share homology with two separate nearby regions (e.g., regions that are about 20 to 30, or about 20 to 40, or about 20 to 50, or about 30 to 40, or about 40 to 50, or about 40 to 60, or about 40 to 80, or about 50 to 90, etc. nucleotides in length) of a second nucleotide sequence, which is present in the cell (e.g., a plasmid, a bacterial artificial chromosome, a natural chromosome, etc.), 2) a selection marker, and 3) an origin of replication. The linear first nucleotide sequence generally replicates only if it becomes circularized. Further, the first nucleotide sequence typically becomes circularized upon undergoing recombination with the second nucleotide sequence and acquiring a portion of the second nucleotide sequence, which is intervening between the regions of homology. In such embodiments, the regions of homology in the first nucleotide sequence will typically be in a reverse orientation as compared to the second nucleotide sequence. Generally, the cell in which recombination occurs is one that expresses a recombinase such as RecE/T or RedAlpha/Beta. Thus, the invention provides, in part, methods for performing RecE/T cloning, covalently linked ds recombinant nucleic acid molecules prepared by such methods, compositions comprising such recombinant nucleic acid molecules, and methods for using such nucleic acid molecules and compositions.

Modifications of the RecE/T process can be used to generate a number of different end products. For example, when the regions of homology are arranged in various ways, the first nucleotide sequence can be designed to 1) insert into the second nucleotide sequence, or 2) delete a portion of the second nucleotide sequence. Typically, when insertion of the second nucleotide sequence into the second nucleotide sequence is desired, the regions of homology of the first nucleotide sequence are in the same orientation with respect to the regions of homology in the second nucleotide sequence. Further, when deletion of nucleic acid from the second nucleotide sequence is desired, the regions of homology of the first nucleotide sequence generally are in an inverse orientation with respect to the regions of homology in the second nucleotide sequence. Also, when insertion of the first nucleotide sequence into the second nucleotide sequence is desired, typically the first nucleotide sequence lacks an origin of replication. Accordingly, the present invention provides methods for performing such processes, as well as nucleotide sequences and compositions for use in the above methods.

A method of the invention can be particularly useful for generating an expressible ds recombinant nucleic acid molecule that can be inserted in a site specific manner into a target DNA sequence. The target DNA sequence can be any DNA sequence, particularly a genomic DNA sequence, and preferably a gene for which some or all of the nucleotide sequence is known. The method can be performed utilizing a first ds nucleotide sequence, which has a first end and a second end and encodes a polypeptide, for example, a selectable marker, wherein the first ds nucleotide sequence comprises a topoisomerase recognition site or cleavage product thereof at the 3' terminus of each end and, optionally, a hydroxyl group at the 5' terminus of each end, and wherein, preferably, the 5' termini comprise 5' overhanging sequences, which are different from each other; and covalently linking the first ds nucleotide sequence to first and second PCR amplification products according to a method of the invention. The first and second amplification products are generated from sequences upstream and downstream of the site at which the construct is to be inserted, and each amplification product contains a topoisomerase recognition site and, preferably, a 5' overhanging sequence, which is generated following contact with the site specific topoisomerase. Preferably, the first and second amplification products have different 5' overhanging sequences such that each can be linked to a predetermined end of the first ds nucleotide sequence. Such a method similarly can be performed using a ds amplification product comprising a topoisomerase recognition site, or cleavage product thereof, at the 5' terminus of one or both ends, wherein, upon cleavage by the topoisomerase, the topoisomerase-charged molecule can comprise a 3' overhang at one or both ends containing the topoisomerase. In addition, the method can be performed using a ds amplification product comprising topoisomerase recognition sites, or cleavage products thereof, at the 5' terminus and the 3' terminus of one or both ends, wherein, upon cleavage by the topoisomerases, the topoisomerase-charged ds nucleotide sequence preferably contains a 5' or 3' overhang at one or both ends containing the topoisomerases.

The first and second amplification products are generated using two sets of PCR primer pairs. The two sets of PCR primer pairs are selected such that, in the presence of an appropriate polymerase such as Taq polymerase and a template comprising the sequences to be amplified, the primers amplify portions of a target DNA sequence that are upstream of and adjacent to, and downstream of and adjacent to, the site for insertion of the selectable marker. In addition, the sets of PCR primer pairs are designed such that the amplification products contain a topoisomerase recognition site and, following cleavage by the site specific topoisomerase, a 5' overhanging sequence at the end to be covalently linked to the selectable marker. As such, the first PCR primer pair includes 1) a first primer, which comprises, in an orientation from 5' to 3', a nucleotide sequence complementary to a 5' overhanging sequence of the end of the selectable marker to which the amplification product is to be covalently linked, a nucleotide sequence complementary to a topoisomerase recognition site, and a nucleotide sequence complementary to a 3' sequence of a target DNA sequence upstream of the insertion site; and 2) a second primer, which comprises a nucleotide sequence of the target genomic DNA upstream of the 3' sequence to which the first primer is complementary, i.e., downstream of the insertion site. The second PCR primer pair includes 1) a first primer, which comprises, from 5' to 3', a nucleotide sequence complementary to the 5' overhanging sequence of the end of the selectable marker to which it is to be covalently linked, a nucleotide sequence complementary to a topoisomerase recognition site, and a nucleotide sequence of a 5' sequence of a target DNA sequence, wherein the 5' sequence of the target genomic DNA is downstream of the 3' sequence of the target DNA sequence to which the first primer of the first PCR primer pair is complementary; and the second primer of the second primer pair comprises a nucleotide sequence complementary to a 3' sequence of the target DNA sequence that is downstream of the 5' sequence of the target genomic DNA contained in the first primer. The skilled artisan will recognize that the sequences of the primer that are complementary to the target genomic DNA are selected based on the sequence of the target DNA.

Upon contact of the ds nucleotide sequence comprising the selectable marker, the first and second amplification products, and a topoisomerase (if the molecules are not topoisomerase-charged), a ds recombinant nucleic acid molecule covalently linked in both strands is generated according to a method of the invention. The generated ds recombinant nucleic acid molecule can be further amplified, if desired, using PCR primers that are specific for an upstream and downstream sequence of the target genomic DNA, thus ensuring that only functional constructs are amplified. The generated ds recombinant nucleic acid molecule is useful for performing homologous recombination in a genome, for example, to knock-out the function of a gene in a cell, or to confer a novel phenotype on the cell containing the generated recombinant nucleic acid molecule. The method can further be used to produce a transgenic non-human organism having the generated ds recombinant nucleic acid molecule stably maintained in its genome.

A method of the invention also is useful for covalently linking, an adapter or linker sequence to one or both ends of a ds nucleotide sequence of interest, including to each of a plurality of ds nucleotide sequences. For example, where it is desired to put linkers on both ends of a first ds nucleotide sequence, the method can be performed by contacting a topoisomerase with a first ds nucleotide sequence, which has a topoisomerase recognition site, or cleavage product thereof, at one or both 3' or 5' termini and which can include hydroxyl groups at both 5' termini; and a second ds nucleotide sequence and at least a third double stranded nucleotide sequence, each of which can include a topoisomerase recognition site, or cleavage product thereof at the appropriate 3' or 5' terminus and which can also include, where desirable, a 5' hydroxyl group at the same terminus. An appropriate terminus is the terminus to which the linker is to be covalently linked in at least one strand to the first nucleotide sequence. In one embodiment, one or both linker sequences contain an overhanging sequence that is complementary to a sequence at the 5' terminus of the end of the first ds nucleotide sequence to which the linker is to be covalently linked, thereby facilitating the initial association of the nucleotide sequences in the proper (predetermined) orientation (see, for example, FIG. 2 and Example 1.B). In performing such a method, the linker sequences comprising the second and at least third nucleotide sequence can be the same or different.

Figure 7:
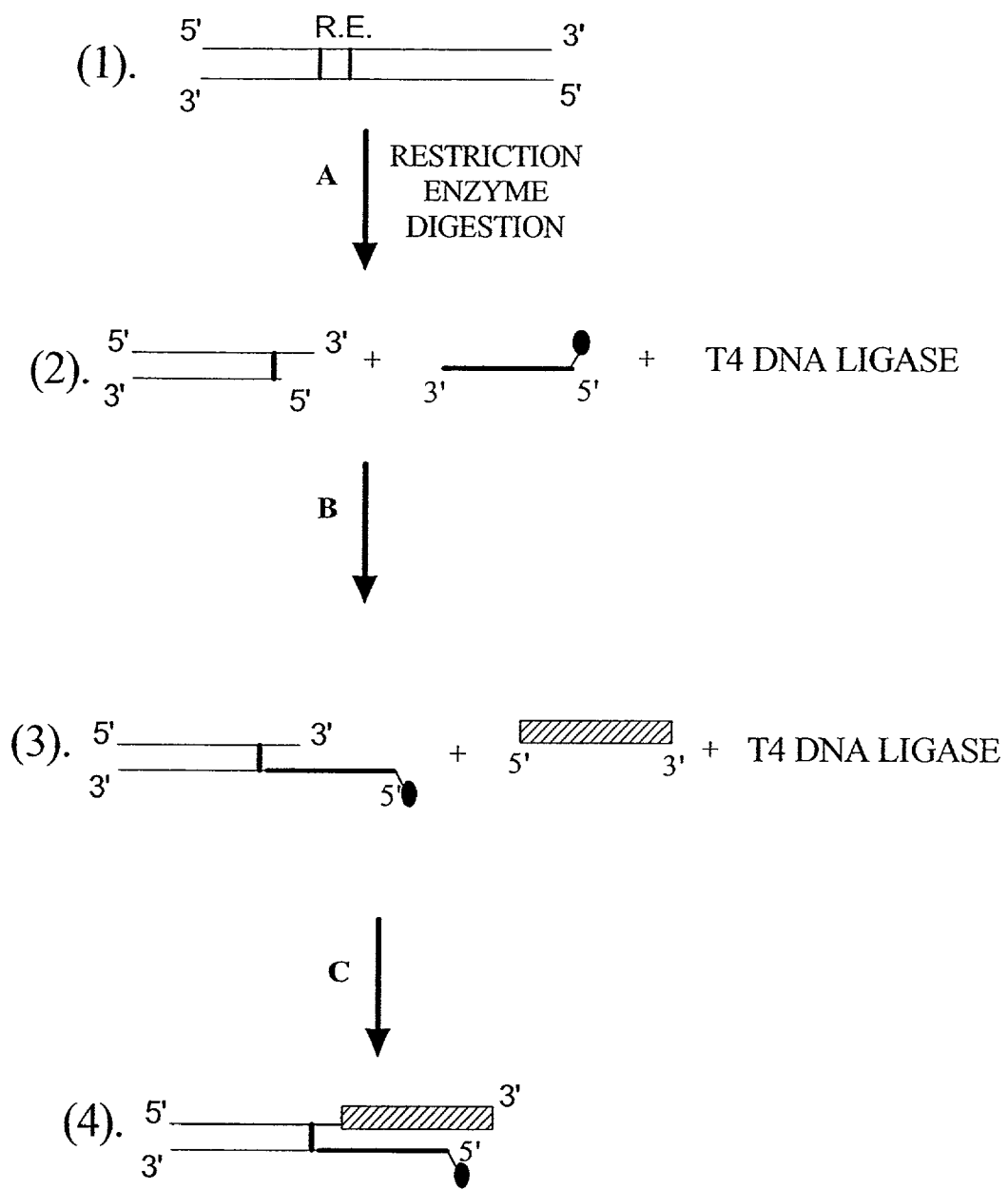
FIG. 7 shows one example of a process for preparing a double stranded nucleic acid molecule which contains a topoisomerase (e.g., a type IA topoisomerase) bound to the 5' terminus of one end of the molecule, wherein the same end of the molecule further comprise a 3' overhang (see (4) in this figure).

FIG. 7 shows one example of a process for preparing a ds nucleotide sequence containing a topoisomerase (e.g., a type IA topoisomerase) bound to the 5' terminus of one end of the sequence, and wherein the same end further comprise a 3' overhang (see (4) in FIG. 7). In step A, a nucleotide sequence to be modified with topoisomerase is digested with a restriction enzyme that generates a "sticky" end. The restricted nucleotide sequence is then contacted in step B with a linear, single stranded nucleotide sequence which contains a topoisomerase attached the 5' terminus and a ligase (e.g., a DNA ligase such as T4 DNA ligase). The linear, single stranded nucleotide sequence also contains a region at the 3' terminus which shares sufficient sequence complementarity to the "sticky" end generated by the restriction enzyme, such that the two molecules will hybridize. Thus, in step B, the two nucleotide sequences are ligated to each other. In step C, the product of the second step is contacted with a third nucleotide sequence which shares sequence complementarity to portions of the linear, single stranded nucleic acid molecule generated in step B, and a ligase. The product of step C, shown in (4), is a ds nucleotide sequence containing a topoisomerase attached to the 5' terminus of one end and a 3' overhang on the same end. It will be recognized that numerous variations of the exemplified method are within the scope of the invention. For example, similar processes can be performed to prepare nucleic acid molecules which comprise topoisomerase attached to the 3' terminus of one end or which have a 5' overhang or are blunt ended at the end to which a topoisomerase is attached. In another example, the nucleotide sequence labeled number 3 in FIG. 7 can be produced in the following manner: a ds nucleotide sequence can be digested with a restriction enzyme to generate a ds nucleotide sequence with a single-stranded 5' overhang that includes a type IA topoisomerase recognition site. The ds nucleotide sequence with the single stranded overhang can then be contacted with type IA topoisomerase to generate a type IA topoisomerase-charged ds nucleotide sequence.

Figure 8:
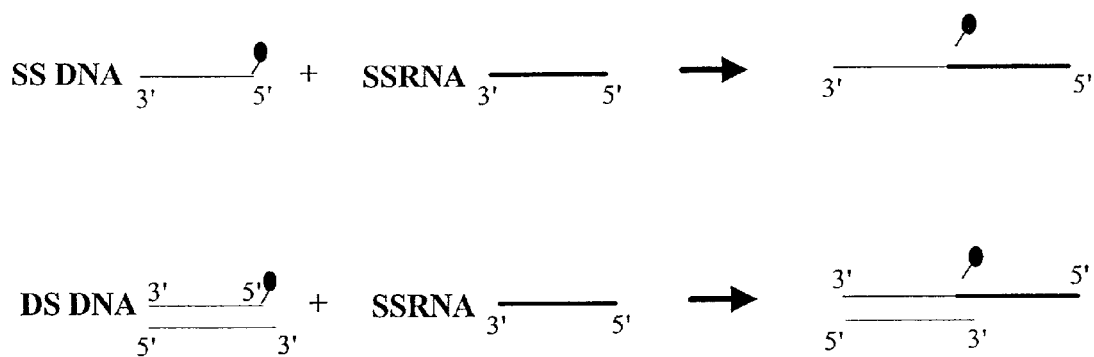
FIG. 8 shows two embodiments of the invention in which a single stranded or double stranded DNA nucleotide sequence is joined with a single stranded RNA nucleotide sequence.

FIG. 8 shows two embodiments of the invention in which single stranded or double stranded DNA is covalently linked to single stranded RNA. Where single stranded DNA is joined to single stranded RNA, the 3' end of the ribonucleotide sequence is covalently linked to the 5' end of the deoxyribonucleotide sequence. Where double stranded DNA is joined to single stranded RNA, the 3' terminus of the ribonucleotide sequence shares sufficient sequence complementarity to the 3' overhang of the deoxyribonucleotide sequence such that the two molecules hybridize. As above, the 3' end of the ribonucleotide sequence is also covalently linked to the 5' end of the deoxyribonucleotide sequence. As will be recognized, numerous variations of the above are within the scope of the invention. For example, the RNA molecule can be double stranded. In another example, all of the nucleotide sequences can be deoxyribonucleotide sequences.

The present invention provides a ds recombinant nucleic acid molecule having, or which can be made to have, a first end and a second end, each end including a 5' terminus and a 3' terminus, wherein the vector comprises a site-specific type IA topoisomerase recognition site at or near a 5' terminus of the first end, the second end, or both the first end and the second end. The ds recombinant nucleic acid molecule can further include a type IB topoisomerase recognition site at or near a 3' termini of an end that does not include a type IA topoisomerase recognition site. The ds recombinant nucleic acid molecule can be a vector.

The present invention further provides a topoisomerase-charged ds recombinant nucleic acid molecule having a first end and a second end, each end having a 5' terminus and a 3' terminus, wherein a site-specific type IA topoisomerase is bound at the 5' terminus of the first end, the second end, or both the first end and the second end. For example, the topoisomerase-charged ds recombinant nucleic acid molecule can include a type IA topoisomerase bound at the 5' termini of each of the first and second ends. The topoisomerase-charged nucleic acid ds recombinant nucleic acid molecule can include a type IB topoisomerase bound at a 3' termini of an end not bound by a type IA topoisomerase. The topoisomerase-charged ds recombinant nucleic acid molecule can be a vector.

The present invention also provides kits, which contain components useful for conveniently practicing the methods of the invention. Kits of the invention can contain any number of components, and generally contain at least two components. For example, a kit of the invention can contain 1) a first nucleotide sequence containing one or more topoisomerase recognition sites, and 2) instructions for covalently linking the first nucleotide sequence to a second (or other) nucleotide sequence using a method as disclosed herein. In particular embodiments, the instructions provide methods for covalently linking two or more nucleotide sequences in one or both strands. For example, the instructions can be for covalently linking two or more ds nucleotide sequences in both strands, and can include instructions for obtaining a second (or other) ds nucleotide sequence that contains a topoisomerase recognition site or that is topoisomerase-charged on one or more termini that are to covalently linked to the first ds nucleotide sequence, or can include instructions for making or obtaining a primer, which can be one of a primer pair, that includes, for example, a nucleotide sequence complementary to a type IB topoisomerase recognition site, such that a terminus of an amplification product generated using such a primer pair (including such a primer) can be covalently linked (in the presence of a type IB topoisomerase) to an end of a first ds nucleotide sequence that has a type IB topoisomerase recognition site at 3' terminus of the end to be linked or that is topoisomerase-charged at that terminus. In a related embodiment, the first nucleotide sequence is topoisomerase adapted (topoisomerase-charged) prior to inclusion in the kit.

In one embodiment, a kit of the invention contains a first ds nucleotide sequence, which encodes a polypeptide, particularly a selectable marker, and contains a topoisomerase recognition site at each end. Preferably, the first nucleotide sequence comprises a topoisomerase-activated nucleotide sequence. More preferably, the topoisomerase-charged first nucleotide sequence comprises a 5' overhanging sequence at each end, and most preferably the 5' overhanging sequences are different from each other. Optionally, each of the 5' termini comprises a 5' hydroxyl group.

In addition, the kit can contain at least a nucleotide sequence (or complement thereof) comprising a regulatory element, which can be an upstream or downstream regulatory element, or other element, and which contains a topoisomerase recognition site at one or both ends. Preferably, the kit contains a plurality of ds nucleotide sequences, each comprising a different regulatory element or other element, for example, a sequence encoding a tag or other detectable molecule or a cell compartmentalization domain. The different elements can be different types of a particular regulatory element, for example, constitutive promoters, inducible promoters and tissue specific promoters, or can be different types of elements including, for example, transcriptional and translational regulatory elements, epitope tags, and the like. Such ds nucleotide sequences can be topoisomerase-activated, and can contain 5' overhangs or 3' overhangs that facilitate operatively covalently linking the elements in a predetermined orientation, particularly such that a polypeptide such as a selectable marker is expressible in vitro or in one or more cell types.

The kit also can contain primers, including first and second primers, such that a primer pair comprising a first and second primer can be selected and used to amplify a desired ds recombinant nucleic acid molecule covalently linked in one or both strands, generated using components of the kit. For example, the primers can include first primers that are complementary to elements that generally are positioned at the 5' end of a generated ds recombinant nucleic acid molecule, for example, a portion of a ds nucleotide sequence comprising a promoter element, and second primers that are complementary to elements that generally are positioned at the 3' end of a generated ds recombinant nucleic acid molecule, for example, a portion of a ds nucleotide sequence comprising a transcription termination site or encoding an epitope tag. Depending on the elements selected from the kit for generating a ds recombinant nucleic acid molecule covalently linked in both strands, the appropriate first and second primers can be selected and used to amplify a full length functional construct.

In another embodiment, a kit of the invention contains a plurality of different elements, each of which can be topoisomerase-activated at one or both ends, and each of which can contain a 51 overhanging sequence or a 3' overhanging sequence or a combination thereof. The 5' or 3' overhanging sequences can be unique to a particular element, or can be common to plurality of related elements, for example, to a plurality of different promoter element. Preferably, the 5' overhanging sequences of elements are designed such that one or more elements can be operatively covalently linked to provide a useful function, for example, an element comprising a Kozak sequence and an element comprising a translation start site can have complementary 5' overhangs such that the elements can be operatively covalently linked according to a method of the invention.

The plurality of elements in the kit can comprise any elements, including transcription or translation regulatory elements; elements required for replication of a nucleotide sequence in a bacterial, insect, yeast, or mammalian host cell; elements comprising recognition sequences for site specific nucleic acid binding proteins such as restriction endonucleases or recombinases; elements encoding expressible products such as epitope tags or drug resistance genes; and the like. As such, a kit of the invention provides a convenient source of different elements that can be selected depending, for example, on the particular cells that a construct generated according to a method of the invention is to be introduced into or expressed in. The kit also can contain PCR primers, including first and second primers, which can be combined as described above to amplify a ds recombinant nucleic acid molecule covalently linked in one or both strands, generated using the elements of the kit. Optionally, the kit further contains a site specific topoisomerase in an amount useful for covalently linking in at least one strand, a first ds nucleotide sequence comprising a topoisomerase recognition site to a second (or other) ds nucleotide sequence, which can optionally be topoisomerase-activated ds nucleotide sequences or nucleotide sequences that comprise a topoisomerase recognition site.

In still another embodiment, a kit of the invention contains a first ds nucleotide sequence, which encodes a selectable marker, and contains a topoisomerase recognition site at each end; a first and second PCR primer pair, which can produce a first and second amplification products that can be covalently linked in one or both strands, to the first ds nucleotide sequence in a predetermined orientation according to a method of the invention. Such a generated construct can be introduced into a cell and can incorporate into the genome of the cell by homologous recombination in a site specific manner, where it can be stably maintained and can express a heterologous polypeptide in the cell or can knock-out a target gene function. A target gene to be knocked-out, for example, can be any gene for which at least part of the sequence is known or can be readily determined and the function of which it is desired to disrupt, for example, an oncogene, a gene involved in apoptosis, a gene encoding a serine/threonine or a tyrosine kinase, or any other gene.

The first PCR primer pair in a kit of the invention useful for generating a ds recombinant nucleic acid molecule covalently linked in both strands, includes a first primer that comprises, in an orientation from 5' to 3', a nucleotide sequence complementary to a 5' overhanging sequence of a ds nucleotide sequence to which it is to be covalently linked (for example, an end of the ds nucleotide sequence encoding the selectable marker), a nucleotide sequence complementary to a topoisomerase recognition site, and a nucleotide sequence complementary to a 3' sequence of the target DNA sequence. The first PCR primer pair also includes a second primer that comprises a nucleotide sequence of the target DNA sequence upstream of the 3' sequence to which the first primer is complementary.

The second PCR primer pair of a kit useful for generating a ds recombinant nucleic acid molecule covalently linked in both strands, includes a first primer that comprises, from 5' to 3', a nucleotide sequence complementary to a 5' overhanging sequence of a ds nucleotide sequence to which it is to be covalently linked, a nucleotide sequence complementary to a topoisomerase recognition site, and a nucleotide sequence of a 5' sequence of the target DNA sequence, wherein the 5' sequence of the target gene is downstream of the 3' sequence of the target DNA sequence to which the first primer of the first primer pair is complementary. The second PCR primer pair also includes a second primer that comprises a nucleotide sequence complementary to a 3' sequence of the target gene that is downstream of the 5' sequence of the target DNA sequence contained in the first primer.

In another embodiment, a kit of the invention useful for generating a ds recombinant nucleic acid molecule covalently linked in both strands contains a first ds nucleotide sequence, which encodes a transcription activation domain and comprises a topoisomerase recognition site, or cleavage product thereof, at a 3' terminus; and a second ds nucleotide sequence, which encodes a DNA binding domain and comprises a topoisomerase recognition site, or cleavage product thereof, at a 3' terminus. Upon cleavage by the site specific topoisomerase, the first or second ds nucleotide sequence can have a 5' overhang, or both sequences can have 5' overhangs, which are the same or are different from each other. Where the ds nucleotide sequences have a 5' overhang, the overhang generally is complementary to a ds nucleotide sequence to which first or second ds nucleotide sequence is to be covalently linked according to a method of the invention. The kit also can contain one or a pair of adapters, linkers or the like, which can comprise a topoisomerase recognition site, or cleavage product thereof, at one or both 3' termini, and, optionally, a hydroxyl group at the same terminus/termini. Such adapters, linkers, or the like are selected such that they contain a 5' overhang that is complementary to one or the other of the two ds nucleotide sequences described above and part of the kit.

Similarly, a kit of the invention can contain one or a pair of adapters, linkers or the like, which comprise a topoisomerase recognition site, or cleavage product thereof, at one or both 5' termini, and, optionally, a hydroxyl group at the same terminus (or termini). Such adapters, linkers, or the like are selected such that they contain a 3' overhang that is complementary to one or the other of the two ds nucleotide sequences described above and part of the kit. In addition, the kit can contain one or a pair of adapters, linkers or the like, which comprise a topoisomerase recognition site, or cleavage product thereof, at one or both 5' and/or 3' termini, and, optionally, a hydroxyl group at the same terminus/termini.

Adapters, linkers, or the like generally are selected such that they contain a 5' and/or a 3' overhang that is complementary to one or the other of the two ds nucleotide sequences as disclosed herein and part of the kit. Such adapters, linkers, or the like can be joined to the ends of ds nucleotide sequences that are to covalently linked to one or the other of the first or second ds nucleotide sequences provided with the kit, thus facilitating the construction of chimeric polynucleotides encoding the bait and prey polypeptides useful in a two hybrid assay. Such a kit also can contain a PCR primer or primer pair, which can be used to prepare an amplified plurality of nucleotide sequences comprising a topoisomerase recognition site, or cleavage product thereof (see Table 1 and Example 1).

A PCR primer pair in a kit of the invention, which can be used for generating a ds recombinant nucleic acid molecule covalently linked in one strand, can include a first primer that comprises, in an orientation from 5' to 3', a nucleotide sequence of a 5' overhanging sequence of a ds nucleotide sequence to which it is to be linked (for example, an end of the ds nucleotide sequence encoding the selectable marker), a topoisomerase recognition site (e.g., a type IA or type II topoisomerase recognition site), and a nucleotide sequence complementary to a 5' sequence of the target DNA sequence. The PCR primer pair also includes a second primer that comprises a nucleotide sequence of the target DNA sequence downstream of the 5' sequence to which the first primer is complementary.

In another embodiment, a kit of the invention contains a first ds nucleotide sequence, which encodes a transcription activation domain and comprises a site-specific topoisomerase recognition site (e.g., a type IA or a type II topoisomerase recognition site), or cleavage product thereof, at a 5' terminus; and a second ds nucleotide sequence, which encodes a DNA binding domain and comprises a site-specific topoisomerase recognition site (e.g., a type IA or a type II topoisomerase recognition site), or cleavage product thereof, at a 5' terminus. Upon cleavage by the site specific topoisomerase, the first or second ds nucleotide sequence can have a 3' overhang, or both sequences can have 3' overhangs, which are the same or are different from each other. Where the ds nucleotide sequences have a 3' overhang, the overhang generally is complementary to a ds nucleotide sequence to which first or second ds nucleotide sequence is to be linked according to a method of the invention. The kit also can contain one or a pair of adapters, linkers or the like, which comprise a site-specific topoisomerase recognition site (e.g., a type IA or a type II topoisomerase recognition site), or cleavage product thereof, at one or both 5' termini, and which can contain a 5' overhang that is complementary to one or the other of the two ds nucleotide sequences of the kit.

A kit of the invention also can contain a first isolated topoisomerase-charged ds nucleotide sequence and at least a second isolated topoisomerase-charged ds nucleotide sequence, wherein the sequences of the first and at least second ds nucleotide sequences are different from each other; or can contain at least two different ds nucleotide sequences, each of which comprises a topoisomerase recognition site at or near one or both ends, and a site specific topoisomerase, which can bind to and cleave the at least two different ds nucleotide sequences at the topoisomerase recognition site; or can contain a site specific topoisomerase and a covalently linked ds recombinant nucleic acid molecule, wherein the covalently linked ds recombinant nucleic acid molecule comprises at least one topoisomerase recognition site for the site specific topoisomerase in each complementary strand, wherein the topoisomerase recognition sites in each complementary strand are within about fifty nucleotides of each other, and wherein the site specific topoisomerase can bind to and cleave the topoisomerase recognition site in each complementary strand. In addition, a kit of the invention can contain a first ds nucleotide sequence, which contains a first end and a second end, and encodes a polypeptide, said first ds nucleotide sequence further comprising a topoisomerase bound at each end; and a plurality of ds nucleotide sequence populations, wherein each ds nucleotide sequence in a population contains a first end and a second end, and comprises a regulatory element, each ds nucleotide sequence further comprising a topoisomerase bound at the first end, the second end or both ends, wherein each population in the plurality is different from each other population, and wherein each ds nucleotide sequence in a population contains the same overhanging sequence, which is different from the overhanging sequence in the ds nucleotide sequences in each other population. Such a kit also can contain PCR primers specific for the ds nucleotide sequences in each population of nucleotide sequences. In one embodiment, the polypeptide encoded by the first ds nucleotide sequence is a selectable marker.

A ds recombinant nucleic acid molecule covalently linked in one or both strands, and generated according to a method of the invention, can be used for various purposes, including, for example, for expressing a polypeptide in a cell, for diagnosing or treating a pathologic condition, or the like. As such, the present invention provides a medicament, which can be useful for treating a pathologic condition by expressing a polypeptide in one or more cells or by expressing an antisense molecule, or the like. Such a ds recombinant nucleic acid molecule can be provided to a cell by contacting the cell ex vivo, then administering the cell to the subject, such a method also allowing for selection and/or expansion of the cells containing the ds recombinant nucleic acid molecule prior to such administration, or can be provided directly to the subject. For administration to a living subject, the ds recombinant nucleic acid molecule, which is covalently linked in one or both strands, generally is formulated in a composition suitable for administration to the subject. Thus, the invention provides compositions containing a ds recombinant nucleic acid molecule covalently linked in one or both strands, generated according to a method of the invention. As disclosed herein, such nucleic acid molecules are useful as medicaments for treating a subject suffering from a pathological condition.

A composition for administration generally is formulated using one or more pharmaceutically acceptable carriers as well known in the art and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition, which can be, for example, orally or parenterally such as intravenously, and by injection, intubation, or other such method known in the art. A composition of the invention also can contain a second reagent such as a diagnostic reagent, nutritional substance, toxin, or therapeutic agent, for example, a cancer chemotherapeutic agent.

The ds recombinant nucleic acid molecule covalently linked in one or both strands, can be incorporated within an encapsulating material such as into an oil-in-water emulsion, a microemulsion, micelle, mixed micelle, liposome, microsphere or other polymer matrix (see, for example, Gregoriadis, *Liposome Technology*, Vol. 1 (CRC Press, Boca Raton, Fla. 1984); Fraley, et al., *Trends Biochem. Sci.*, 6:77, 1981, each of which is incorporated herein by reference). Liposomes, for example, which consist of phospholipids or other lipids, are nontoxic, physiologically acceptable and metabolizable carriers that are relatively simple to make and administer. "Stealth" liposomes (see, for example, U.S. Pat. Nos. 5,882,679; 5,395,619; and 5,225,212, each of which is incorporated herein by reference) are an example of such encapsulating materials particularly useful for preparing a pharmaceutical composition, and other "masked" liposomes similarly can be used, such liposomes extending the time that a nucleic acid molecule remains in the circulation. Cationic liposomes, for example, also can be modified with specific receptors or ligands (Morishita et al., *J. Clin. Invest.*, 91:2580–2585, 1993, which is incorporated herein by reference). The nucleic acid molecule also can be introduced into a cell by complexing it with an adenovirus-polylysine complex (see, for example, Michael et al., *J. Biol. Chem.* 268:6866–6869, 1993, which is incorporated herein by reference). Such compositions can be particularly useful for introducing a nucleic acid molecule into a cell in vivo or in vitro, including ex vivo, wherein the cell containing the nucleic acid molecule is administered back to the subject (see U.S. Pat. No. 5,399,346, which is incorporated herein by reference). A nucleic acid molecule generated according to a method of the invention also can be introduced into a cell using a biolistic method (see, for example, Sykes and Johnston, supra, 1999).

The following examples are intended to illustrate but not limit the invention.

EXAMPLE 1

Construction of Covalently Linked Double Stranded Recombinant Nucleic Acid Molecules Using Topoisomerase This experiment demonstrates that topoisomerase can be used to produce covalently linked double stranded (ds) recombinant nucleic acid molecules.

A. Methods

Except where indicated, experiments were performed using the following methods. PCR was performed in 50 µl reactions, including 10 ng plasmid (template), 100 ng each primer, 2.5 Units Taq DNA polymerase (Sigma), 5 µl 10×PCR buffer, and 4 µl of dNTPs (200 µM each). An initial denaturation was performed by incubating the reaction at 94° C. for 4 min; followed by 30 cycles of PCR using 94° C. (45 sec) for denaturation, 55° C. (45 sec) for primer annealing and 72° C. (1 min per kb of target sequence) for extension. After cycling, the reactions were incubated at 72° C. (10 min), and then placed at 4° C.

Topoisomerase joining reactions were performed in 5 µl, including 50–100 ng each amplified element (PCR-generated or synthetic), 0.5 µl 500 mM Tris (pH 7.5), and 0.5 µg topoisomerase. Reactions were incubated at room temperature for 5 min, then 1–2 µl of the Topo-linked product was used for linear fragment generation.

Linear fragment generation by PCR was performed in 50 µl reactions, including 1–2 µl of the Topo-linked product (template), 100 ng each primer, 2.5 U Taq DNA polymerase (Sigma), 5 µl 10×PCR buffer, and 4 µl dNTPs (200 µM each). PCR was performed as described above.

The resultant linear fragment was purified using a SNAP Miniprep Kit (Invitrogen) as described by the manufacturer. Essentially, 100 µl PCR product was mixed with 300 µl Binding Buffer; 750 µl isopropanol, and the mixture was applied to a SNAP Miniprep Column/Collection Tube and centrifuged at 7,000 rpm for 30 sec. The column was washed with 700 µl Wash Buffer, centrifuged at 7,000 rpm for 30 sec; then washed with 900 µl 1×Final Wash and centrifuged at 7,000 rpm for 30 sec. The column was then centrifuged at 7,000 rpm for an additional 30 sec to remove all remaining liquid. Water (30 to 50 µl) was added and the column was centrifuged at 7,000 rpm for 30 sec to elute the purified DNA. DNA concentration was determined by spectrophotometry.

B. Generation of Topoisomerase Linked Linear Nucleic Acid Molecules

Figure 2:
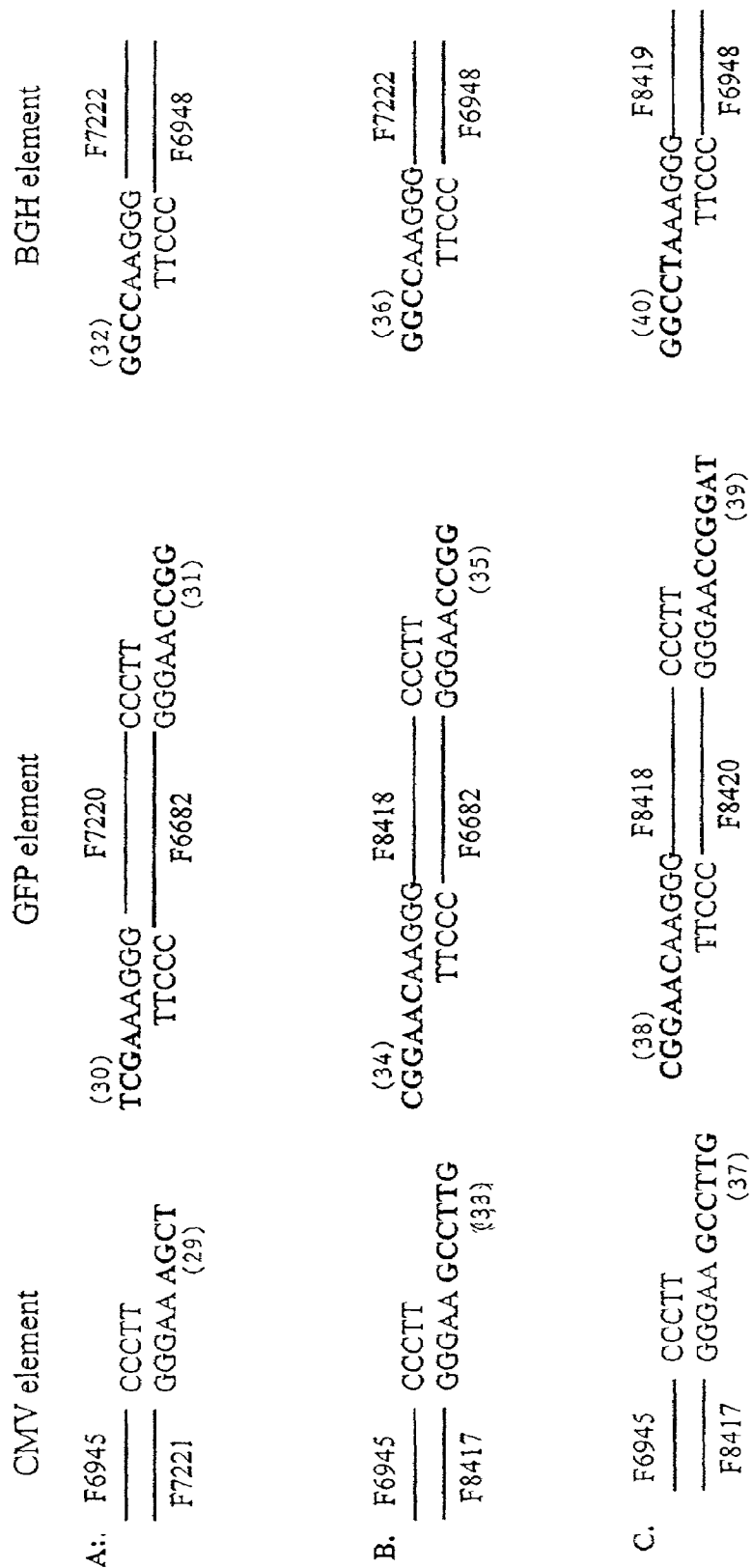
FIGS. 2A to 2C show the ends of PCR products representing a cytomegalovirus promoter element ("CMV"), a green fluorescent protein element ("GFP"), and a bovine growth hormone polyadenylation signal ("BGH") element. Primers used to construct the PCR products of FIGS. 2A, 2B and 2C are indicated by an "F" number (see Table 1). The portion of one or both ends including the topoisomerase recognition site (CCCTT) is shown. Bold print indicates overhanging sequences.

PCR primers were designed to examine the directional addition of elements to the coding sequence of green fluorescent protein (GFP; see FIG. 2). The CMV promoter (approximately 700 bp) and BGH polyadenylation signal sequence (approximately 380 bp) were amplified from a pCMV/myc/nuc plasmid template, and the GFP element (approximately 700 bp) was amplified from a pcDNA3.1/GFP plasmid template (Invitrogen) using the primers indicated in FIG. 2. The resultant amplification products were joined using topoisomerase as described above, and a portion of the ligation reaction was used as template for PCR with primers F6945 (SEQ ID NO: 11) and F6948 (SEQ ID NO: 15) to amplify the entire construct (CMV+GFP+BGH; approximately 1,700 bp). In addition, 5 µl of the ligation mixture was treated with proteinase K for 30 min at 37° C. to remove any bound topoisomerase, and then subjected to electrophoresis on a 3–8% NuPAGE Tris-acetate gel to examine the ligated products.

Only a small amount of ligation product of the correct size (1.7 kb) was observed when the recombinant nucleic acid molecules were generated using elements having palindromic overhanging sequence (FIG. 2A or 2B), whereas significant quantities of the desired product were generated using elements having non-palindromic overhangs (FIG. 2C). These results demonstrate that the efficiency of generating a ds recombinant nucleic acid molecule covalently linked in both strands containing nucleotide sequences operatively linked in a predetermined orientation is related to the nature of the overhang sequence. In particular, the selection of overhanging sequences that lack palindromic regions result in the efficient generation of a desired ds recombinant nucleic acid molecule covalently linked in both strands, whereas the presence of palindromic sequences in the overhangs allows the formation of ligation products other than the intended product, thus decreasing the efficiency of generating a desired product.

EXAMPLE 2

Functional Characterization of Topoisomerase-Generated DS Recombinant Nucleic Acid Molecules This example demonstrates that a method of the invention provides a means to generate functional ds recombinant nucleic acid molecules covalently linked in both strands.

A. Expression of Sense and Antisense mRNA from a Topo-Ligated Construct

The ability to create a ds recombinant nucleic acid molecule containing functional upstream and downstream elements flanking a gene of interest was examined using two synthetic elements containing either a T7 or a T3 promoter sequence. The elements were made by annealing pairs of synthetic oligonucleotides. The T7 linker was generated by mixing equal molar amounts of T7top (F9304; SEQ ID NO: 20) and T7bottom (F9305; SEQ ID NO: 21) oligonucleotides (Table 1). The T3 linker was generated by mixing equal molar amounts of T3top (F9661; SEQ ID NO: 23) and T7bottom (F9662; SEQ ID NO: 24) oligonucleotides (Table 1). The mixtures were heated in boiling water for 5 min, then allowed to cool to room temperature. Both elements were designed to contain a topoisomerase recognition site at one end.

The GFP gene was amplified with GFP primers F8418 (SEQ ID NO: 17) and F8420 (SEQ ID NO: 18; Table 1; see, also, FIG. 2C). Unpurified GFP PCR product (2 µl) was mixed with 50 ng of T7 linker and 50 ng of T3 linker, topoisomerase was added, and the topo-joining reaction was allowed to proceed at room temperature for 5 min. Two µl of the joining reaction was used as template for a 50 µl PCR reaction with primers for the T7 and T3 sequences.

After amplification, a 4 µl aliquot of the PCR reaction was used as template for in vitro transcription. The reaction was performed using a Promega RiboProbe In Vitro Transcription Systems kit according to the manufacturer's instruction. The reaction was allowed to proceed for 60 min at 37° C. with T7 or T3 RNA polymerase (final volume, 20 µl). Aliquots of the in vitro transcription reactions were digested with RNase or DNase, then undigested and digested samples were subjected to electrophoresis in a 2% TBE gel. A predominant band of the predicted size (either sense or antisense orientation) was observed in the undigested samples. No decrease in the product band was noted in samples treated with DNase. The product bands disappeared when samples were treated with RNase indicating the product was RNA. These results demonstrate that topoisomerase can be used according to a method of the invention to generate a ds recombinant nucleic acid molecule covalently linked in both strands in a predetermined orientation, and that an RNA transcript can be expressed from such a nucleic acid molecule.

B. Expression of a Translation Product from a Topo-ligated Construct

The ability of topoisomerase ligated polynucleotide to support coupled in vitro transcription/translation was examined. A ds recombinant nucleic acid molecule was generated according to a method of the invention by linking an element containing a T7 promoter (plus a Kozak sequence) to lacZ PCR products of 1 kb, 2 kb, or 3 kb. Two µl of the generated products were used as template for PCR amplification reactions (primers, SEQ ID NOS: 25–28; Table 1). Unpurified aliquots of the amplification reactions (3 µl) were used as templates for coupled transcription/translation with a TNT T7 Quick for PCR DNA Kit according to the manufacturer's instructions (Promega).

Two µl aliquots from each reaction were separated by electrophoresis on a Tris-glycine gel (Novex), then visualized by autoradiography, which revealed protein products that migrated at the expected sizes. These results demonstrate that a method of the invention can be used to produce a ds recombinant nucleic acid molecule covalently linked in both strands useful as a template for expressing a polypeptide by a coupled in vitro transcription/translation reaction.

C. Generation of Topo-Ligated Constructs for Performing a Two Hybrid Assay

Two hybrid assays provide a powerful method for detecting protein—protein interactions in vivo. These assays are based on the fact that many eukaryotic transcriptional activators consist of two physically and functionally separable domains, including a DNA binding domain, which binds to a specific DNA sequence, and a transcriptional activation domain, which interacts with the basal transcriptional machinery. The association of a transactivation domain with a DNA binding domain can promote the assembly of a functional RNA polymerase II complex, thereby allowing transcriptional activation, for example, of a detectable reporter gene (Field and Song, supra, 1989). Where a first protein, X, is fused to a DNA binding domain, for example, a GAL4 binding domain, and a second protein, Y, which can be the same or different from X, is fused into a transactivation domain, for example, a VP 16 domain, an interaction of proteins X and Y can be identified by detecting transcription of a reporter gene having a GAL4 promoter.

The ability of a method of the invention to generate linear constructs for expressing fusion proteins for performing a mammalian two-hybrid assay was examined. PCR was used to generate GAL4 (F10779 and F12667 primers; SEQ ID NOS: 1 and 3, respectively), VP16 (F10779 and F12668 primers; SEQ ID NOS: 1 and 5, respectively), p53 (F12669 and F12505 primers; SEQ ID NOS: 8 and 4, respectively), T antigen (F12670 and F12505 primers; SEQ ID NOS: 9 and 4, respectively), and SV40pA (F12016 and F561 primers; SEQ ID NOS: 6 and 7, respectively) elements containing topoisomerase sites at the appropriate ends. Topoisomerase was used to create the covalently linked, double stranded constructs GAL4+p53+SV40pA and VP16+T antigen+SV40pA, and the resultant ligation products were used as templates for PCR amplification.

Purified GAL4+p53+SV40pA and VP16+T antigen+SV40pA PCR constructs were co-transfected with a lacZ reporter gene (pGene/lacZ plasmid; Invitrogen) into CHO cells (6 well plate, $1\times10^5$ cells/well). In parallel experiments, the use of plasmid vectors containing the expression constructs was examined, as was the use of PCR reaction mixtures containing the unpurified constructs. Control reactions were performed using GAL4+pA and VP16+pA without inserts (negative controls) or p53+VP16 (positive control). Cells were lysed 48 hr after transfection and reporter gene activity was measured using a β-galactosidase assay kit.

Figure 3:
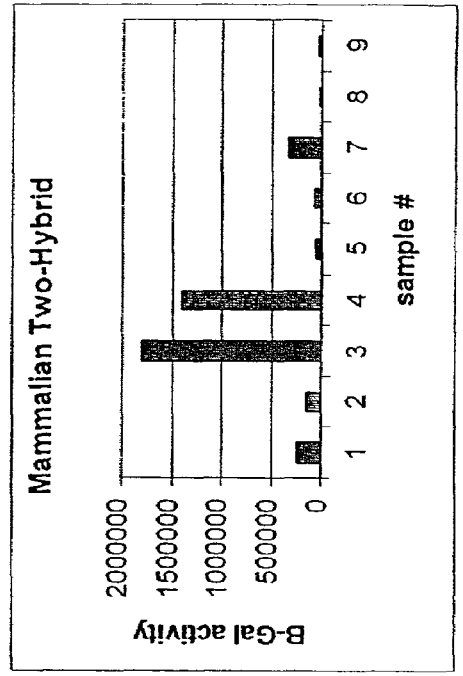
FIGS. 3A and 3B show constructs (FIG. 3A) and results (FIG. 3B) of experiments examining the ability to use ds recombinant nucleic acid molecule covalently linked in both strands that encode polypeptides for performing a two hybrid assay.

A high level of reporter gene activity was detected with the positive control (FIG. 3, sample 3) and in the sample co-transfected with the reporter gene and the linear GAL4+p53+SV40pA and VP16+T antigen+SV40pA constructs (FIG. 3, sample 4). Low level activity (but greater than that of the negative controls; samples 5, 6, 8 and 9) was detected when the plasmid version of the constructs was used (FIG. 3, sample 1). Low level activity was also observed in the sample co-transfected with the unpurified, PCR-generated prey and bait constructs (sample 7). These results demonstrate that a method of the invention can be used to prepare constructs useful for performing a two hybrid assay.

Although the invention has been described with reference to the above examples, it will be understood that modifications and variations are encompassed within the spirit and scope of the invention. Accordingly, the invention is limited only by the following claims.

What is claimed is:

1. A method of generating a double stranded (ds) recombinant nucleic acid molecule covalently linked in both strands, the method comprising contacting a first linear ds nucleic acid molecule, a second linear ds nucleic acid molecule, wherein said first nucleic acid molecule and said second nucleic acid molecule comprise a topoisomerase recognition site at or near each of their ends, and a topoisomerase, thereby generating a ds recombinant nucleic acid molecule covalently linked in both strands, wherein the recombinant nucleic acid molecule does not contain a nick in either strand at the position where the first and second nucleic acid molecules are joined.

2. The method of claim 1, wherein the topoisomerase is a site specific topoisomerase.

3. The method of claim 2, wherein the site specific topoisomerase is a type I topoisomerase.

4. The method of claim 3, wherein the topoisomerase is a type IB topoisomerase or a catalytic domain of a type IB topoisomerase.

5. The method of claim 4, wherein the type IB topoisomerase is a poxvirus type IB topoisomerase.

6. The method of claim 1, wherein the topoisomerase recognition site is a recognition site for a type IB topoisomerase.

7. The method of claim 1, wherein one or both of said first and said second nucleic acid molecules is a polymerase chain reaction (PCR) amplification product produced using a PCR primer pair, wherein each PCR primer of the PCR primer pair comprises a topoisomerase recognition site or a complement thereof.

8. The method of claim 1, further comprising contacting said recombinant nucleic acid molecule with an amplification primer pair; and amplifying the recombinant nucleic acid molecule.

9. A method of generating a double stranded (ds) recombinant nucleic acid molecule covalently linked in both strands, the method comprising contacting a first topoisomerase-charged linear ds nucleic acid molecule and a second topoisomerase-charged linear ds nucleic acid molecule, wherein said first and second nucleic acid molecules are topoisomerase-charged at or near each of their ends, thereby generating a ds recombinant nucleic acid molecule covalently linked in both strands, wherein the recombinant nucleic acid molecule does not contain a nick in either strand at the position where the first and second nucleic acid molecules are joined.

10. The method of claim 9, further comprising a third ds nucleic acid molecule.

11. The method of claim 10, wherein said third ds nucleic acid molecule is topoisomerase-charged at or near both of its ends.

12. The method of claim 9, wherein the topoisomerase is a type IB topoisomerase or a catalytic domain of a type IB topoisomerase.

13. A method of generating a double stranded (ds) recombinant nucleic acid molecule covalently linked in both strands, the method comprising:

a) amplifying a portion of a first ds nucleic acid molecule using an amplification primer pair, wherein each PCR primer of the primer pair comprises a topoisomerase recognition site or a complement thereof, thereby producing an amplified first linear ds nucleic acid molecule comprising, a topoisomerase recognition site at or near both 3' termini or both 5' termini; and b) contacting the first nucleic acid molecule; a second linear ds nucleic acid molecule comprising a topoisomerase recognition site at or near each of its ends; and a topoisomerase, thereby generating a ds recombinant nucleic acid molecule covalently linked in both strands, wherein the recombinant nucleic acid molecule does not contain a nick in either strand at the position where the first and second nucleic acid molecules are joined.

14. The method of claim 13, wherein the at least one topoisomerase is a type IB topoisomerase or a catalytic domain of a type IB topoisomerase.

15. The method of claim 13, further comprising a third linear ds nucleic acid molecule.

16. The method of claim 15, wherein said third nucleic acid molecule comprises a topoisomerase recognition site at or near both of its ends.

17. The method of claim 13, wherein said first nucleic acid molecule and said second nucleic acid molecule each comprise an overhanging sequence at an end comprising the topoisomerase recognition site.

18. The method of claim 17, wherein the topoisomerase recognition site is at or near both 3' termini, and wherein the overhanging sequence is a 5' overhanging sequence.

19. The method of claim 17, wherein the overhanging sequences of said ends of said nucleic acid molecules to be covalently linked are complementary.

20. The method of claim 13, wherein the second nucleic acid molecule comprises or encodes a regulatory element.

21. The method of claim 20, wherein the regulatory element is a promoter, an enhancer, a silencer, a translation start site, or a polyadenylation signal.

22. The method of claim 20, wherein the regulatory element is an initiator methionine codon or a STOP codon.

23. The method of claim 13, wherein the first nucleic acid molecule comprises an expressible nucleotide sequence.

24. The method of claim 23, wherein the expressible nucleotide sequence encodes a polypeptide.

25. The method of claim 24, wherein the expressible nucleotide sequence comprises an antisense nucleotide sequence, a tRNA, a ribozyme, an RNAi nucleotide sequence, or a triplexing nucleotide sequence.

26. The method of claim 25, wherein the tRNA is a suppressor tRNA.

27. The method of claim 13, wherein the second nucleic acid molecule comprises or encodes a detectable label.

28. The method of claim 27, wherein the detectable label is an enzyme, a substrate for an enzyme, a fluorescent compound, a luminescent compound, a chemiluminescent compound, a radionuclide, a paramagnetic compound, or biotin.

29. The method of claim 13, wherein the second nucleic acid molecule comprises or encodes a tag.

30. The method of claim 29, wherein the tag is an oligonucleotide tag or a peptide tag.

31. The method of claim 30, wherein the peptide tag is a polyhistidine tag, a V5 epitope, or a myc epitope.

32. The method of claim 13, wherein the second nucleic acid molecule encodes a transcription activation domain or a DNA binding domain.

33. The method of claim 13, wherein the first nucleic acid molecule and the second nucleic acid molecule are covalently linked in a predetermined directional orientation.

34. The method of claim 13, further comprising performing a coupled transcription/translation reaction using the ds recombinant nucleic acid molecule.

35. The method of claim 13, further comprising transfecting a cell with the ds recombinant nucleic acid molecule.

36. The method of claim 13, wherein a primer of the primer pair comprises a complement of a type IB topoisomerase recognition site, said amplification primer further comprising a 5' hydroxyl group.

37. The method of claim 13, wherein the primer comprising the topoisomerase recognition site or complement thereof further comprises of 2 to 12 nucleotides 5' to said topoisomerase recognition site or complement thereof.

38. The method of claims 1 or 7, wherein said first and second nucleic acid molecules comprise a topoisomerase recognition site at or near each of their 3' termini.

39. The method of claim 9, wherein said first and second nucleic acid molecules are topoisomerase-charged at or near each of their 3' termini.

40. The method of claim 13, wherein said first and second nucleic acid molecules comprise a topoisomerase recognition site at or near each of their 3' termini.

41. The method of claim 1 or 7, wherein said first and second nucleic acid molecules comprise a topoisomerase recognition site at or near each of their 5' termini.

42. The method of claim 9, wherein said first and second nucleic acid molecules are topoisomerase-charged at or near each of their 5' termini.

43. The method of claim 13, wherein said first and second nucleic acid molecules comprise a topoisomerase recognition site at or near each of their 5' termini.

44. The method of claim 1, wherein said first nucleic acid molecule comprises a topoisomerase recognition site at or near the 3' and 5' termini of one strand, and said second nucleic acid molecule comprises a topoisomerase recognition site at or near the 3' and 5' termini of one strand.

45. The method of claim 9, wherein said first nucleic acid molecule is topoisomerase-charged at or near the 3' and 5' termini of one strand, and said second nucleic acid molecule is topoisomerase charged at or near the 3' and 5' termini of one strand.

46. The method of claim 1, wherein said first nucleic acid molecule comprises a topoisomerase recognition site at or near the 3' terminus of one strand and the 5' terminus of the second strand, and said second nucleic acid molecule comprises a topoisomerase recognition site at or near the 3' terminus of one strand and the 5' terminus of the other strand.

47. The method of claim 9, wherein said first nucleic acid molecule is topoisomerase charged at or near the 3' terminus of one strand and the 5' terminus of the other strand, and said second nucleic acid molecule is topoisomerase-charged at or near the 3' terminus of one strand and the 5' terminus of the other strand.

48. The method of claim 1, further comprising a third linear ds nucleic acid molecule.

49. The method of claim 48, wherein said third ds nucleic acid molecule comprises a topoisomerase recognition site at or near both of its ends.

50. The method of claim 12, wherein the type IB topoisomerase is a poxvirus type IB topoisomerase.

51. The method of claim 14, wherein the type IB topoisomerase is a poxvirus type IB topoisomerase.

* * * * *